(12) United States Patent
McArthur et al.

(10) Patent No.: US 7,361,682 B2
(45) Date of Patent: Apr. 22, 2008

(54) INDOLE DERIVATIVES AS H3 INVERSE AGONISTS

(75) Inventors: Silvia Gatti McArthur, Basel (CH); Cornelia Hertel, Muenchenstein (CH); Matthias Heinrich Nettekoven, Grenzach-Wyhlen (DE); Susanne Raab, Basel (CH); Olivier Roche, Folgensbourg (FR); Rosa Maria Rodriguez-Sarmiento, Basel (CH); Franz Schuler, Riehen (CH); Jean-Marc Plancher, Hagenthal le bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 236 days.

(21) Appl. No.: 11/157,093

(22) Filed: Jun. 20, 2005

(65) Prior Publication Data

US 2005/0282864 A1    Dec. 22, 2005

(30) Foreign Application Priority Data

Jun. 21, 2004   (EP)   ................... 04102839

(51) Int. Cl.
| | | |
|---|---|---|
| *A61K 31/55* | (2006.01) | |
| *A61K 31/541* | (2006.01) | |
| *A61K 31/5377* | (2006.01) | |
| *A61K 31/454* | (2006.01) | |
| *A61K 31/4545* | (2006.01) | |
| *A61K 31/4045* | (2006.01) | |
| *C07D 209/42* | (2006.01) | |
| *C07D 401/02* | (2006.01) | |
| *C07D 413/02* | (2006.01) | |
| *C07D 417/02* | (2006.01) | |

(52) U.S. Cl. ................. 514/419; 514/414; 514/217.04; 514/228.2; 514/235.2; 514/316; 514/323; 540/597; 544/124; 544/144; 546/187; 546/201; 548/468

(58) Field of Classification Search ................. 540/597; 544/124, 144; 546/187, 201; 548/468
See application file for complete search history.

(56) References Cited

U.S. PATENT DOCUMENTS 6,673,829 B2 *   1/2004   Dorwald et al. ......... 514/210.2

6,919,355 B2 *   7/2005   Horvath et al. ............. 514/326

FOREIGN PATENT DOCUMENTS

| EP | 0 624 575 A1 | 11/1994 |
|---|---|---|
| EP | 0 978 512 A1 | 2/2000 |
| WO | WO 01/74773 A2 | 10/2001 |
| WO | WO 02/072548 A2 | 9/2002 |
| WO | WO 04/000831 A1 | 12/2003 |

OTHER PUBLICATIONS

Witkin et al. Pharmacology & Therapeutics 2004, 103, 1-20.*
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Brashear, K.M., et al., Bioorganic and Medicinal Chemistry Letters, vol. 7, No. 21, pp. 2793-2798 (1997), XP002347978.

* cited by examiner

*Primary Examiner*—Kamal A. Saeed
*Assistant Examiner*—Jason M Nolan
(74) *Attorney, Agent, or Firm*—George W. Johnston; Dennis P. Tramaloni; Samuel H. Megerditchian

(57) ABSTRACT

The present invention relates to compounds of formula I:

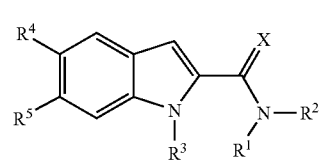

wherein X, $R^1$, $R^2$, $R^3$, $R^4$ and $R^5$ are as defined in the description and claims, and pharmaceutically acceptable salts thereof, to the preparation of such compounds and pharmaceutical compositions containing them. The compounds are useful for the treatment and/or prevention of diseases which are associated with the modulation of H3 receptors.

26 Claims, No Drawings

INDOLE DERIVATIVES AS H3 INVERSE AGONISTS

FIELD OF THE INVENTION

The present invention is directed to novel indole derivatives, their manufacture, pharmaceutical compositions containing them and their use as medicaments.

In particular, the present invention relates to compounds of the formula I:

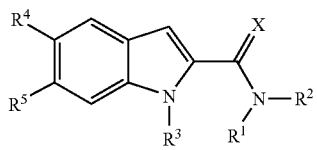

and pharmaceutically acceptable salts thereof.

The compounds of formula I are antagonists and/or inverse agonists at the histamine 3 receptor (H3 receptor) and are useful in treating obesity and other disorders.

All documents cited or relied upon below are expressly incorporated herein by reference.

BACKGROUND

Histamine (2-(4-imidazolyl) ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs RL and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

SUMMARY OF THE INVENTION

In one embodiment of the present invention, provided are compounds of the formula I:

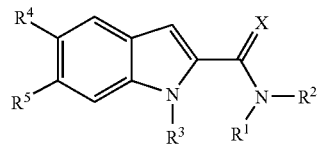

wherein
X is O or S;
$R^1$ is selected from the group consisting of hydrogen,
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocyclyl ring may be unsubstituted or substituted with one or two lower alkyl groups;
$R^2$ is selected from the group consisting of hydrogen,
lower alkyl, lower alkenyl, lower alkinyl, cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated heterocyclic ring
being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen;
$R^3$ is selected from the group consisting of hydrogen, lower alkyl, lower alkoxyalkyl, lower halogenalkyl, lower cycloalylalkyl, lower alkylsulfonyl and lower alkanoyl;
$R^4$ is —O-Het and $R^5$ is hydrogen, or
$R^4$ is hydrogen or fluoro and $R^5$ is —O-Het;
Het is selected from

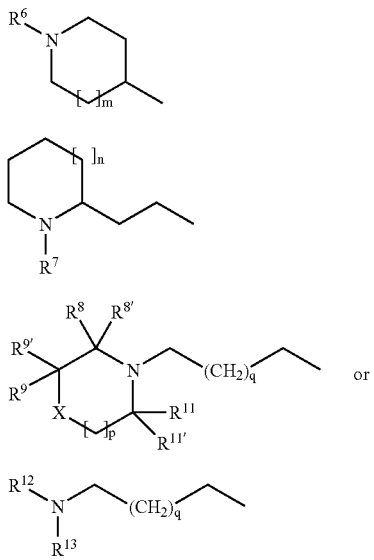

Het 1

Het 2

Het 3

Het 4 wherein
m is 0, 1 or 2;

$R^6$ is selected from lower alkyl, cycloalkyl, lower cycloalkylalkyl and lower phenylalkyl;
n is 0, 1 or 2;
$R^7$ is lower alkyl;
p is 0, 1 or 2;
q is 0, 1 or 2;
X is selected from $CR^{10}R^{10'}$, O and S;
$R^8$, $R^{8'}$, $R^9$, $R^{9'}$, $R^{10}$, $R^{10'}$, $R^{11}$ and $R^{11'}$ independently from each other are selected from the group consisting of hydrogen, lower alkyl, hydroxy, halogen and dialkylamino, or
$R^9$ and $R^{10}$ together form a double bond;
$R^{12}$ is lower alkyl;
$R^{13}$ is $C_3$-$C_6$-alkyl;
and pharmaceutically acceptable salts thereof.
In another embodiment of the invention, compounds of formula I are provided, wherein
X is O or S;
$R^1$ is selected from the group consisting of hydrogen,
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocyclyl ring may be unsubstituted or substituted with one or two lower alkyl groups;
$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring
being unsubstituted or substituted by one, two or three groups independently selected from lower alkyl, halogen, halogenalkyl, hydroxy, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen;

$R^3$ is hydrogen or lower alkyl;
$R^4$ is —O-Het and $R^5$ is hydrogen, or
$R^4$ is hydrogen or fluoro and $R^5$ is —O-Het;
Het is selected from

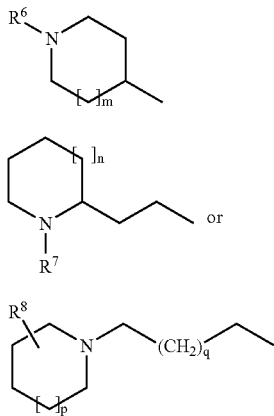

Het 1

Het 2

Het 3' wherein
m is 0, 1 or 2;
$R^6$ is lower alkyl;
n is 0, 1 or 2;
$R^7$ is lower alkyl;
p is 0, 1 or 2;
q is 0, 1 or 2;
$R^8$ is hydrogen or lower alkyl;

and pharmaceutically acceptable salts thereof.

In a further embodiment of the invention, pharmaceutical compositions are provided comprising a therapeutically effective amount of a compound as defined above and a pharmaceutically acceptable carrier and/or adjuvant.

In a still further embodiment of the invention, a method for the treatment and/or prevention of diseases which are associated with the modulation of H3 receptors is provided, comprising the step of administering a therapeutically effective amount of a compound according to formula I to a human being or animal in need thereof.

DETAILED DESCRIPTION

The present invention provides for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-8}$-alkinyl", alone or in combination, signifies a straight-chain or branched hydrocarbon residue comprising a triple bond and up to 8, preferably up to 6, particularly preferred up to 4 carbon atoms. Examples of alkinyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cydopentyl, cyclohexyl or cycloheptyl. Especially preferred are cyclopropyl, cyclopentyl and cyclohexyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfanyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group —CO—$NH_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl and pyridyl.

The term "lower heteroarylalkyl" or "heteroaryl-$C_{1-8}$-alcyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiamorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. The heteroyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also include physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

Preferred compounds of formula I of the present invention are compounds of formula I, wherein
$R^1$ is selected from the group consisting of
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups, and
$R^2$ is hydrogen or lower alkyl.

Especially preferred are compounds of formula I, wherein
$R^1$ is selected from the group consisting of
lower alkyl, cycloalkyl, lower cycloalkylalkyl, lower alkoxyalkyl,
lower phenylalkyl,
lower heteroarylalkyl, and
lower heterocyclylalkyl wherein the heterocyclyl ring may be unsubstituted or substituted with one or two lower alkyl groups, and
$R^2$ is hydrogen or lower alkyl.

Even more preferred are compounds of formula I, wherein $R^1$ and $R^2$ are lower alkyl.

Furthermore, compounds of formula I according to the present invention are preferred, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

More preferred are compounds of formula I according to the invention, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said saturated heterocyclic ring being unsubstituted or substituted by one, two or three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Even more preferably, $R^1$ and $R^2$ together with the nitrogen atom to which they are attached form a heterocyclic ring selected from the group consisting of morpholine, piperidine, azepane, pyrrolidine and azetidine, wherein the ring is unsubstituted or substituted by lower alkyl. Especially preferred are those compounds of formula I, wherein $R^1$ and $R^2$ together with the nitrogen atom to which they are attached form a heterocyclic ring selected from morpholinyl, 2,6-dimethylmorpholinyl, azepanyl, piperidinyl, 2-methylpiperidinyl, 4-methylpiperidinyl, pyrrolidinyl, 2-methylpyrrolidinyl and azetidinyl.

Furthermore, compounds of formula I, wherein $R^3$ is hydrogen, are preferred.

Another group of preferred compounds of formula I are those, wherein $R^3$ is selected from the group consisting of lower alkyl, lower alkoxyalkyl, lower halogenalkyl, lower cycloalkylalkyl, lower alkylsulfonyl and lower alkanoyl Compounds of formula I according to the present invention, wherein $R^4$ is —O-Het and $R^5$ is hydrogen, are especially preferred.

Compounds of formula I, wherein $R^4$ is hydrogen or fluoro and $R^5$ is —O-Het, are also preferred. Especially preferred are compounds of formula I, wherein $R^4$ is hydrogen and $R^5$ is —O-Het.

Preferably, Het is a group selected from

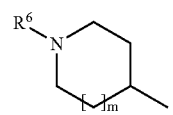

Het 1

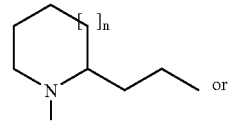

Het 2 or

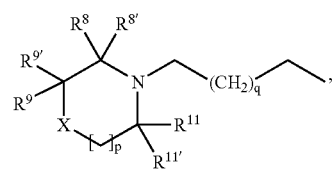

Het 3 wherein m, n, p, q, $R^6$, $R^7$, $R^8$, $R^{8'}$, $R^9$, $R^{9'}$, $R^{11}$, $R^{11'}$ and X are as defined herein before. Especially preferred compounds of formula I according to the present invention are those, wherein Het signifies

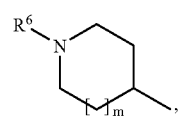

Het 1 wherein m is 0, 1 or 2, and $R^6$ is selected from lower alkyl, cycloalkyl, lower cycloalkylalkyl and lower phenylalkyl, with those compounds, wherein $R^6$ is lower alkyl, being especially preferred.

Within this group, those compounds of formula I are preferred, wherein m is 0, thus meaning pyrrolidine groups are preferred.

A further preferred group includes those compounds of formula I, wherein m is 1, thus meaning piperidine groups are also preferred.

Another preferred group of compounds are those compounds of formula I, wherein Het signifies

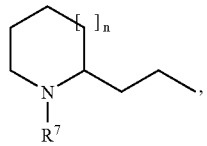

Het 2 wherein n is 0, 1 or 2; and $R^7$ is lower alkyl, with those compounds, wherein n is 0, thus meaning pyrrolidine derivatives, being more preferred.

Another group of preferred compounds of formula I are those, wherein Het signifies

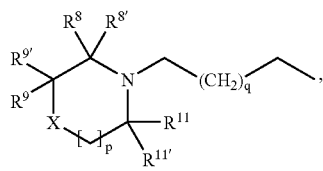

Het 3 wherein p is 0, 1 or 2; q is 0, 1 or 2; X is selected from $CR^{10}R^{10'}$, O and S; and $R^8$, $R^{8'}$, $R^9$, $R^{9'}$, $R^{10}$, $R^{10'}$, $R^{11}$ and $R^{11'}$ independently from each other are selected from the group consisting of hydrogen, lower alkyl, hydroxy, halogen and dialkylamino.

Preferred are compounds wherein p is 0 or 1.

$R^9$ and $R^{10}$ together may also form a double bond, meaning a compound of the formula

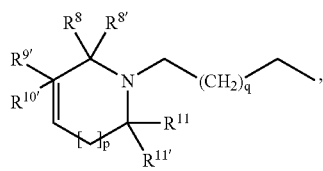

Het 3a wherein p, q, $R^8$, $R^{8'}$, $R^{9'}$, $R^{10'}$, $R^{11}$ and $R^{11'}$ are as defined above.

Further preferred compounds of formula I according to the present invention are those, wherein Het signifies

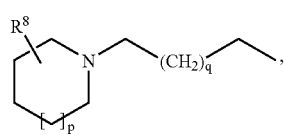

Het 3' wherein p is 0, 1 or 2, q is 0, 1 or 2, and $R^8$ is hydrogen or lower alkyl. Within this group, those compounds of formula I are preferred, wherein p is 1 and q is 1, thus meaning piperidine groups are preferred.

Another group of preferred compounds are those, wherein Het signifies

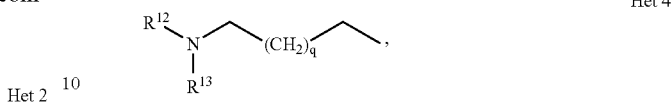

Het 4 wherein q is 0, 1 or 2, $R^{12}$ is lower alkyl and $R^{13}$ is $C_3$-$C_6$-alkyl.

Examples of preferred compounds of formula I are the following:

morpholin-4-yl-[5-(3-piperidin-1-yl-propoxy)-1H-indol-2-yl]-methanone,
[5-(1-isopropyl-pyrrolidin-3-yloxy)-1H-indol-2-yl]-morpholin-4-yl-methanone,
(3,4-dihydro-1H-isoquinolin-2-yl)-[5-(1-isopropyl-pyrrolidin-3-yloxy)-1H-indol-2-yl]-methanone,
(3,4-dihydro-1H-isoquinolin-2-yl)-{5-[2-(1-methyl-pyrrolidin-2-yl)-ethoxy]-1H-indol-2-yl}-methanone,
5-(1-isopropyl-pyrrolidin-3-yloxy)-1H-indole-2-carboxylic acid cyclopropylmethyl-propyl-amide,
5-(1-isopropyl-pyrrolidin-3-yloxy)-1H-indole-2-carboxylic acid diethylamide,
5-(1-isopropyl-pyrrolidin-3-yloxy)-1H-indole-2-carboxylic acid ethyl-methyl-amide,
5-(1-isopropyl-pyrrolidin-3-yloxy)-1H-indole-2-carboxylic acid methyl-propyl-amide,
(2,6-dimethyl-morpholin-4-yl)-[5-(-isopropyl-pyrrolidin-3-yloxy)-1H-indol-2-yl]-methanone,
5-(1-isopropyl-pyrrolidin-3-yloxy)-1H-indole-2-carboxylic acid methyl-phenethyl-amide,
(2,5-dihydro-pyrrol-1-yl)-[5-(1-isopropyl-pyrrolidin-3-yloxy)-1H-indol-2-yl]-methanone,
5-(1-isopropyl-pyrrolidin-3-yloxy)-1H-indole-2-carboxylic acid cyclohexyl-methyl-amide,
(3-hydroxy-pyrrolidin-1-yl)-[5-(1-isopropyl-pyrrolidin-3-yloxy)-1H-indol-2-yl]-methanone,
azepan-1-yl-[5-(1-isopropyl-pyrrolidin-3-yloxy)-1H-indol-2-yl]-methanone,
[5-(1-isopropyl-pyrrolidin-3-yloxy)-1H-indol-2-yl]-(4-methyl-piperidin-1-yl)-methanone,
5-(1-isopropyl-pyrrolidin-3-yloxy)-1H-indole-2-carboxylic acid isopropyl-methyl-amide,
5-(1-isopropyl-pyrrolidin-3-yloxy)-1H-indole-2-carboxylic acid isobutyl-amide,
[5-(1-isopropyl-pyrrolidin-3-yloxy)-1H-indol-2-yl]-(2-methyl-piperidin-1-yl)-methanone,
5-(1-isopropyl-piperidin-4-yloxy)-1H-indole-2-carboxylic acid cyclopropylmethyl-propyl-amide,
5-(1-isopropyl-piperidin-4-yloxy)-1H-indole-2-carboxylic acid diethylamide,
5-(1-isopropyl-piperidin-4-yloxy)-1H-indole-2-carboxylic acid isopropylamide,
5-(1-isopropyl-piperidin-4-yloxy)-1H-indole-2-carboxylic acid tert-butylamide,
5-(1-isopropyl-piperidin-4-yloxy)-1H-indole-2-carboxylic acid cyclopropylamide,
5-(1-isopropyl-piperidin-4-yloxy)-1H-indole-2-carboxylic acid ethyl-methyl-amide,
5-(1-isopropyl-piperidin-4-yloxy)-1H-indole-2-carboxylic acid propylamide, 5-(1-isopropyl-piperidin-4-yloxy)-1H-indole-2-carboxylic acid methyl-propyl-amide,
5-(1-isopropyl-piperidin-4-yloxy)-1H-indole-2-carboxylic acid allylamide,
5-(1-isopropyl-piperidin-4-yloxy)-1H-indole-2-carboxylic acid prop-2-ynylamide,
(2,6-dimethyl-morpholin-4-yl)-[5-(1-isopropyl-piperidin-4-yloxy)-1H-indol-2-yl]-methanone,
5-(1-isopropyl-piperidin-4-yloxy)-1H-indole-2-carboxylic acid methyl-phenethyl-amide,
(2,5-dihydro-pyrrol-1-yl)-[5-(1-isopropyl-piperidin-4-yloxy)-1H-indol-2-yl]-methanone,
5-(1-isopropyl-piperidin-4-yloxy)-1H-indole-2-carboxylic acid cyclohexyl-methyl-amide,
(3-hydroxy-pyrrolidin-1-yl)-[5-(1-isopropyl-piperidin-4-yloxy)-1H-indol-2-yl]-methanone,
azepan-1-yl-[5-(1-isopropyl-piperidin-4-yloxy)-1H-indol-2-yl]-methanone,
5-(1-isopropyl-piperidin-4-yloxy)-1H-indole-2-carboxylic acid ethyl-(2-methoxy-ethyl)-amide,
[5-(1-isopropyl-piperidin-4-yloxy)-1H-indol-2-yl]-(4-methyl-piperidin-1-yl)-methanone,
5-(1-isopropyl-piperidin-4-yloxy)-1H-indole-2-carboxylic acid isopropyl-methyl-amide,
5-(1-isopropyl-piperidin-4-yloxy)-1H-indole-2-carboxylic acid isobutyl-amide,
[5-(1-isopropyl-piperidin-4-yloxy)-1H-indol-2-yl]-(2-methyl-piperidin-1-yl)-methanone,
(4-benzyl-piperazin-1-yl)-[5-(1-isopropyl-piperidin-4-yloxy)-1H-indol-2-yl]-methanone,
5-[2-(1-methyl-pyrrolidin-2-yl)-ethoxy]-1H-indole-2-carboxylic acid cyclopropylmethyl-propyl-amide,
5-[2-(1-methyl-pyrrolidin-2-yl)-ethoxy]-1H-indole-2-carboxylic acid diethylamide,
5-[2-(1-methyl-pyrrolidin-2-yl)-ethoxy]-1H-indole-2-carboxylic acid isopropylamide,
5-[2-(1-methyl-pyrrolidin-2-yl)-ethoxy]-1H-indole-2-carboxylic acid tert-butylamide,
5-[2-(1-methyl-pyrrolidin-2-yl)-ethoxy]-1H-indole-2-carboxylic acid ethyl-methyl-amide,
5-[2-(1-methyl-pyrrolidin-2-yl)-ethoxy]-1H-indole-2-carboxylic acid methyl-propyl-amide,
(2,6-dimethyl-morpholin-4-yl)-{5-[2-(1-methyl-pyrrolidin-2-yl)-ethoxy]-1H-indol-2-yl}-methanone,
5-[2-(1-methyl-pyrrolidin-2-yl)-ethoxy]-1H-indole-2-carboxylic acid methyl-phenethyl-amide,
(2,5-dihydro-pyrrol-1-yl)-{5-[2-(1-methyl-pyrrolidin-2-yl)-ethoxy]-1H-indol-2-yl}-methanone,
5-[2-(1-methyl-pyrrolidin-2-yl)-ethoxy]-1H-indole-2-carboxylic acid cyclohexyl-methyl-amide,
(3-hydroxy-pyrrolidin-1-yl)-{5-[2-(1-methyl-pyrrolidin-2-yl)-ethoxy]-1H-indol-2-yl}-methanone,
azepan-1-yl-{5-[2-(1-methyl-pyrrolidin-2-yl)-ethoxy]-1H-indol-2-yl}-methanone,
(4-methyl-piperidin-1-yl)-{5-[2-(1-methyl-pyrrolidin-2-yl)-ethoxy]-1H-indol-2-yl}-methanone,
5-[2-(1-methyl-pyrrolidin-2-yl)-ethoxy]-1H-indole-2-carboxylic acid isopropyl-methyl-amide,
(2-methyl-piperidin-1-yl)-{5-[2-(1-methyl-pyrrolidin-2-yl)-ethoxy]-1H-indol-2-yl}-methanone,
5-(1-isopropyl-pyrrolidin-3-yloxy)-1H-indole-2-carboxylic acid methyl-(2-pyridin-2-yl-ethyl)-amide,
5-(1-isopropyl-pyrrolidin-3-yloxy)-1H-indole-2-carboxylic acid cyclohexylamide,
5-(1-isopropyl-pyrrolidin-3-yloxy)-1H-indole-2-carboxylic acid (2-piperidin-1-yl-ethyl)-amide,
azetidin-1-yl-[5-(1-isopropyl-pyrrolidin-3-yloxy)-1H-indol-2-yl]-methanone,
(4-isopropyl-piperazin-1-yl)-[5-(1-isopropyl-pyrrolidin-3-yloxy)-1H-indol-2-yl]-methanone,
[5-(1-isopropyl-pyrrolidin-3-yloxy)-1H-indol-2-yl]-(2-methyl-pyrrolidin-1-yl)-methanone,
[5-(1-isopropyl-pyrrolidin-3-yloxy)-1H-indol-2-yl]-pyrrolidin-1-yl-methanone,
[5-(1-isopropyl-pyrrolidin-3-yloxy)-1H-indol-2-yl]-piperidin-1-yl-methanone,
[5-(1-isopropyl-pyrrolidin-3-yloxy)-1H-indol-2-yl]-thiomorpholin-4-yl-methanone,
[5-(1-isopropyl-pyrrolidin-3-yloxy)-1H-indol-2-yl]-(4-methoxy-piperidin-1-yl)-methanone,
[5-(1-isopropyl-pyrrolidin-3-yloxy)-1H-indol-2-yl]-(4-methyl-piperazin-1-yl)-methanone,
(4-benzyl-piperidin-1-yl)-[5-(1-isopropyl-pyrrolidin-3-yloxy)-1H-indol-2-yl]-methanone,
(4,4-difluoro-piperidin-1-yl)-[5-(1-isopropyl-pyrrolidin-3-yloxy)-1H-indol-2-yl]-methanone,
(3,6-dihydro-2H-pyridin-1-yl)-[5-(1-isopropyl-pyrrolidin-3-yloxy)-1H-indol-2-yl]-methanone,
[5-(1-isopropyl-pyrrolidin-3-yloxy)-1H-indol-2-yl]-(3-methyl-piperidin-1-yl)-methanone,
5-(1-isopropyl-pyrrolidin-3-yloxy)-1H-indole-2-carboxylic acid methyl-pyridin-3-ylmethyl-amide,
5-(1-isopropyl-pyrrolidin-3-yloxy)-1H-indole-2-carboxylic acid [2-(2-methyl-piperidin-1-yl)-ethyl]-amide,
(4-hydroxymethyl-piperidin-1-yl)-[5-(1-isopropyl-pyrrolidin-3-yloxy)-1H-indol-2-yl]-methanone,
(1,3-dihydro-isoindol-2-yl)-[5-(1-isopropyl-pyrrolidin-3-yloxy)-1H-indol-2-yl]-methanone,
5-(1-isopropyl-piperidin-4-yloxy)-1H-indole-2-carboxylic acid methyl-(2-pyridin-2-yl-ethyl)-amide,
5-(1-isopropyl-piperidin-4-yloxy)-1H-indole-2-carboxylic acid ethyl-pyridin-4-ylmethyl-amide,
[5-(1-isopropyl-piperidin-4-yloxy)-1H-indol-2-yl]-((S)-2-trifluoromethyl-pyrrolidin-1-yl)-methanone,
5-(1-isopropyl-piperidin-4-yloxy)-1H-indole-2-carboxylic acid (furan-2-ylmethyl)-amide,
5-(1-isopropyl-piperidin-4-yloxy)-1H-indole-2-carboxylic acid (2-morpholin-4-yl-ethyl)-amide,
5-(1-isopropyl-piperidin-4-yloxy)-1H-indole-2-carboxylic acid (3-methoxy-propyl)-amide,
5-(1-isopropyl-piperidin-4-yloxy)-1H-indole-2-carboxylic acid (3-dimethylamino-propyl)-amide,
5-(1-isopropyl-piperidin-4-yloxy)-1H-indole-2-carboxylic acid cyclopentylamide,
5-(1-isopropyl-piperidin-4-yloxy)-1H-indole-2-carboxylic acid cyclohexylamide,
5-(1-isopropyl-piperidin-4-yloxy)-1H-indole-2-carboxylic acid (2-piperidin-1-yl-ethyl)-amide,
azetidin-1-yl-[5-(1-isopropyl-piperidin-4-yloxy)-1H-indol-2-yl]-methanone; hydrochloride,
[5-(1-isopropyl-piperidin-4-yloxy)-1H-indol-2-yl]-(3-pyridin-2-yl-pyrrolidin-1-yl)-methanone,
5-(1-isopropyl-piperidin-4-yloxy)-1H-indole-2-carboxylic acid (1-ethyl-piperidin-3-yl)-amide,
(4-isopropyl-piperazin-1-yl)-[5-(1-isopropyl-piperidin-4-yloxy)-1H-indol-2-yl]-methanone,
[5-(1-isopropyl-piperidin-4-yloxy)-1H-indol-2-yl]-(2-methyl-pyrrolidin-1-yl)-methanone,
[5-(1-isopropyl-piperidin-4-yloxy)-1H-indol-2-yl]-pyrrolidin-1-yl-methanone,
[5-(1-isopropyl-piperidin-4-yloxy)-1H-indol-2-yl]-piperidin-1-yl-methanone,

[5-(1-isopropyl-piperidin-4-yloxy)-1H-indol-2-yl]-morpholin-4-yl-methanone,
[5-(1-isopropyl-piperidin-4-yloxy)-1H-indol-2-yl]-thiomorpholin-4-yl-methanone,
5-(1-isopropyl-piperidin-4-yloxy)-1H-indole-2-carboxylic acid cyclopropylmethyl-amide,
[5-(1-isopropyl-piperidin-4-yloxy)-1H-indol-2-yl]-(4-methoxy-piperidin-1-yl)-methanone,
[5-(1-isopropyl-piperidin-4-yloxy)-1H-indol-2-yl]-(4-methyl-piperazin-1-yl)-methanone,
[5-(1-isopropyl-piperidin-4-yloxy)-1H-indol-2-yl]-(3-methoxy-piperidin-1-yl)-methanone,
(4-benzyl-piperidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid (2-methylsulfanyl-ethyl)-amide,
5-(1-isopropyl-piperidin-4-yloxy)-1H-indole-2-carboxylic acid (1-phenyl-propyl)-amide,
(4,4-difluoro-piperidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid ethyl-(2-fluoro-benzyl)-amide,
5-(1-isopropyl-piperidin-4-yloxy)-1H-indole-2-carboxylic acid 4-methyl-benzylamide,
1-[5-(1-isopropyl-piperidin-4-yloxy)-1H-indole-2-carbonyl]-piperidine-4-carboxylic acid amide,
(3,6-dihydro-2H-pyridin-1-yl)-[5-(1-isopropyl-piperidin-4-yloxy)-1H-indol-2-yl]-methanone,
[5-(1-isopropyl-piperidin-4-yloxy)-1H-indol-2-yl]-(3-methyl-piperidin-1-yl)-methanone,
5-(1-isopropyl-piperidin-4-yloxy)-1H-indole-2-carboxylic acid methyl-pyridin-3-ylmethyl-amide,
5-(1-isopropyl-piperidin-4-yloxy)-1H-indole-2-carboxylic acid [2-(2-methyl-piperidin-1-yl)-ethyl]-amide,
5-(1-isopropyl-piperidin-4-yloxy)-1H-indole-2-carboxylic acid dimethylcarbamoylmethyl-methyl-amide,
(4-hydroxymethyl-piperidin-1-yl)-[5-(1-isopropyl-piperidin-4-yloxy)-1H-indol-2-yl]-methanone,
(1,3-dihydro-isoindol-2-yl)-[5-(1-isopropyl-piperidin-4-yloxy)-1H-indol-2-yl]-methanone,
5-[2-(1-methyl-pyrrolidin-2-yl)-ethoxy]-1H-indole-2-carboxylic acid cyclopentylamide,
5-[2-(1-methyl-pyrrolidin-2-yl)-ethoxy]-1H-indole-2-carboxylic acid (2-piperidin-1-yl-ethyl)-amide,
azetidin-1-yl-{5-[2-(1-methyl-pyrrolidin-2-yl)-ethoxy]-1H-indol-2-yl}-methanone,
{5-[2-(1-methyl-pyrrolidin-2-yl)-ethoxy]-1H-indol-2-yl}-(3-pyridin-2-yl-pyrrolidin-1-yl)-methanone,
(4-isopropyl-piperazin-1-yl)-{5-[2-(1-methyl-pyrrolidin-2-yl)-ethoxy]-1H-indol-2-yl}-methanone,
(2-methyl-pyrrolidin-1-yl)-{5-[2-(1-methyl-pyrrolidin-2-yl)-ethoxy]-1H-indol-2-yl}-methanone,
{5-[2-(1-methyl-pyrrolidin-2-yl)-ethoxy]-1H-indol-2-yl}-pyrrolidin-1-yl-methanone,
{5-[2-(1-methyl-pyrrolidin-2-yl)-ethoxy]-1H-indol-2-yl}-piperidin-1-yl-methanone,
{5-[2-(1-methyl-pyrrolidin-2-yl)-ethoxy]-1H-indol-2-yl}-morpholin-4-yl-methanone,
{5-[2-(1-methyl-pyrrolidin-2-yl)-ethoxy]-1H-indol-2-yl}-thiomorpholin-4-yl-methanone,
(4-methoxy-piperidin-1-yl)-{5-[2-(1-methyl-pyrrolidin-2-yl)-ethoxy]-1H-indol-2-yl}-methanone,
(4-methyl-piperazin-1-yl)-{5-[2-(1-methyl-pyrrolidin-2-yl)-ethoxy]-1H-indol-2-yl}-methanone,
(3-methoxy-piperidin-1-yl)-{5-[2-(1-methyl-pyrrolidin-2-yl)-ethoxy]-1H-indol-2-yl}-methanone,
(4-benzyl-piperidin-1-yl)-{5-[2-(1-methyl-pyrrolidin-2-yl)-ethoxy]-1H-indol-2-yl}-methanone,
(4-hydroxy-piperidin-1-yl)-{5-[2-(1-methyl-pyrrolidin-2-yl)-ethoxy]-1H-indol-2-yl}-methanone,
(4,4-difluoro-piperidin-1-yl)-{5-[2-(1-methyl-pyrrolidin-2-yl)-ethoxy]-1H-indol-2-yl}-methanone,
(3,6-dihydro-2H-pyridin-1-yl)-{5-[2-(1-methyl-pyrrolidin-2-yl)-ethoxy]-1H-indol-2-yl}-methanone,
(3-methyl-piperidin-1-yl)-{5-[2-(1-methyl-pyrrolidin-2-yl)-ethoxy]-1H-indol-2-yl}-methanone,
(4-hydroxymethyl-piperidin-1-yl)-{5-[2-(1-methyl-pyrrolidin-2-yl)-ethoxy]-1H-indol-2-yl}-methanone,
(1,3-dihydro-isoindol-2-yl)-{5-[2-(1-methyl-pyrrolidin-2-yl)-ethoxy]-1H-indol-2-yl}-methanone,
[5-(1-isopropyl-pyrrolidin-3-yloxy)-1H-indol-2-yl]-((S)-2-trifluoromethyl-pyrrolidin-1-yl)-methanone,
{5-[2-(1-methyl-pyrrolidin-2-yl)-ethoxy]-1H-indol-2-yl}-((S)-2-trifluoromethyl-pyrrolidin-1-yl)-methanone,
[5-((S)-1-isopropyl-pyrrolidin-3-yloxy)-1H-indol-2-yl]-morpholin-4-yl-methanone,
[5-((R)-1-isopropyl-pyrrolidin-3-yloxy)-1H-indol-2-yl]-morpholin-4-yl-methanone,
[5-((S)-1-cyclopropylmethyl-pyrrolidin-3-yloxy)-1H-indol-2-yl]-morpholin-4-yl-methanone,
morpholin-4-yl-[5-((S)-1-propyl-pyrrolidin-3-yloxy)-1H-indol-2-yl]-methanone,
[6-(1-isopropyl-pyrrolidin-3-yloxy)-1H-indol-2-yl]-morpholin-4-yl-methanone,
[6-(1-isopropyl-piperidin-4-yloxy)-1H-indol-2-yl]-morpholin-4-yl-methanone,
[6-(1-isopropyl-piperidin-4-yloxy)-1H-indol-2-yl]-thiomorpholin-4-yl-methanone,
[6-(1-isopropyl-piperidin-4-yloxy)-1H-indol-2-yl]-piperidin-1-yl-methanone,
[6-(1-isopropyl-piperidin-4-yloxy)-1H-indol-2-yl]-(4-methyl-piperidin-1-yl)-methanone,
[6-(1-isopropyl-piperidin-4-yloxy)-1H-indol-2-yl]-(4-methoxy-piperidin-1-yl)-methanone,
[6-(1-isopropyl-piperidin-4-yloxy)-1H-indol-2-yl]-pyrrolidin-1-yl-methanone,
[6-(1-isopropyl-piperidin-4-yloxy)-1H-indol-2-yl]-(2-methyl-pyrrolidin-1-yl)-methanone,
azepan-1-yl-[6-(1-isopropyl-piperidin-4-yloxy)-1H-indol-2-yl]-methanone,
(2,6-dimethyl-morpholin-4-yl)-[6-(1-isopropyl-piperidin-4-yloxy)-1H-indol-2-yl]-methanone,
6-(1-isopropyl-piperidin-4-yloxy)-1H-indole-2-carboxylic acid cyclopropylmethyl-amide,
6-(1-isopropyl-piperidin-4-yloxy)-1H-indole-2-carboxylic acid 4-fluoro-benzylamide,
6-(1-isopropyl-piperidin-4-yloxy)-1H-indole-2-carboxylic acid (furan-2-ylmethyl)-amide,
azepan-1-yl-{6-[2-(1-methyl-pyrrolidin-2-yl)-ethoxy]-1H-indol-2-yl}-methanone,
{6-[2-(1-methyl-pyrrolidin-2-yl)-ethoxy]-1H-indol-2-yl}-pyrrolidin-1-yl-methanone,
[6-(1-isopropyl-pyrrolidin-3-yloxy)-1H-indol-2-yl]-thiomorpholin-4-yl-methanone,
[6-(1-isopropyl-pyrrolidin-3-yloxy)-1H-indol-2-yl]-piperidin-1-yl-methanone,
[6-(1-isopropyl-pyrrolidin-3-yloxy)-1H-indol-2-yl]-(4-methyl-piperidin-1-yl)-methanone,
[6-(1-isopropyl-pyrrolidin-3-yloxy)-1H-indol-2-yl]-(4-methoxy-piperidin-1-yl)-methanone,
[6-(1-isopropyl-pyrrolidin-3-yloxy)-1H-indol-2-yl]-pyrrolidin-1-yl-methanone, azepan-1-yl-[6-(1-isopropyl-pyrrolidin-3-yloxy)-1H-indol-2-yl]-methanone,
(2,6-dimethyl-morpholin-4-yl)-[6-(1-isopropyl-pyrrolidin-3-yloxy)-1H-indol-2-yl]-methanone,
6-(1-isopropyl-pyrrolidin-3-yloxy)-1H-indole-2-carboxylic acid cyclopropylmethyl-amide,
[5-((S)-1-isopropyl-pyrrolidin-3-yloxy) 1H-indol-2-yl]-morpholin-4-yl-methanone,
[5-fluoro-6-(1-isopropyl-piperidin-4-yloxy)-1H-indol-2-yl]-morpholin-4-yl-methanone,
[5-fluoro-6-(-isopropyl-piperidin-4-yloxy)-1H-indol-2-yl]-thiomorpholin-4-yl-methanone,
[5-fluoro-6-(1-isopropyl-piperidin-4-yloxy)-1H-indol-2-yl]-piperidin-1-yl-methanone,
[5-fluoro-6-(1-isopropyl-piperidin-4-yloxy)-1H-indol-2-yl]-(4-methyl-piperidin-1-yl)-methanone,
[5-fluoro-6(1-isopropyl-piperidin-4-yloxy)-1H-indol-2-yl]-(4-methoxy-piperidin-1-yl)-methanone,
[5-fluoro-6(1-isopropyl-piperidin-4-yloxy)-1H-indol-2-yl]-pyrrolidin-1-yl-methanone,
azepan-1-yl-[5-fluoro-6-(1-isopropyl-piperidin-4-yloxy)-1H-indol-2-yl]-methanone,
5-fluoro-6-(1-isopropyl-piperidin-4-yloxy)-1H-indole-2-carboxylic acid cyclopropyl-methyl-amide,
[1-ethyl-5-(1-isopropyl-pyrrolidin-3-yloxy)-1H-indol-2-yl]-morpholin-4-yl-methanone,
[1-isopropyl-5-(1-isopropyl-pyrrolidin-3-yloxy)-1H-indol-2-yl]-morpholin-4-yl-methanone,
(4,4-difluoro-piperidin-1-yl) [5-((S)-1-isopropyl-pyrrolidin-3-yloxy)-1H-indol-2-yl]-methanone,
(4,4-difluoro-piperidin-1-yl)-[5-((R)-1-isopropyl-pyrrolidin-3-yloxy)-1H-indol-2-yl]-methanone,
[5-((S)-1-isopropyl-pyrrolidin-3-yloxy)-1H-indol-2-yl]-pyrrolidin-1-yl-methanone,
(3,3-difluoro-piperidin-1-yl) [5-(1-isopropyl-piperidin-4-yloxy)-1H-indol-2-yl]-methanone,
(4,4-difluoro-piperidin-1-yl) [6-(3-piperidin-1-yl-propoxy)-1H-indol-2-yl]-methanone,
morpholin-4-yl-[6-(3-piperidin-1-yl-propoxy)-1H-indol-2-yl]-methanone,
(4,4-difluoro-piperidin-1-yl)-[5-fluoro-6-(3-piperidin-1-yl-propoxy)-1H-indol-2-yl]-methanone,
[5-fluoro-6-(3-piperidin-1-yl-propoxy)-1H-indol-2-yl]-morpholin-4-yl-methanone,
(4,4-difluoro-piperidin-1-yl)-[1-isopropyl-5-(1-isopropyl-piperidin-4-yloxy)-1H-indol-2-yl]-methanone,
(4,4-di fluoro-piperidin-1-yl)-[5-((-isopropyl-piperidin-4-yloxy)-1-(2-methoxy-ethyl)-1H-indol-2-yl]-methanone,
(4,4-difluoro-piperidin-1-yl)-[1-ethyl-S-(1-isopropyl-piperidin-4-yloxy)-1H-indol-2-yl]-methanone,
(4,4-difluoro-piperidin-1-yl)-[5-(1-isopropyl-piperidin-4-yloxy)-1-(2,2,2-trifluoro-ethyl)-1H-indol-2-yl]-methanone,
[1-cyclopropylmethyl-5-(1-isopropyl-piperidin-4-yloxy)-1H-indol-2-yl]-(4,4-difluoro-piperidin-1-yl)-methanone,
[5-(1-isopropyl-piperidin-4-yloxy)-1-(2,2,2-trifluoro-ethyl)-1H-indol-2-yl]-pyrrolidin-1-yl-methanone,
[5-(1-isopropyl-piperidin-4-yloxy)-1-(2,2,2-trifluoro-ethyl)-1H-indol-2-yl]-morpholin-4-yl-methanone,
(3,3-difluoro-piperidin-1-yl)-[5-(1-isopropyl-piperidin-4-yloxy)-1-(2,2,2-trifluoro-ethyl)-1H-indol-2-yl]-methanone,
(4,4-difluoro-piperidin-1-yl)-[1-(2-hydroxy-ethyl)-5-(1-isopropyl-piperidin-4-yloxy)-1H-indol-2-yl]-methanone,
(4,4-difluoro-piperidin-1-yl)-[5-(1-isopropyl-piperidin-4-yloxy)-1-methanesulfonyl-1H-indol-2-yl]-methanone,
1-[2-(4,4-difluoro-piperidine-1-carbonyl)-5-(1-isopropyl-piperidin-4-yloxy)-indol-1-yl]-ethanone,
(4,4-difluoro-piperidin-1-yl)-[5-(1-isopropyl-piperidin-4-yloxy)-1-methyl-1H-indol-2-yl]-methanone,
[5-(1-cyclopropylmethyl-piperidin-4-yloxy)-1H-indol-2-yl]-morpholin-4-yl-methanone,
[5-(1-benzyl-piperidin-4-yloxy)-1H-indol-2-yl]-morpholin-4-yl-methanone,
(4,4-difluoro-piperidin-1-yl)-{5-[3-(methyl-propyl-amino)-propoxy]-1H-indol-2-yl}-methanone as formic acid salt,
(4,4-difluoro-piperidin-1-yl)-{5-[3-(ethyl-propyl-amino)-propoxy]-1H-indol-2-yl}-methanone as formic acid salt,
(4,4-difluoro-piperidin-1-yl)-{5-[3-(isopropyl-methyl-amino)-propoxy]-1H-indol-2-yl}-methanone as formic acid salt,
(4,4-difluoro-piperidin-1-yl)-[5-(3-pyrrolidin-1-yl-propoxy)-1H-indol-2-yl]-methanone as formic acid salt,
[5-(3-azepan-1-yl-propoxy)-1H-indol-2-yl]-(4,4-difluoro-piperidin-1-yl)-methanone as formic acid salt,
(4,4-difluoro-piperidin-1-yl)-{5-[3-(3-methyl-piperidin-1-yl)-propoxy]-1H-indol-2-yl}-methanone as formic acid salt,
(4,4-difluoro-piperidin-1-yl)-{5-[3-(2,6-cis-dimethyl-piperidin-1-yl)-propoxy]-1H-indol-2-yl}-methanone as formic acid salt,
(4,4-difluoro-piperidin-1-yl)-[5-(3-thiomorpholin-4-yl-propoxy)-1H-indol-2-yl]-methanone as formic acid salt,
(4,4-difluoro-piperidin-1-yl)-{5-[3-(2,5-dihydro-pyrrol-1-yl)-propoxy]-1H-indol-2-yl}-methanone as formic acid salt,
(4,4-difluoro-piperidin-1-yl)-{5-[3-(2-methyl-pyrrolidin-1-yl)-propoxy]-1H-indol-2-yl}-methanone as formic acid salt,
(4,4-difluoro-piperidin-1-yl)-{5-[3-(2,5-cis/trans-dimethyl-pyrrolidin-1-yl)-propoxy]-1H-indol-2-yl}-methanone as formic acid salt,
(4,4-difluoro-piperidin-1-yl)-{5-[3-(3S-hydroxy-pyrrolidin-1-yl)-propoxy]-1H-indol-2-yl}-methanone as formic acid salt,
(4,4-difluoro-piperidin-1-yl)-{5-[3-(3-dimethylamino-pyrrolidin-1-yl)-propoxy]-1H-indol-2-yl}-methanone as formic acid salt,
(4,4-difluoro-piperidin-1-yl)-[5-(3-piperidin-1-yl-propoxy)-1H-indol-2-yl]-methanone,
(4,4-difluoro-piperidin-1-yl)-[5-(3-morpholin-4-yl-propoxy)-1H-indol-2-yl]-methanone,
{5-[3-(4,4-difluoro-piperidin-1-yl)-propoxy]-1H-indol-2-yl}-morpholin-4-yl-methanone,
[5-(1-cyclopropyl-piperidin-4-yloxy)-1H-indol-2-yl]-morpholin-4-yl-methanone, and pharmaceutically acceptable salts thereof.

Particularly preferred compounds of formula I of the present invention are the following:
morpholin-4-yl-[5-(3-piperidin-1-yl-propoxy)-1H-indol-2-yl]-methanone,
[5-(1-isopropyl-pyrrolidin-3-yloxy)-1H-indol-2-yl]-morpholin-4-yl-methanone,
5-(1-isopropyl-piperidin-4-yloxy)-1H-indole-2-carboxylic acid tert-butylamide,
(2,5-dihydro-pyrrol-1-yl)-[5-(1-isopropyl-piperidin-4-yloxy)-1H-indol-2-yl]-methanone,
(3-hydroxy-pyrrolidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid ethyl-(2-methoxy-ethyl)-amide, 5-(1-isopropyl-piperidin-4-yloxy)-1H-indole-2-carboxylic acid isopropyl-methyl-amide,
5-(1-isopropyl-piperidin-4-yloxy)-1H-indole-2-carboxylic acid (2-morpholin-4-yl-ethyl)-amide,
5-(1-isopropyl-piperidin-4-yloxy)-1H-indole-2-carboxylic acid (2-piperidin-1-yl-ethyl)-amide,
5-(1-isopropyl-piperidin-4-yloxy)-1H-indole-2-carboxylic acid (1-ethyl-piperidin-3-yl)-amide,
[5-(1-isopropyl-piperidin-4-yloxy)-1H-indol-2-yl]-pyrrolidin-1-yl-methanone,
[5-(1-isopropyl-piperidin-4-yloxy)-1H-indol-2-yl]-morpholin-4-yl-methanone,
[5-(1-isopropyl-piperidin-4-yloxy)-1H-indol-2-yl]-(4-methoxy-piperidin-1-yl)-methanone,
(4,4-difluoro-piperidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid [2-(2-methyl-piperidin-1-yl)-ethyl]-amide,
[5-((S)-1-isopropyl-pyrrolidin-3-yloxy)-1H-indol-2-yl]-morpholin-4-yl-methanone,
[6-(1-isopropyl-piperidin-4-yloxy)-1H-indol-2-yl]-morpholin-4-yl-methanone,
(3,3-difluoro-piperidin-1-yl)-[5-(1-isopropyl-piperidin-4-yloxy)-1H-indol-2-yl]-methanone,
(4,4-difluoro-piperidin-1-yl)-[1-isopropyl-5-(1-isopropyl-piperidin-4-yloxy)-1H-indol-2-yl]-methanone,
(4,4-difluoro-piperidin-1-yl)-[5-(1-isopropyl-piperidin-4-yloxy)-1-(2-methoxy-ethyl)-1H-indol-2-yl]-methanone,
(4,4-difluoro-piperidin-1-yl)-[5-(1-isopropyl-piperidin-4-yloxy)-1-(2,2,2-trifluoro-ethyl)-1H-indol-2-yl]-methanone,
[1-cyclopropylmethyl-5-(1-isopropyl-piperidin-4-yloxy)-1H-indol-2-yl]-(4,4-difluoro-piperidin-1-yl)-methanone,
[5-(1-isopropyl-piperidin-4-yloxy)-1-(2,2,2-trifluoro-ethyl)-1H-indol-2-yl]-morpholin-4-yl-methanone,
(4,4-difluoro-piperidin-1-yl)-[5-(1-isopropyl-piperidin-4-yloxy)-1-methanesulfonyl-1H-indol-2-yl]-methanone,
1-[2-(4,4-difluoro-piperidine-1-carbonyl)-5-(1-isopropyl-piperidin-4-yloxy)-indol-1-yl]-ethanone,
(4,4-difluoro-piperidin-1-yl)-[5-(1-isopropyl-piperidin-4-yloxy)-1-methyl-1H-indol-2-yl]-methanone,
[5-(1-cyclopropylmethyl-piperidin-4-yloxy)-1H-indol-2-yl]-morpholin-4-yl-methanone,
(4,4-difluoro-piperidin-1-yl)-[5-(3-pyrrolidin-1-yl-propoxy)-1H-indol-2-yl]-methanone as formic acid salt,
(4,4-difluoro-piperidin-1-yl)-{5-[3-(2-methyl-pyrrolidin-1-yl)-propoxy]-1H-indol-2-yl}-methanone as formic acid salt,
(4,4-difluoro-piperidin-1-yl)-[5-(3-piperidin-1-yl-propoxy)-1H-indol-2-yl]-methanone,
[5-(1-cyclopropyl-piperidin-4-yloxy)-1H-indol-2-yl]-morpholin-4-yl-methanone, and pharmaceutically acceptable salts thereof.

Especially preferred are the following compounds of formula I of the present invention:
morpholin-4-yl-[5-(3-piperidin-1-yl-propoxy)-1H-indol-2-yl]-methanone,
[5-(1-isopropyl-pyrrolidin-3-yloxy)-1H-indol-2-yl]-morpholin-4-yl-methanone,
(2,5-dihydro-pyrrol-1-yl)-[5-(1-isopropyl-piperidin-4-yloxy)-1H-indol-2-yl]-methanone,
(3-hydroxy-pyrrolidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid isopropyl-methyl-amide,
[5-(1-isopropyl-piperidin-4-yloxy)-1H-indol-2-yl]-pyrrolidin-1-yl-methanone,
[5-(1-isopropyl-piperidin-4-yloxy)-1H-indol-2-yl]-morpholin-4-yl-methanone,
[5-(1-isopropyl-piperidin-4-yloxy)-1H-indol-2-yl]-(4-methoxy-piperidin-1-yl)-methanone,
(4,4-difluoro-piperidin-1-yl)-[5-(1-isopropyl-piperidin-4-yloxy)-1H-indol-2-yl]-methanone,
[6-(1-isopropyl-piperidin-4-yloxy)-1H-indol-2-yl]-morpholin-4-yl-methanone,
(3,3-difluoro-piperidin-1-yl)-[5-(1-isopropyl-piperidin-4-yloxy)-1H-indol-2-yl]-methanone,
(4,4-difluoro-piperidin-1-yl)-[1-isopropyl-5-(1-isopropyl-piperidin-4-yloxy)-1H-indol-2-yl]-methanone,
(4,4-difluoro-piperidin-1-yl)-[5-(1-isopropyl-piperidin-4-yloxy)-1-(2,2,2-trifluoro-ethyl)-1H-indol-2-yl]-methanone,
(4,4-difluoro-piperidin-1-yl)-[5-(1-isopropyl-piperidin-4-yloxy)-1-methyl-1H-indol-2-yl]-methanone,
[5-(1-cyclopropyl-piperidin-4-yloxy)-1H-indol-2-yl]-morpholin-4-yl-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of the formula II

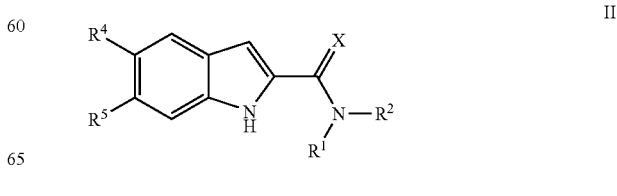

wherein X, $R^1$ and $R^2$ are as defined herein before and one of $R^4$ and $R^5$ is —OH and the other one is H, with an alcohol of the formula III HO-Het      III wherein Het is as defined herein before, in the presence of a trialkylphosphine or triphenylphosphine and of a diazo compound to obtain a compound of the formula Ia

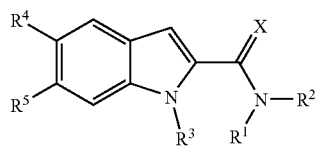

Ia wherein $R^3$ is hydrogen, and optionally alkylating this compound to obtain a compound of formula Ia'

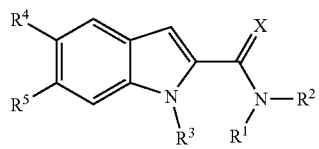

Ia' wherein $R^3$ is lower alkyl, and if desired, converting the compound obtained into a pharmaceutically acceptable acid addition salt, or alternatively, b) coupling a compound of formula IV

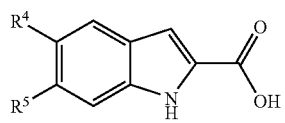

IV wherein one of $R^4$ and $R^5$ is —O-Het as defined herein before and the other one is H, with an amine of the formula V

H—$NR^1R^2$      V wherein $R^1$ and $R^2$ are as defined herein before, under basic conditions to obtain a compound of the formula Ib

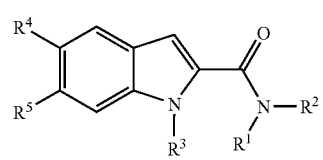

Ib wherein $R^3$ is hydrogen, and optionally alkylating this compound to obtain a compound of formula Ib'

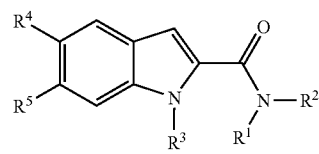

Ib' wherein $R^3$ is lower alkyl, and if desired, converting the compound obtained into a pharmaceutically acceptable acid addition salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given above unless indicated to the contrary.

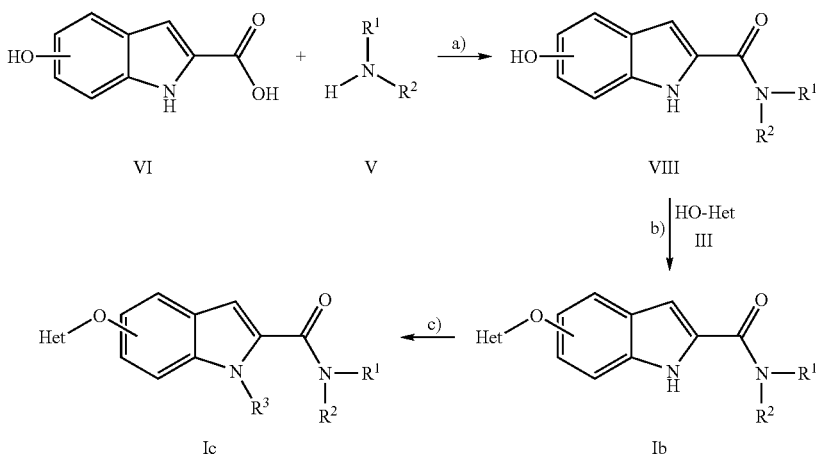

Scheme 1

Compounds of general formula I can be prepared according to scheme I as follows:

a) The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). 5-Hydroxy-indole-2-carboxylic acid IV can conveniently be transformed to the respective amide through coupling with an amine V (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethyl-carbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives VIII.

b) The syntheses of ethers are widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The transformation can be affected by employing reaction conditions which are commonly utilised in the so called "Mitsunobu reaction" which is known to those in the art and widely described (Hughes, David L. The Mitsunobu reaction. Organic Reactions (New York) (1992), 42, 335-656.). We find it convenient to couple amide VIII with alcohols HO-Het III (either commercially available or accessible by methods described in references or by methods known in the art; as appropriate) under conditions employing a phosphine like a trialkylphosphine such as tributylphosphine ($(n-Bu)_3P$), triphenylphosphine ($Ph_3P$) and the like and a diazocompound like diethyl-azodicarboxylate (DEAD), diisopropyl-azodicarboxylate (DIAD) (optionally polymer bound), tetramethyl azodicarboxamide and the like in a solvent commonly used in such transformations like tetrahydrofurane (THF), toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds Ib.

c) Compounds Ib might be the final products, however, they might optionally be subjected to a consecutive step in which the indole NH will be substituted by lower alkyl substituents through a reaction with an alkylating agent. Conditions commonly used in such types of transformation are widely described in literature and known to those in the art. The reaction might be carried out in the presence or absence of a solvent and preferably in the presence of a base. Solvents like N,N-diethyl acetamide, tetrahydrofurane (THF), diethyl ether, dioxane and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include NaH, DIPEA, $Na_2CO_3$ and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds Ic.

Alternatively, compounds of formula I can be prepared according to scheme 2 below.

Scheme 2

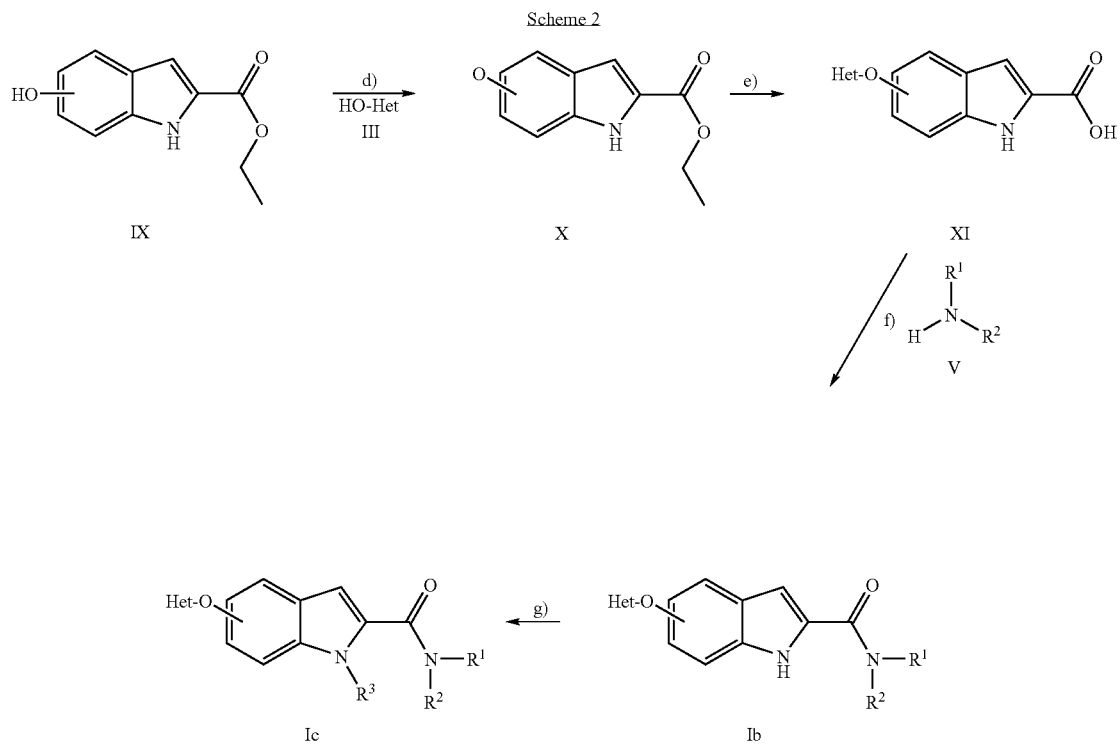

Starting from 5-hydroxy-indole-2-carboxylic acid ethyl ester compounds of formula I can be prepared as follows:

d) The ethers of formula X are prepared from 5-hydroxy-indole-2-carboxylic acid ethyl ester IX under the conditions as described above under point b) of the so called "Mitsunobu reaction".

e) The compounds of formula X are transformed into the free acids of formula XI under basic conditions, for example by using lithium hydroxide monohydrate as a base.

f) The acids of formula XI are further reacted with an amine of formula V through a amide coupling procedure under conditions as described under point a) above.

g) The indoles Ib might be the desired products, however, they might optionally be subjected to a subsequent alkylating reaction as described above under point c) to furnish the desired compounds Ic.

Alternatively, compounds of formula I can be prepared according to scheme 3 below. Exemplified is a stereospecific synthetic pathway optionally starting from enantiomerically pure starting materials synonymous shown for N-protected-3-pyrrolidinol. Starting from 5-hydroxy-indole-2-carboxylic acid ethyl ester compounds of formula I can be prepared as follows:

h) The ethers of formula XIII are prepared from 5-hydroxy-indole-2-carboxylic acid ethyl ester IX under the conditions as described above under point b) of the so called "Mitsunobu reaction" with suitably N-protected (PG=benzyl, tert-butoxycarbonyl (Boc), 9-fluorenyl-methoxycarbonyl (Fmoc) and the like; either commercially available or accessible by methods described in references or by methods known in the art; as appropriate) 3-pyrrolidinol (R or S, however also applicable for racemic, as appropriate) derivatives.

i) The compounds of formula XIII are transformed into the free acids under basic conditions, for example by using lithium hydroxide monohydrate as a base and subsequently those intermediates are coupled with amines of formula V through a amide coupling procedure under conditions as described under point a) above to furnish compounds formula XIV.

j) The N-protected indole derivatives XIV are further transformed to the respective free amine through cleavage of the PG by suitable methods for instance in case where PG=benzyl the protecting group is removed under hydrogenolytical conditions widely described in literature. Those intermediates are conveniently alkylated with a suitable alkylating reagent under basic conditions to give access to the indole derivatives Id.

k) The indoles Id might be the desired products, however, they might optionally be subjected to a subsequent alkylating reaction as described above under point c) to furnish the desired compounds Ie.

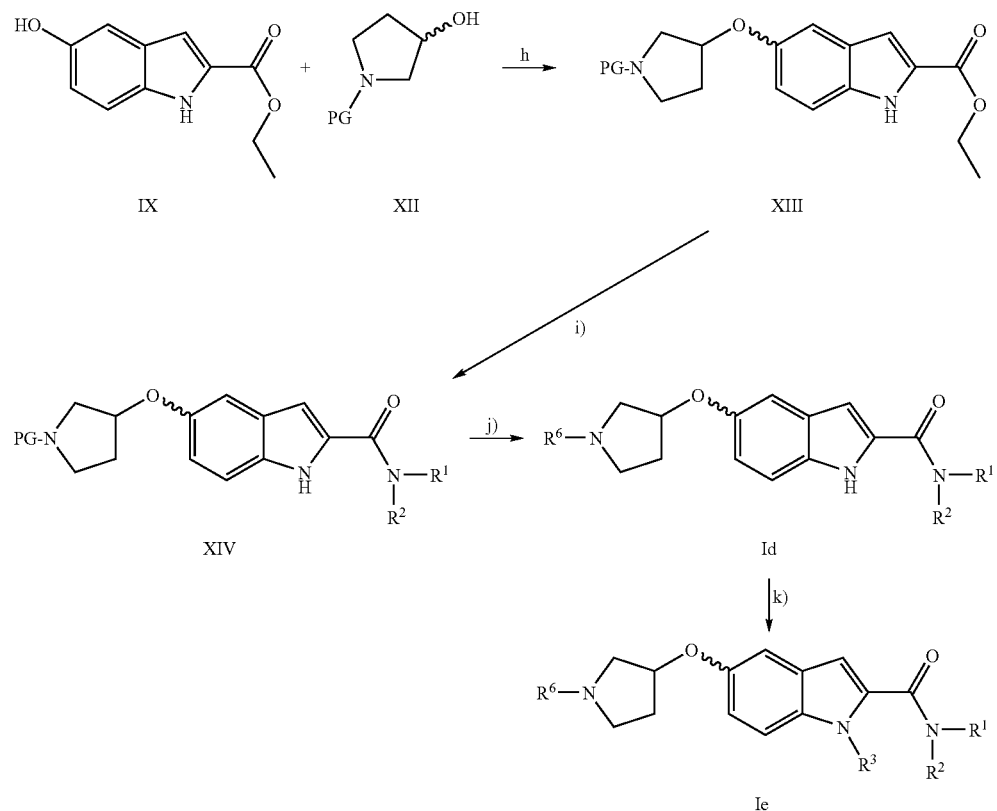
Alternatively, compounds of formula I can be prepared according to scheme 4 below.
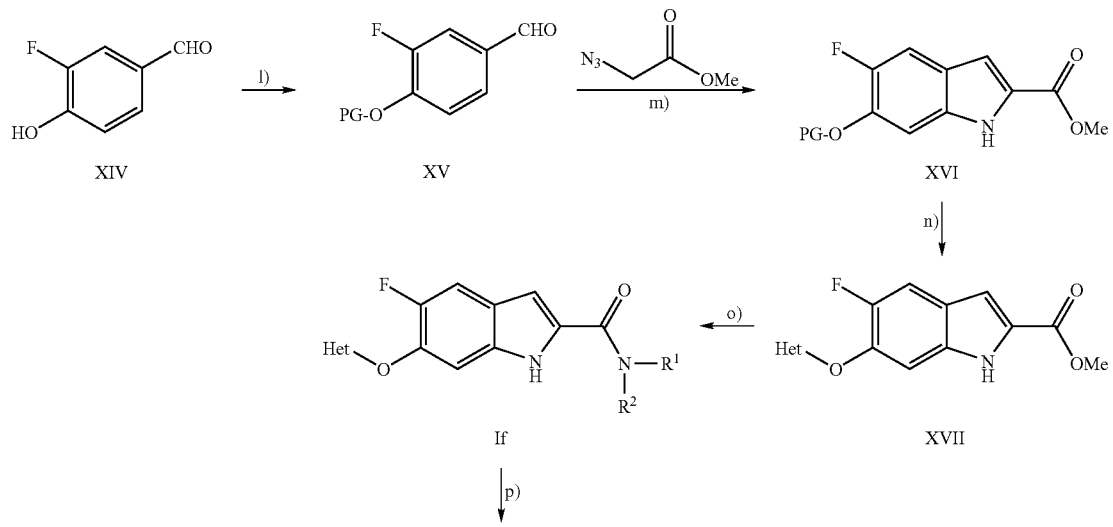

-continued

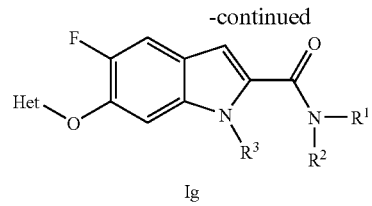

Ig l) Starting from a suitable aldehyde, 3-fluoro-4-hydroxybenzaldehyde XIV, the hydroxyl functionality is protected by a suitable group (PG=benzyl, allyl and any other group commonly used to protect hydroxy functionalities to participate adversely in any proceeding reaction sequence) to furnish aldehyde XV.

m) Aldehyde XV is conveniently transformed to the respective indole derivative XVI through reaction with methyl 2-azidoacetate (commercially available) under basic conditions and elevated temperatures (Synthesis 1985, 186-188).

n) The removal of the protecting group PG can be done depending on the nature of the protecting group and in case were PG=benzyl the reaction in most conveniently done under hydrogenolytical conditions giving access to the free alcohol which as an intermediate is subjected to a reaction as described above under point b) of the so called "Mitsunobu reaction" to give access to the indole derivative XVII.

o) The compounds of formula XVII are transformed into the free acids under basic conditions, for example by using lithium hydroxide monohydrate as a base and subsequently those intermediates are coupled with amines of formula V through a amide coupling procedure under conditions as described under point a) above to furnish compounds described by formula If.

p) The indoles If might be the desired products, however, they might optionally be subjected to a subsequent alkylating reaction as described above under point c) to furnish the desired compounds Ig.

As described above, the compounds of formula I of the present invention can be used as medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use as medicament for the treatment and/or prevention of obesity is preferred.

Further, the invention relates to compounds as defined above for use as therapeutically active substances, particularly as therapeutic active substances for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In another embodiment, the invention relates to a method for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. A method for the treatment and/or prevention of obesity is preferred.

The invention further relates to the use of compounds of formula I as defined above for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastrointestinal disorders. The use of compounds of formula I as defined above for the treatment and/or prevention of obesity is preferred.

In addition, the invention relates to the use of compounds of formula I as defined above for the preparation of medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the preparation of medicaments for the treatment and/or prevention of obesity is preferred.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

Morpholin-4-yl-[5-(3-piperidin-1-yl-propoxy)-1H-indol-2-yl]-methanone a) Step 1: (5-hydroxy-1H-indol-2-yl)-morpholin-4-yl-methanone A mixture of 1.77 g (0.01 mol) 5-hydroxy-indole-2-carboxylic acid in 25 ml DMF were cooled to 0° C. and treated with 3.53 g (0.011 mol) 2-(1H-benzotriazol-1-yl)-1,1,3,3-tetramethyl uronium tetrafluoroborat, 0.96 g (0.011 mol) morpholine and 8.6 ml (0.05 mol) N-ethyldiisopropylamine. The mixture was allowed to warm to room temperature and stirred for additional 16 h. After evaporation to dryness the residue was taken up in 75 ml ethyl acetate, 75 ml THF, 100 ml water and 50 ml 10% NaHCO$_3$ solution. The aqueous phase was extracted with 50 ml ethyl acetate and 50 ml THF. The combined organic layers were washed with 100 ml NaCl satur.aq., dried with Na$_2$SO$_4$, filtered and evaporated to dryness. The residue was suspended in 30 ml of a mixture of ethyl acetate/methanol 9/1, filtered and again suspended in 20 ml of a mixture of ethyl acetate/methanol 9/1. The residue was washed in diethyl ether and dried at 40° C. under vacuum to yield 2.04 g (83%) of the title compound as white solid. MS (m/e): 247.4 (MH$^+$, 100%).

b) Step 2: morpholin-4-yl-[5-(3-piperidin-1-yl-propoxy)-1H-indol-2-yl]-methanone A mixture of 246 mg (1 mmol) (5-hydroxy-1H-indol-2-yl)-morpholin-4-yl-methanone, 1 g (ca. 3 mmol) polymer-bound triphenylphospine (Fluka), 179 mg (1.25 mmol) piperidinepropanol and 461 mg (2 mmol) di-tert.-butyl azadicarboxylate in 20 ml THF was stirred for a prolonged period of time at room temperature. The mixture was filtered through a pad of silica and washed with 30 ml THF. The mixture was evaporated to dryness and purified on silica eluting with a gradient of DCM/2N NH$_3$ in methanol 98/2 to DCM/2N NH$_3$ in methanol 9/1. The product fractions were evaporated and the residue was titurated with diethyl ether to yield after drying at 40° C. under vacuum 47 mg (13%) of the title compound as white solid. MS (m/e): 372.4 (MH$^+$, 100%).

Example 2

[5-(1-Isopropyl-pyrrolidin-3-yloxy)-1H-indol-2-yl]-morpholin-4-yl-methanone

According to the procedure described for the synthesis of Example 1 the title compound was synthesized from (5-hydroxy-1H-indol-2-yl)-morpholin-4-yl-methanone and 1-isopropyl-pyrrolidinol which was yielded in 8% as white solid. MS (m/e): 358.1 (MH$^+$, 100%).

Example 3

(3,4-Dihydro-1H-isoguinolin-2-yl)-[5-(1-isopropyl-pyrrolidin-3-yloxy)-1H-indol-2-yl]-methanone a) Step 1: (3,4-Dihydro-1H-isoquinolin-2-yl)-(5-hydroxy-1H-indol-2-yl)-methanone According to the procedure described for the synthesis of Example 1/step 1 (3,4-dihydro-1H-isoquinolin-2-yl)-(5-hydroxy-1H-indol-2-yl)-methanone was synthesized from 5-hydroxy-indole-2-carboxylic acid and 1,2,3,4-tetrahydro-isoquinoline which was yielded in 72% as white solid. MS (m/e): 293.0 (MH$^+$, 100%).

b) Step 2: (3,4-dihydro-1H-isoquinolin-2-yl)-[5-(1-isopropyl-pyrrolidin-3-yloxy)-1H-indol-2-yl]-methanone According to the procedure described for the synthesis of Example 1/step 2 the title compound was synthesized from (3,4-dihydro-1H-isoquinolin-2-yl)-(5-hydroxy-1H-indol-2-yl)-methanone and 1-isopropyl-pyrrolidinol which was yielded in 28% as white solid. MS (m/e): 404.5 (MH$^+$, 100%).

Example 4

(3,4-Dihydro-1H-isoguinolin-2-yl)-{5-[2-(1-methyl-pyrrolidin-2-yl)-ethoxy]-1H-indol-2-yl}-methanone According to the procedure described for the synthesis of Example 1 the title compound was synthesized from (3,4-dihydro-1H-isoquinolin-2-yl)-(5-hydroxy-1H-indol-2-yl)-methanone and 1-methyl-2-pyrrolidineethanol (commercially available) which was yielded in 3% as white solid. MS (m/e): 404.5 (MH$^+$, 100%).

Example 5

5-(1-Isopropyl-pyrrolidin-3-yloxy)-1H-indole-2-carboxylic acid cyclopropylmethyl-propyl-amide a) Step 1: 5-(1-isopropyl-pyrrolidin-3-yloxy)-1H-indole-2-carboxylic acid ethyl ester A mixture of 3.08 g (15 mmol) 5-hydroxy-1H-indole-2-carboxylic acid ethyl ester, 2.51 g (20 mmol) 1-isopropyl-3-pyrrolidinol and 8.7 ml (30 mmol) tri-N-butyl phosphine in 75 ml was treated at room temperature with 7.57 g (30 mmol) 1,1'-(azodicarbonyl)-dipiperidine in 75 ml THF. The mixture was allowed to stir for a prolonged period of time and subsequently evaporated to dryness. The residue was suspended in 40 ml DCM/n-heptane 1/1, filtered and again washed with 40 ml DCM/n-heptane 1/1. The filtrate was evaporated and purified on silica eluting with a gradient of DCM/2N NH$_3$ in methanol 99/1 to DCM/2N NH$_3$ in methanol 93/7. The product fractions were evaporated and the residue was titurated with diethyl ether to yield after filtration, washing and drying of the residue at 50° C. under vacuum 2.1 g (44%) of the title compound as off-white solid. MS (m/e): 317.1 (MH$^+$, 100%).

b) Step 2: 5-(1-isopropyl-pyrrolidin-3-yloxy)-1H-indole-2-carboxylic acid

A mixture of 2.05 g (6 mmol) 5-(1-Isopropyl-pyrrolidin-3-yloxy)-1H-indole-2-carboxylic acid ethyl ester and 0.299 g (7 mmol) lithiumhydroxide monohydrate 30 ml THF, 30 ml methanol and 15 ml water was heated to 100° C. for 2 h. The organic solvents were removed and aq. 1N HCl was added to adjust the pH of the solution to 2-3. Subsequently, the mixture was evaporated to dryness and the mixture was used without further purification in the next step. MS (m/e): 289.1 (MH$^+$, 100%).

c) Step 3: 5-(1-Isopropyl-pyrrolidin-3-yloxy)-1H-indole-2-carboxylic acid cyclopropylmethyl-propyl-amide A mixture of 0.07 mmol 5-(1-isopropyl-pyrrolidin-3-yloxy)-1H-indole-2-carboxylic acid, 1.25 equiv. 2-(1H-benzotriazol-1-yl)-1,1,3,3-tetramethyl uronium tetrafluoroborat, 1.25 equivalents cyclopropylmethyl-propyl-amine and 5 equivalents N-ethyldiisopropyl-amine in 0.7 ml DMF was stirred for 16 h at room temperature. The mixture was diluted with 0.8 ml methanol and subjected to preparative HPLC purification on reversed phase material eluting with a gradient of acetonitrile/water/triethyamine. The product fractions were evaporated to dryness to yield 9.1 mg (37%) of the title compound as light brown solid. MS (m/e): 384.5 (MH$^+$, 100%).

Intermediate 1

5-(1-Isopropyl-piperidin-4-yloxy)-1H-indole-2-carboxylic acid

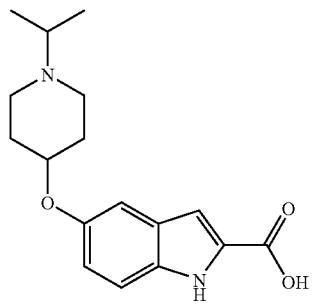

a) Step 1: 5-(1-isopropyl-piperidin-4-yloxy)-1H-indole-2-carboxylic acid ethyl ester According to the procedure described for the synthesis of Example 5/step 1 5-(1-isopropyl-piperidin-4-yloxy)-1H-indole-2-carboxylic acid ethyl ester was synthesized from 5-hydroxy-1H-indole-2-carboxylic acid ethyl ester (commercially available) and 1-isopropyl-piperidin-4-ol (commercially available). The title compound was yielded in 33% as off-white solid. MS (m/e): 331.1 (MH$^+$, 100%).

b) Step 2: 5-(1-Isopropyl-piperidin-4-yloxy)-1H-indole-2-carboxylic acid

According to the procedure described for the synthesis of Example 5/step 2 5-(1-isopropyl-piperidin-4-yloxy)-1H-indole-2-carboxylic acid was synthesized from 5-(1-isopropyl-piperidin-4-yloxy)-1H-indole-2-carboxylic acid ethyl ester with lithium hydroxide monohydrate. The title compound was yielded as light brown foam and used without further purification. MS (m/e): 303.1 (MH$^+$, 100%).

Intermediate 2

5-[2-(1-Methyl-pyrrolidin-2-yl)-ethoxy]-1H-indole-2-carboxylic acid

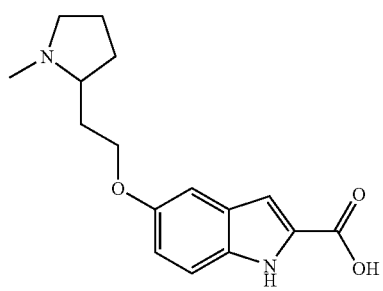

a) Step 1: 5-[2-(1-methyl-pyrrolidin-2-yl)-ethoxy]-1H-indole-2-carboxylic acid ethyl ester According to the procedure described for the synthesis of Example 5/step 1 5-[2-(1-methyl-pyrrolidin-2-yl)-ethoxy]-1H-indole-2-carboxylic acid ethyl ester was synthesized from 5-hydroxy-1H-indole-2-carboxylic acid ethyl ester (commercially available) and 2-(1-methyl-pyrrolidin-2-yl)-ethanol (commercially available). The title compound was yielded in 38% as light brown foam. MS (m/e): 317.1 (MH$^+$, 100%).

b) Step 2: 5-[2-(1-methyl-pyrrolidin-2-yl)-ethoxy]-1H-indole-2-carboxylic acid

According to the procedure described for the synthesis of Example 5/step 2 5-[2-(1-methyl-pyrrolidin-2-yl)-ethoxy]-1H-indole-2-carboxylic acid was synthesized from 5-[2-(1-methyl-pyrrolidin-2-yl)-ethoxy]-1H-indole-2-carboxylic acid ethyl ester with lithium hydroxide monohydrate. The title compound was yielded as white solid and used without further purification. MS (m/e): 289.1 (MH$^+$, 100%).

According to the procedure described for the synthesis of Example 5 further indole derivatives have been synthesized from 5-[2-(1-methyl-pyrrolidin-2-yl)-ethoxy]-1H-indole-2-carboxylic acid, 5-(1-isopropyl-piperidin-4-yloxy)-1H-indole-2-carboxylic acid or 5-(1-isopropyl-pyrrolidin-3-yloxy)-1H-indole-2-carboxylic acid respectively through the coupling procedure described for Example 5/step 3 with the respective amine mentioned in table 1. For some of the examples the purification procedure has been adapted due to precipitation of the respective compound from the respective mixture. In those cases the tide compound was filtered off, washed with methanol (containing HCL in case of example 85) and diethyl ether and dried. The results are shown in Table 1 and comprise Example 6 to Example 134.

TABLE 1

| Ex. No | Systematic name | MW | Starting materials | MW found $(M + H)^+$ |
|---|---|---|---|---|
| 6 | 5-(1-Isopropyl-pyrrolidin-3-yloxy)-1H-indole-2-carboxylic acid diethylamide | 343.5 | 5-(1-Isopropyl-pyrrolidin-3-yloxy)-1H-indole-2-carboxylic acid (Example 5/step 2) and diethylamine (commercially available) | 344.3 |
| 7 | 5-(1-Isopropyl-pyrrolidin-3-yloxy)-1H-indole-2-carboxylic acid ethyl-methyl-amide | 329.4 | 5-(1-Isopropyl-pyrrolidin-3-yloxy)-1H-indole-2-carboxylic acid (Example 5/step 2) and ethyl-methyl-amine (commercially available) | 330.3 |
| 8 | 5-(1-Isopropyl-pyrrolidin-3-yloxy)-1H-indole-2-carboxylic acid methyl-propyl-amide | 343.5 | 5-(1-Isopropyl-pyrrolidin-3-yloxy)-1H-indole-2-carboxylic acid (Example 5/step 2) and methyl-propyl-amine (commercially available) | 344.3 |
| 9 | (2,6-Dimethyl-morpholin-4-yl)-[5-(1-isopropyl-pyrrolidin-3-yloxy)-1H-indol-2-yl]-methanone | 385.5 | 5-(1-Isopropyl-pyrrolidin-3-yloxy)-1H-indole-2-carboxylic acid (Example 5/step 2) and 2,6-Dimethyl-morpholine (commercially available) | 386.5 |
| 10 | 5-(1-Isopropyl-pyrrolidin-3-yloxy)-1H-indole-2-carboxylic acid methyl-phenethyl-amide | 405.5 | 5-(1-Isopropyl-pyrrolidin-3-yloxy)-1H-indole-2-carboxylic acid (Example 5/step 2) and methyl-phenethyl-amine (commercially available) | 406.5 |
| 11 | (2,5-Dihydro-pyrrol-1-yl)-[5-(1-isopropyl-pyrrolidin-3-yloxy)-1H-indol-2-yl]-methanone | 339.4 | 5-(1-Isopropyl-pyrrolidin-3-yloxy)-1H-indole-2-carboxylic acid (Example 5/step 2) and 2,5-Dihydro-pyrrol (commercially available) | 340.4 |
| 12 | 5-(1-Isopropyl-pyrrolidin-3-yloxy)-1H-indole-2-carboxylic acid cyclohexyl-methyl-amide | 383.5 | 5-(1-Isopropyl-pyrrolidin-3-yloxy)-1H-indole-2-carboxylic acid (Example 5/step 2) and cyclohexyl-methyl-amide (commercially available) | 384.4 |
| 13 | (3-Hydroxy-pyrrolidin-1-yl)-[5-(1-isopropyl-pyrrolidin-3-yloxy)-1H-indol-2-yl]-methanone | 357.5 | 5-(1-Isopropyl-pyrrolidin-3-yloxy)-1H-indole-2-carboxylic acid (Example 5/step 2) and 3-Hydroxy-pyrrolidin (commercially available) | 358.3 |
| 14 | Azepan-1-yl-[5-(1-isopropyl-pyrrolidin-3-yloxy)-1H-indol-2-yl]-methanone | 369.5 | 5-(1-Isopropyl-pyrrolidin-3-yloxy)-1H-indole-2-carboxylic acid (Example 5/step 2) and azepan (commercially available) | 370.3 |
| 15 | [5-(1-Isopropyl-pyrrolidin-3-yloxy)-1H-indol-2-yl]-(4-methyl-piperidin-1-yl)-methanone | 369.5 | 5-(1-Isopropyl-pyrrolidin-3-yloxy)-1H-indole-2-carboxylic acid (Example 5/step 2) and 4-methyl-piperidine (commercially available) | 370.3 |
| 16 | 5-(1-Isopropyl-pyrrolidin-3-yloxy)-1H-indole-2-carboxylic acid isopropyl-methyl-amide | 343.5 | 5-(1-Isopropyl-pyrrolidin-3-yloxy)-1H-indole-2-carboxylic acid (Example 5/step 2) and isopropyl-methyl-amine (commercially available) | 344.3 |
| 17 | 5-(1-Isopropyl-pyrrolidin-3-yloxy)-1H-indole-2-carboxylic acid isobutyl-amide | 343.5 | 5-(1-Isopropyl-pyrrolidin-3-yloxy)-1H-indole-2-carboxylic acid (Example 5/step 2) and isobutyl-amine (commercially available) | 344.3 |
| 18 | [5-(1-Isopropyl-pyrrolidin-3-yloxy)-1H-indol-2-yl]-(2-methyl-piperidin-1-yl)-methanone | 369.5 | 5-(1-Isopropyl-pyrrolidin-3-yloxy)-1H-indole-2-carboxylic acid (Example 5/step 2) and 2-methyl-piperidine (commercially available) | 370.3 |
| 19 | 5-(1-Isopropyl-piperidin-4-yloxy)-1H-indole-2-carboxylic acid cyclopropylmethyl-propyl-amide | 397.6 | 5-(1-Isopropyl-piperidin-4-yloxy)-1H-indole-2-carboxylic acid (intermediate 1) and cyclopropylmethyl-propyl-amide (commercially available) | 398.5 |

TABLE 1-continued

| Ex. No | Systematic name | MW | Starting materials | MW found $(M + H)^+$ |
|---|---|---|---|---|
| 20 | 5-(1-Isopropyl-piperidin-4-yloxy)-1H-indole-2-carboxylic acid diethylamide | 357.5 | 5-(1-Isopropyl-piperidin-4-yloxy)-1H-indole-2-carboxylic acid (intermediate 1) and diethylamine (commercially available) | 358.5 |
| 21 | 5-(1-Isopropyl-piperidin-4-yloxy)-1H-indole-2-carboxylic acid isopropylamide | 343.5 | 5-(1-Isopropyl-piperidin-4-yloxy)-1H-indole-2-carboxylic acid (intermediate 1) and isopropylamine (commercially available) | 344.1 |
| 22 | 5-(1-Isopropyl-piperidin-4-yloxy)-1H-indole-2-carboxylic acid tert-butylamide | 357.5 | 5-(1-Isopropyl-piperidin-4-yloxy)-1H-indole-2-carboxylic acid (intermediate 1) and tert-butylamine (commercially available) | 358.4 |
| 23 | 5-(1-Isopropyl-piperidin-4-yloxy)-1H-indole-2-carboxylic acid cyclopropylamine | 341.5 | 5-(1-Isopropyl-piperidin-4-yloxy)-1H-indole-2-carboxylic acid (intermediate 1) and cyclopropylamine (commercially available) | 342.3 |
| 24 | 5-(1-Isopropyl-piperidin-4-yloxy)-1H-indole-2-carboxylic acid ethyl-methyl-amide | 343.5 | 5-(1-Isopropyl-piperidin-4-yloxy)-1H-indole-2-carboxylic acid (intermediate 1) and ethyl-methyl-amine (commercially available) | 344.3 |
| 25 | 5-(1-Isopropyl-piperidin-4-yloxy)-1H-indole-2-carboxylic acid propylamide | 343.5 | 5-(1-Isopropyl-piperidin-4-yloxy)-1H-indole-2-carboxylic acid (intermediate 1) and propylamine (commercially available) | 344.4 |
| 26 | 5-(1-Isopropyl-piperidin-4-yloxy)-1H-indole-2-carboxylic acid methyl-propyl-amide | 357.5 | 5-(1-Isopropyl-piperidin-4-yloxy)-1H-indole-2-carboxylic acid (intermediate 1) and methyl-propyl-amine (commercially available) | 358.4 |
| 27 | 5-(1-Isopropyl-piperidin-4-yloxy)-1H-indole-2-carboxylic acid allylamide | 341.5 | 5-(1-Isopropyl-piperidin-4-yloxy)-1H-indole-2-carboxylic acid (intermediate 1) and allylamine (commercially available) | 342.1 |
| 28 | 5-(1-Isopropyl-piperidin-4-yloxy)-1H-indole-2-carboxylic acid prop-2-ynylamide | 339.4 | 5-(1-Isopropyl-piperidin-4-yloxy)-1H-indole-2-carboxylic acid (intermediate 1) and prop-2-ynylamine (commercially available) | 340.4 |
| 29 | (2,6-Dimethyl-morpholin-4-yl)-[5-(1-isopropyl-piperidin-4-yloxy)-1H-indol-2-yl]-methanone | 399.5 | 5-(1-Isopropyl-piperidin-4-yloxy)-1H-indole-2-carboxylic acid (intermediate 1) and 2,6-Dimethyl-morpholine (commercially available) | 400.6 |
| 30 | 5-(1-Isopropyl-piperidin-4-yloxy)-1H-indole-2-carboxylic acid methyl-phenethyl-amide | 419.6 | 5-(1-Isopropyl-piperidin-4-yloxy)-1H-indole-2-carboxylic acid (intermediate 1) and methyl-phenethyl-amine (commercially available) | 420.4 |
| 31 | (2,5-Dihydro-pyrrol-1-yl)-[5-(1-isopropyl-piperidin-4-yloxy)-1H-indol-2-yl]-methanone | 353.5 | 5-(1-Isopropyl-piperidin-4-yloxy)-1H-indole-2-carboxylic acid (intermediate 1) and 2,5-Dihydro-pyrrol (commercially available) | 354.3 |
| 32 | 5-(1-Isopropyl-piperidin-4-yloxy)-1H-indole-2-carboxylic acid cyclohexyl-methyl-amide | 397.6 | 5-(1-Isopropyl-piperidn-4-yloxy)-1H-indole-2-carboxylic acid (intermediate 1) and cyclohexyl-methyl-amine (commercially available) | 398.5 |
| 33 | (3-Hydroxy-pyrrolidin-1-yl)-[5-(1-isopropyl-piperidin-4-yloxy)-1H-indol-2-yl]-methanone | 371.5 | 5-(1-Isopropyl-piperidin-4-yloxy)-1H-indole-2-carboxylic acid (intermediate 1) and 3-Hydroxy-pyrrolidin (commercially available) | 372.4 |
| 34 | Azepan-1-yl-[5-(1-isopropyl-piperidin-4-yloxy)-1H-indol-2-yl]-methanone | 383.5 | 5-(1-Isopropyl-piperidin-4-yloxy)-1H-indole-2-carboxylic acid (intermediate 1) and azepan (commercially available) | 384.5 |

TABLE 1-continued

| Ex. No | Systematic name | MW | Starting materials | MW found $(M + H)^+$ |
|---|---|---|---|---|
| 35 | 5-(1-Isopropyl-piperidin-4-yloxy)-1H-indole-2-carboxylic acid ethyl-(2-methoxy-ethyl)-amide | 387.5 | 5-(1-Isopropyl-piperidin-4-yloxy)-1H-indole-2-carboxylic acid (intermediate 1) and 2-methoxy-ethyl-amine (commercially available) | 388.5 |
| 36 | [5-(1-Isopropyl-piperidin-4-yloxy)-1H-indol-2-yl]-(4-methyl-piperidin-1-yl)-methanone | 383.5 | 5-(1-Isopropyl-piperidin-4-yloxy)-1H-indole-2-carboxylic acid (intermediate 1) and 4-methyl-piperidine (commercially available) | 384.4 |
| 37 | 5-(1-Isopropyl-piperidin-4-yloxy)-1H-indole-2-carboxylic acid isopropyl-methyl-amide | 357.5 | 5-(1-Isopropyl-piperidin-4-yloxy)-1H-indole-2-carboxylic acid (intermediate 1) and isopropyl-methyl-amine (commercially available) | 358.3 |
| 38 | 5-(1-Isopropyl-piperidin-4-yloxy)-1H-indole-2-carboxylic acid isobutyl-amide | 357.5 | 5-(1-Isopropyl-piperidin-4-yloxy)-1H-indole-2-carboxylic acid (intermediate 1) and isobutyl-amine (commercially available) | 358.4 |
| 39 | [5-(1-Isopropyl-piperidin-4-yloxy)-1H-indol-2-yl]-(2-methyl-piperidin-1-yl)-methanone | 383.5 | 5-(1-Isopropyl-piperidin-4-yloxy)-1H-indole-2-carboxylic acid (intermediate 1) and 2-methyl-piperidin (commercially available) | 384.5 |
| 40 | (4-Benzyl-piperazin-1-yl)-[5-(1-isopropyl-piperidin-4-yloxy)-1H-indol-2-yl]-methanone | 460.6 | 5-(1-Isopropyl-piperidin-4-yloxy)-1H-indole-2-carboxylic acid (intermediate 1) and 4-Benzyl-piperazine (commercially available) | 461.5 |
| 41 | 5-[2-(1-Methyl-pyrrolidin-2-yl)-ethoxy]-1H-indole-2-carboxylic acid cyclopropylmethyl-propyl-amide | 383.5 | 5-[2-(1-Methyl-pyrrolidin-2-yl)-ethoxy]-1H-indole-2-carboxylic acid (intermediate 2) and cyclopropylmethyl-propyl-amine (commercially available) | 384.5 |
| 42 | 5-[2-(1-Methyl-pyrrolidin-2-yl)-ethoxy]-1H-indole-2-carboxylic acid diethylamide | 343.5 | 5-[2-(1-Methyl-pyrrolidin-2-yl-ethoxy]-1H-indole-2-carboxylic acid (intermediate 2) and diethylamine (commercially available) | 344.0 |
| 43 | 5-[2-(1-Methyl-pyrrolidin-2-yl)-ethoxy]-1H-indole-2-carboxylic acid isopropylamide | 329.4 | 5-[2-(1-Methyl-pyrrolidin-2-yl)-ethoxy]-1H-indole-2-carboxylic acid (intermediate 2) and isopropylamine (commercially available) | 330.4 |
| 44 | 5-[2-(1-Methyl-pyrrolidin-2-yl)-ethoxy]-1H-indole-2-carboxylic acid tert-butylamide | 343.5 | 5-[2-(1-Methyl-pyrrolidin-2-yl)-ethoxy]-1H-indole-2-carboxylic acid (intermediate 2) and tert-butylamide (commercially available) | 344.4 |
| 45 | 5-[2-(1-Methyl-pyrrolidin-2-yl)-ethoxy]-1H-indole-2-carboxylic acid ethyl-methyl-amide | 329.4 | 5-[2-(1-Methyl-pyrrolidin-2-yl)-ethoxy]-1H-indole-2-carboxylic acid (intermediate 2) and ethyl-methyl-amine (commercially available) | 330.4 |
| 46 | 5-[2-(1-Methyl-pyrrolidin-2-yl)-ethoxy]-1H-indole-2-carboxylic acid methyl-propyl-amide | 343.5 | 5-[2-(1-Methyl-pyrrolidin-2-yl)-ethoxy]-1H-indole-2-carboxylic acid (intermediate 2) and methyl-propyl-amine (commercially available) | 344.3 |
| 47 | (2,6-Dimethyl-morpholin-4-yl)-{5-[2-(1-methyl-pyrrolidin-2-yl)-ethoxy]-1H-indol-2-yl}-methanone | 385.5 | 5-[2-(1-Methyl-pyrrolidin-2-yl)-ethoxy]-1H-indole-2-carboxylic acid (intermediate 2) and 2,6-Dimethyl-morpholine (commercially available) | 386.5 |

TABLE 1-continued

| Ex. No | Systematic name | MW | Starting materials | MW found $(M + H)^+$ |
|---|---|---|---|---|
| 48 | 5-[2-(1-Methyl-pyrrolidin-2-yl)-ethoxy]-1H-indole-2-carboxylic acid methyl-phenethyl-amide | 405.5 | 5-[2-(1-Methyl-pyrrolidin-2-yl)-ethoxy]-1H-indole-2-carboxylic acid (intermediate 2) and methyl-phenethyl-amine (commercially available) | 406.5 |
| 49 | (2,5-Dihydro-pyrrol-1-yl)-{5-[2-(1-methyl-pyrrolidin-2-yl)-ethoxy]-1H-indol-2-yl}-methanone | 339.4 | 5-[2-(1-Methyl-pyrrolidin-2-yl)-ethoxy]-1H-indole-2-carboxylic acid (intermediate 2) and 2,5-Dihydro-pyrrol (commercially available) | 340.3 |
| 50 | 5-[2-(1-Methyl-pyrrolidin-2-yl)-ethoxy]-1H-indole-2-carboxylic acid cyclohexyl-methyl-amide | 383.5 | 5-[2-(1-Methyl-pyrrolidin-2-yl)-ethoxy]-1H-indole-2-carboxylic acid (intermediate 2) and cyclohexyl-methyl-amine (commercially available) | 384.5 |
| 51 | (3-Hydroxy-pyrrolidin-1-yl)-{5-[2-(1-methyl-pyrrolidin-2-yl)-ethoxy]-1H-indol-2-yl}-methanone | 357.5 | 5-[2-(1-Methyl-pyrrolidin-2-yl)-ethoxy]-1H-indole-2-carboxylic acid (intermediate 2) and 3-Hydroxy-pyrrolidin (commercially available) | 358.3 |
| 52 | Azepan-1-yl-{5-[2-(1-methyl-pyrrolidin-2-yl)-ethoxy]-1H-indol-2-yl}-methanone | 369.5 | 5-[2-(1-Methyl-pyrrolidin-2-yl)-ethoxy]-1H-indole-2-carboxylic acid (intermediate 2) and azepane (commercially available) | 370.3 |
| 53 | (4-Methyl-piperidin-1-yl)-{5-[2-(1-methyl-pyrrolidin-2-yl)-ethoxy]-1H-indol-2-yl}-methanone | 369.5 | 5-[2-(1-Methyl-pyrrolidin-2-yl)-ethoxy]-1H-indole-2-carboxylic acid (intermediate 2) and 4-Methyl-piperidin (commercially available) | 370.3 |
| 54 | 5-[2-(1-Methyl-pyrrolidin-2-yl)-ethoxy]-1H-indole-2-carboxylic acid isopropyl-methyl-amide | 343.5 | 5-[2-(1-Methyl-pyrrolidin-2-yl)-ethoxy]-1H-indole-2-carboxylic acid (intermediate 2) and isopropyl-methyl-amine (commercially available) | 344.3 |
| 55 | (2-Methyl-piperidin-1-yl)-{5-[2-(1-methyl-pyrrolidin-2-yl)-ethoxy]-1H-indol-2-yl}-methanone | 369.5 | 5-[2-(1-Methyl-pyrrolidin-2-yl)-ethoxy]-1H-indole-2-carboxylic acid (intermediate 2) and 2-methyl-piperidine (commercially available) | 370.3 |
| 56 | 5-(1-Isopropyl-pyrrolidin-3-yloxy)-1H-indole-2-carboxylic acid methyl-(2-pyridin-2-yl-ethyl)-amide | 406.5 | 5-(1-Isopropyl-pyrrolidin-3-yloxy)-1H-indole-2-carboxylic acid (Example 5/step 2) and 2-pyridin-2-yl-ethyl-amide (commercially available) | 407.5 |
| 57 | 5-(1-Isopropyl-pyrrolidin-3-yloxy)-1H-indole-2-carboxylic acid cyclohexylamide | 369.5 | 5-(1-Isopropyl-pyrrolidin-3-yloxy)-1H-indole-2-carboxylic acid (Example 5/step 2) and cyclohexylamine (commercially available) | 370.3 |
| 58 | 5-(1-Isopropyl-pyrrolidin-3-yloxy)-1H-indole-2-carboxylic acid (2-piperidin-1-yl-ethyl)-amide | 398.5 | 5-(1-Isopropyl-pyrrolidin-3-yloxy)-1H-indole-2-carboxylic acid (Example 5/step 2) and 2-piperidin-1-yl-ethyl-amine (commercially available) | 399.5 |
| 59 | Azetidin-1-yl-[5-(1-isopropyl-pyrrolidin-3-yloxy)-1H-indol-2-yl]-methanone | 327.4 | 5-(1-Isopropyl-pyrrolidin-3-yloxy)-1H-indole-2-carboxylic acid (Example 5/step 2) and azetidine (commercially available) | 328.3 |
| 60 | (4-Isopropyl-piperazin-1-yl)-[5-(1-isopropyl-pyrrolidin-3-yloxy)-1H-indol-2-yl]-methanone | 398.5 | 5-(1-Isopropyl-pyrrolidin-3-yloxy)-1H-indole-2-carboxylic acid (Example 5/step 2) and 4-isopropyl-piperazine (commercially available) | 399.5 |

TABLE 1-continued

| Ex. No | Systematic name | MW | Starting materials | MW found (M + H)+ |
|---|---|---|---|---|
| 61 | [5-(1-Isopropyl-pyrrolidin-3-yloxy)-1H-indol-2-yl]-(2-methyl-pyrrolidin-1-yl)-methanone | 355.5 | 5-(1-Isopropyl-pyrrolidin-3-yloxy)-1H-indole-2-carboxylic acid (Example 5/step 2) and 2-methyl-pyrrolidine (commercially available) | 356.4 |
| 62 | [5-(1-Isopropyl-pyrrolidin-3-yloxy)-1H-indol-2-yl]-pyrrolidin-1-yl-methanone | 341.5 | 5-(1-Isopropyl-pyrrolidin-3-yloxy)-1H-indole-2-carboxylic acid (Example 5/step 2) and pyrrolidine (commercially available) | 342.2 |
| 63 | [5-(1-Isopropyl-pyrrolidin-3-yloxy)-1H-indol-2-yl]-piperidin-1-yl-methanone | 355.5 | 5-(1-Isopropyl-pyrrolidin-3-yloxy)-1H-indole-2-carboxylic acid (Example 5/step 2) and piperidine (commercially available) | 356.4 |
| 64 | [5-(1-Isopropyl-pyrrolidin-3-yloxy)-1H-indol-2-yl]-thiomorpholin-4-yl-methanone | 373.5 | 5-(1-Isopropyl-pyrrolidin-3-yloxy)-1H-indole-2-carboxylic acid (Example 5/step 2) and thiomorpholine (commercially available) | 374.4 |
| 65 | [5-(1-Isopropyl-pyrrolidin-3-yloxy)-1H-indol-2-yl]-(4-methoxy-piperidin-1-yl)-methanone | 385.5 | 5-(1-Isopropyl-pyrrolidin-3-yloxy)-1H-indole-2-carboxylic acid (Example 5/step 2) and 4-methoxy-piperidine (commercially available) | 386.4 |
| 66 | [5-(1-Isopropyl-pyrrolidin-3-yloxy)-1H-indol-2-yl]-(4-methyl-piperazin-1-yl)-methanone | 370.5 | 5-(1-Isopropyl-pyrrolidin-3-yloxy)-1H-indole-2-carboxylic acid (Example 5/step 2) and 4-methyl-piperazine (commercially available) | 371.3 |
| 67 | (4-Benzyl-piperidin-1-yl)-[5-(1-isopropyl-pyrrolidin-3-yloxy)-1H-indol-2-yl]-methanone | 445.6 | 5-(1-Isopropyl-pyrrolidin-3-yloxy)-1H-indole-2-carboxylic acid (Example 5/step 2) and 4-benzyl-piperidine (commercially available) | 446.3 |
| 68 | (4,4-Difluoro-piperidin-1-yl)-[5-(1-isoproyl-pyrrolidin-3-yloxy)-1H-indol-2-yl]-methanone | 391.5 | 5-(1-Isopropyl-pyrrolidin-3-yloxy)-1H-indole-2-carboxylic acid (Example 5/step 2) and 4,4-difluoro-piperidine (commercially available) | 392.2 |
| 69 | (3,6-Dihydro-2H-pyridin-1-yl)-[5-(1-isopropyl-pyrrolidin-3-yloxy)-1H-indol-2-yl]-methanone | 353.5 | 5-(1-Isopropyl-pyrrolidin-3-yloxy)-1H-indole-2-carboxylic acid (Example 5/step 2) and 3,6-dihydro-2H-pyridine (commercially available) | 354.3 |
| 70 | [5-(1-Isopropyl-pyrrolidin-3-yloxy)-1H-indol-2-yl]-(3-methyl-piperidin-1-yl)-methanone | 369.5 | 5-(1-Isopropyl-pyrrolidin-3-yloxy)-1H-indole-2-carboxylic acid (Example 5/step 2) and 3-methyl-piperidine (commercially available) | 370.3 |
| 71 | 5-(1-Isopropyl-pyrrolidin-3-yloxy)-1H-indole-2-carboxylic acid methyl-pyridin-3-ylmethyl-amide | 392.5 | 5-(1-Isopropyl-pyrrolidin-3-yloxy)-1H-indole-2-carboxylic acid (Example 5/step 2) and methyl-pyridin-3-ylmethyl-amine (commercially available) | 393.2 |
| 72 | 5-(1-Isopropyl-pyrrolidin-3-yloxy)-1H-indole-2-carboxylic acid [2-(2-methyl-piperidin-1-yl)-ethyl]-amide | 412.6 | 5-(1-Isopropyl-pyrrolidin-3-yloxy)-1H-indole-2-carboxylic acid (Example 5/step 2) and 2-(2-methyl-piperidin-1-yl)-ethyl-amine (commercially available) | 413.5 |
| 73 | (4-Hydroxymethyl-piperidin-1-yl)-[5-(1-isopropyl-pyrrolidin-3-yloxy)-1H-indol-2-yl]-methanone | 385.5 | 5-(1-Isopropyl-pyrrolidin-3-yloxy)-1H-indole-2-carboxylic acid (Example 5/step 2) and 4-hydroxymethyl-piperidine (commercially available) | 386.4 |
| 74 | (1,3-Dihydro-isoindol-2-yl)-[5-(1-isopropyl-pyrrolidin-3-yloxy)-1H-indol-2-yl]-methanone | 389.5 | 5-(1-Isopropyl-pyrrolidin-3-yloxy)-1H-indole-2-carboxylic acid (Example 5/step 2) and 1,3-dihydro-isoindole (commercially available) | 390.3 |

TABLE 1-continued

| Ex. No | Systematic name | MW | Starting materials | MW found $(M + H)^+$ |
|---|---|---|---|---|
| 75 | 5-(1-Isopropyl-piperidin-4-yloxy)-1H-indole-2-carboxylic acid methyl-(2-pyridin-2-yl-ethyl)-amide | 420.6 | 5(1-Isopropyl-piperidin-4-yloxy)-1H-indole-2-carboxylic acid (intermediate 1) and 2-pyridin-2-yl-ethyl-amine (commercially available) | 421.4 |
| 76 | 5-(1-Isopropyl-piperidin-4-yloxy)-1H-indole-2-carboxylic acid ethyl-pyridin-4-ylmethyl-amide | 420.6 | 5-(1-Isopropyl-piperidin-4-yloxy)-1H-indole-2-carboxylic acid (intermediate 1) and ethyl-pyridin-4-ylmethyl-amine (commercially available) | 421.4 |
| 77 | [5-(1-Isopropyl-piperidin-4-yloxy)-1H-indol-2-yl]-((S)-2-trifluoromethyl-pyrrolidin-1-yl)-methanone | 423.5 | 5-(1-Isopropyl-piperidin-4-yloxy)-1H-indole-2-carboxylic acid (intermediate 1) and (S)-2-trifluoromethyl-pyrrolidine (commercially available) | 424.4 |
| 78 | 5-(1-Isopropyl-piperidin-4-yloxy)-1H-indole-2-carboxylic acid (furan-2-ylmethyl)-amide | 381.5 | 5-(1-Isopropyl-piperidin-4-yloxy)-1H-indole-2-carboxylic acid (intermediate 1) and furan-2-ylmethyl-amine (commercially available) | 382.3 |
| 79 | 5-(1-Isopropyl-piperidin-4-yloxy)-1H-indole-2-carboxylic acid (2-morpholin-4-yl-ethyl)-amide | 414.5 | 5-(1-Isopropyl-piperidin-4-yloxy)-1H-indole-2-carboxylic acid (intermediate 1) and 2-morpholin-4-yl-ethyl-amine (commercially available) | 415.5 |
| 80 | 5-(1-Isopropyl-piperidin-4-yloxy)-1H-indole-2-carboxylic acid (3-methoxy-propyl)-amide | 373.5 | 5-(1-Isopropyl-piperidin-4-yloxy)-1H-indole-2-carboxylic acid (intermediate 1) and 3-methoxy-propyl-amine (commercially available) | 374.5 |
| 81 | 5-(1-Isopropyl-piperidin-4-yloxy)-1H-indole-2-carboxylic acid (3-dimethylamino-propyl)-amide | 386.5 | 5-(1-Isopropyl-piperidin-4-yloxy)-1H-indole-2-carboxylic acid (intermediate 1) and 3-dimethylamino-propyl-amine (commercially available) | 387.4 |
| 82 | 5-(1-Isopropyl-piperidin-4-yloxy)-1H-indole-2-carboxylic acid cyclopentylamide | 369.5 | 5-(1-Isopropyl-piperidin-4-yloxy)-1H-indole-2-carboxylic acid (intermediate 1) and cyclopentylamine (commercially available) | 370.4 |
| 83 | 5-(1-Isopropyl-piperidin-4-yloxy)-1H-indole-2-carboxylic acid cyclohexylamide | 383.5 | 5-(1-Isopropyl-piperidin-4-yloxy)-1H-indole-2-carboxylic acid (intermediate 1) and cyclohexylamine (commercially available) | 384.4 |
| 84 | 5-(1-Isopropyl-piperidin-4-yloxy)-1H-indole-2-carboxylic acid (2-piperidin-1-yl-ethyl)-amide | 412.6 | 5-(1-Isopropyl-piperidin-4-yloxy)-1H-indole-2-carboxylic acid (intermediate 1) and 2-piperidin-1-yl-ethyl-amine (commercially available) | 413.5 |
| 85 | Azetidin-1-yl-[5-(1-isopropyl-piperidin-4-yloxy)-1H-indol-2-yl]-methanone; hydrochloride | 341.5 | 5-(1-Isopropyl-piperidin-4-yloxy)-1H-indole-2-carboxylic acid (intermediate 1) and azetidine (commercially available) | 342.3 |
| 86 | [5-(1-Isopropyl-piperidin-4-yloxy)-1H-indol-2-yl]-(3-pyridin-2-yl-pyrrolidin-1-yl)-methanone | 432.6 | 5-(1-Isopropyl-piperidin-4-yloxy)-1H-indole-2-carboxylic acid (intermediate 1) and 3-pyridin-2-yl-pyrrolidine (commercially available) | 433.4 |
| 87 | 5-(1-Isopropyl-piperidin-4-yloxy)-1H-indole-2-carboxylic acid (1-ethyl-piperidin-3-yl)-amide | 412.6 | 5-(1-Isopropyl-piperidin-4-yloxy)-1H-indole-2-carboxylic acid (intermediate 1) and 1-ethyl-piperidin-3-yl-amine (commercially available) | 413.5 |
| 88 | (4-Isopropyl-piperazin-1-yl)-[5-(1-isopropyl-piperidin-4-yloxy)-1H-indol-2-yl]-methanone | 412.6 | 5-(1-Isopropyl-piperidin-4-yloxy)-1H-indole-2-carboxylic acid (intermediate 1) and 4-isopropyl-piperazine (commercially available) | 413.5 |

TABLE 1-continued

| Ex. No | Systematic name | MW | Starting materials | MW found $(M + H)^+$ |
|---|---|---|---|---|
| 89 | [5-(1-Isopropyl-piperidin-4-yloxy)-1H-indol-2-yl]-(2-methyl-pyrrolidin-1-yl)-methanone | 369.5 | 5-(1-Isopropyl-piperidin-4-yloxy)-1H-indole-2-carboxylic acid (intermediate 1) and 2-methyl-pyrrolidine (commercially available) | 370.4 |
| 90 | [5-(1-Isopropyl-piperidin-4-yloxy)-1H-indol-2-yl]-pyrrolidin-1-yl-methanone | 355.5 | 5-(1-Isopropyl-piperidin-4-yloxy)-1H-indole-2-carboxylic acid and pyrrolidine (commercially available) | 356.4 |
| 91 | [5-(1-Isopropyl-piperidin-4-yloxy)-1H-indol-2-yl]-piperidin-1-yl-methanone | 369.5 | 5-(1-Isopropyl-piperidin-4-yloxy)-1H-indole-2-carboxylic acid (intermediate 1) and piperidine (commercially available) | 370.4 |
| 92 | [5-(1-Isopropyl-piperidin-4-yloxy)-1H-indol-2-yl]-morpholin-4-yl-methanone | 371.5 | 5-(1-Isopropyl-piperidin-4-yloxy)-1H-indole-2-carboxylic acid (intermediate 1) and morpholine (commercially available) | 372.3 |
| 93 | [5-(1-Isopropyl-piperidin-4-yloxy)-1H-indol-2-yl]-thiomorpholin-4-yl-methanone | 387.5 | 5-(1-Isopropyl-piperidin-4-yloxy)-1H-indole-2-carboxylic acid (intermediate 1) and thiomorpholine (commercially available) | 388.3 |
| 95 | 5-(1-Isopropyl-piperidin-4-yloxy)-1H-indole-2-carboxylic acid cyclopropylmethyl-amide | 355.5 | 5-(1-Isopropyl-piperidin-4-yloxy)-1H-indole-2-carboxylic acid (intermediate 1) and cyclopropylmethyl-amine (commercially available) | 356.4 |
| 96 | [5-(1-Isopropyl-piperidin-4-yloxy)-1H-indol-2-yl]-(4-methoxy-piperidin-1-yl)-methanone | 399.5 | 5-(1-Isopropyl-piperidin-4-yloxy)-1H-indole-2-carboxylic acid (intermediate 1) and 4-methoxy-piperidine (commercially available) | 400.5 |
| 97 | [5-(1-Isopropyl-piperidin-4-yloxy)-1H-indol-2-yl]-(4-methyl-piperazin-1-yl)-methanone | 384.5 | 5-(1-Isopropyl-piperidin-4-yloxy)-1H-indole-2-carboxylic acid (intermediate 1) and 4-methyl-piperazine (commercially available) | 385.4 |
| 98 | [5-(1-Isopropyl-piperidin-4-yloxy)-1H-indol-2-yl]-(3-methoxy-piperidin-1-yl)-methanone | 399.5 | 5-(1-Isopropyl-piperidin-4-yloxy)-1H-indole-2-carboxylic acid (intermediate 1) and 3-methoxy-piperidine (commercially available) | 400.5 |
| 99 | (4-Benzyl-piperidin-1-yl)-[5-(1-isopropyl-piperidin-4-yloxy)-1H-indol-2-yl]-methanone | 459.6 | 5-(1-Isopropyl-piperidin-4-yloxy)-1H-indole-2-carboxylic acid (intermediate 1) and 4-benzyl-piperidine (commercially available) | 460.6 |
| 100 | 5-(1-Isopropyl-piperidin-4-yloxy)-1H-indole-2-carboxylic acid (2-methylsulfanyl-ethyl)-amide | 375.5 | 5-(1-Isopropyl-piperidin-4-yloxy)-1H-indole-2-carboxylic acid (intermediate 1) and 2-methylsulfanyl-ethyl-amine (commercially available) | 376.4 |
| 101 | 5-(1-Isopropyl-piperidin-4-yloxy)-1H-indole-2-carboxylic acid (1-phenyl-propyl)-amide | 419.6 | 5-(1-Isopropyl-piperidin-4-yloxy)-1H-indole-2-carboxylic acid (intermediate 1) and 1-phenyl-propyl-amine (commercially available) | 420.4 |
| 102 | (4,4-Difluoro-piperidin-1-yl)-[5-(1-isopropyl-piperidin-4-yloxy)-1H-indol-2-yl]-methanone | 405.5 | 5-(1-Isopropyl-piperidin-4-yloxy)-1H-indole-2-carboxylic acid (intermediate 1) and 4,4-difluoro-piperidine (commercially available) | 406.5 |
| 103 | 5-(1-Isopropyl-piperidin-4-yloxy)-1H-indole-2-carboxylic acid ethyl-(2-fluoro-benzyl)-amide | 437.6 | 5-(1-Isopropyl-piperidin-4-yloxy)-1H-indole-2-carboxylic acid (intermediate 1) and ethyl-(2-fluoro-benzyl)-amine (commercially available) | 438.4 |
| 104 | 5-(1-Isopropyl-piperidin-4 yloxy)-1H-indole-2-carboxylic acid 4-methyl-benzylamide | 405.5 | 5-(1-Isopropyl-piperidin-4-yloxy)-1H-indole-2-carboxylic acid (intermediate 1) and 4-methyl-benzylamine (commercially available) | 406.5 |

TABLE 1-continued

| Ex. No | Systematic name | MW | Starting materials | MW found $(M + H)^+$ |
|---|---|---|---|---|
| 105 | 1-[5-(1-Isopropyl-piperidin-4-yloxy)-1H-indole-2-carbonyl]-piperidine-4-carboxylic acid amide | 412.5 | 5-(1-Isopropyl-piperidin-4-yloxy)-1H-indole-2-carboxylic acid (intermediate 1) and piperidine-4-carboxylic acid amide (commercially available) | 413.4 |
| 106 | (3,6-Dihydro-2H-pyridin-1-yl)-[5-(1-isopropyl-piperidin-4-yloxy)-1H-indol-2-yl]-methanone | 367.5 | 5-(1-Isopropyl-piperidin-4-yloxy)-1H-indole-2-carboxylic acid (intermediate 1) and 3,6-dihydro-2H-pyridine (commercially available) | 368.3 |
| 107 | [5-(1-Isopropyl-piperidin-4-yloxy)-1H-indol-2-yl](3-methyl-piperidin-1-yl)-methanone | 383.5 | 5-(1-Isopropyl-piperidin-4-yloxy)-1H-indole-2-carboxylic acid (intermediate 1) and 3-methyl-piperidine (commercially available) | 384.3 |
| 108 | 5-(1-Isopropyl-piperidin-4-yloxy)-1H-indole-2-carboxylic acid methyl-pyridin-3-ylmethyl-amide | 406.5 | 5-(1-Isopropyl-piperidin-4-yloxy)-1H-indole-2-carboxylic acid (intermediate 1) and methyl-pyridin-3-ylmethyl-amine (commercially available) | 407.4 |
| 109 | 5-(1-Isopropyl-piperidin-4-yloxy)-1H-indole-2-carboxylic acid[2-(2-methyl-piperidin-1-yl)-ethyl]-amide | 426.6 | 5-(1-Isopropyl-piperidin-4-yloxy)-1H-indole-2-carboxylic acid (intermediate 1) and 2-(2-methyl-piperidin-1-yl)-ethyl]-amine (commercially available) | 427.5 |
| 110 | 5-(1-Isopropyl-piperidin-4-yloxy)-1H-indole-2-carboxylic acid dimethylcarbamoylmethyl-methyl-amide | 400.5 | 5-(1-Isopropyl-piperidin-4-yloxy)-1H-indole-2-carboxylic acid (intermediate 1) and dimethylcarbamoylmethyl-methyl-amine (commercially available) | 401.6 |
| 111 | (4-Hydroxymethyl-piperidin-1-yl)-[5-(1-isopropyl-piperidin-4-yloxy)-1H-indol-2-yl]-methanone | 399.5 | 5-(1-Isopropyl-piperidin-4-yloxy)-1H-indole-2-carboxylic acid (intermediate 1) and 4-hydroxymethyl-piperidine (commercially available) | 400.5 |
| 112 | (1,3-Dihydro-isoindol-2-yl)-[5-(1-isopropyl-piperidin-4-yloxy)-1H-indol-2-yl]-methanone | 403.5 | 5-(1-Isopropyl-piperidin-4-yloxy)-1H-indole-2-carboxylic acid (intermediate 1) and 1,3-dihydro-isoindole (commercially available) | 404.5 |
| 113 | 5-[2-(1-Methyl-pyrrolidin-2-yl)-ethoxy]-1H-indole-2-carboxylic acid cyclopentylamide | 355.5 | 5-[2-(1-Methyl-pyrrolidin-2-yl)-ethoxy]-1H-indole-2-carboxylic acid (intermediate 2) and cyclopentylamine (commercially available) | 356.3 |
| 114 | 5-[2-(1-Methyl-pyrrolidin-2-yl)-ethoxy]-1H-indole-2-carboxylic acid (2-piperidin-1-yl-ethyl)-amide | 398.5 | 5-[2-(1-Methyl-pyrrolidin-2-yl)-ethoxy]-1H-indole-2-carboxylic acid (intermediate 2) and (2-piperidin-1-yl-ethyl)-amine (commercially available) | 399.5 |
| 115 | Azetidin-1-yl-{5-[2-(1-methyl-pyrrolidin-2-yl)-ethoxy]-1H-indol-2-yl}-methanone | 327.4 | 5-[2-(1-Methyl-pyrrolidin-2-yl)-ethoxy]-1H-indole-2-carboxylic acid (intermediate 2) and azetidine (commercially available) | 328.2 |
| 116 | {5-[2-(1-Methyl-pyrrolidin-2-yl)-ethoxy]-1H-indol-2-yl}-(3-pyridin-2-yl-pyrrolidin-1-yl)-methanone | 418.5 | 5-[2-(1-Methyl-pyrrolidin-2-yl)-ethoxy]-1H-indole-2-carboxylic acid (intermediate 2) and 3-pyridin-2-yl-pyrrolidine (commercially available) | 419.4 |
| 117 | (4-Isopropyl-piperazin-1-yl)-{5-[2-(1-methyl-pyrrolidin-2-yl)-ethoxy]-1H-indol-2-yl}-methanone | 398.5 | 5-[2-(1-Methyl-pyrrolidin-2-yl)-ethoxy]-1H-indole-2-carboxylic acid (intermediate 2) and 4-isopropyl-piperazine (commercially available) | 399.5 |

TABLE 1-continued

| Ex. No | Systematic name | MW | Starting materials | MW found $(M + H)^+$ |
|---|---|---|---|---|
| 118 | (2-Methyl-pyrrolidin-1-yl)-{5-[2-(1-methyl-pyrrolidin-2-yl)-ethoxy]-1H-indol-2-yl}-methanone | 355.5 | 5-[2-(1-Methyl-pyrrolidin-2-yl)-ethoxy]-1H-indole-2-carboxylic acid (intermediate 2) and 2-methyl-pyrrolidine (commercially available) | 356.4 |
| 119 | {5-[2-(1-Methyl-pyrrolidin-2-yl)-ethoxy]-1H-indol-2-yl}-pyrrolidin-1-yl-methanone | 341.5 | 5-[2-(1-Methyl-pyrrolidin-2-yl)-ethoxy]-1H-indole-2-carboxylic acid (intermediate 2) and pyrrolidine (commercially available) | 342.2 |
| 120 | {5-[2-(1-Methyl-pyrrolidin-2-yl)-ethoxy]-1H-indol-2-yl}-piperidin-1-yl-methanone | 355.5 | 5-[2-(1-Methyl-pyrrolidin-2-yl)-ethoxy]-1H-indole-2-carboxylic acid (intermediate 2) and piperidine (commercially available) | 356.4 |
| 121 | {5-[2-(1-Methyl-pyrrolidin-2-yl)-ethoxy]-1H-indol-2-yl}-morpholin-4-yl-methanone | 357.5 | 5-[2-(1-Methyl-pyrrolidin-2-yl)-ethoxy]-1H-indole-2-carboxylic acid (intermediate 2) and morpholine (commercially available) | 358.3 |
| 122 | {5-[2-(1-Methyl-pyrrolidin-2-yl)-ethoxy]-1H-indol-2-yl}-thiomorpholin-4-yl-methanone | 373.5 | 5-[2-(1-Methyl-pyrrolidin-2-yl)-ethoxy]-1H-indole-2-carboxylic acid (intermediate 2) and thiomorpholine (commercially available) | 374.4 |
| 123 | (4-Methoxy-piperidin-1-yl)-{5-[2-(1-methyl-pyrrolidin-2-yl)-ethoxy]-1H-indol-2-yl}-methanone | 385.5 | 5-[2-(1-Methyl-pyrrolidin-2-yl)-ethoxy]-1H-indole-2-carboxylic acid (intermediate 2) and 4-methoxy-piperidine (commercially available) | 386.4 |
| 124 | (4-Methyl-piperazin-1-yl)-{5-[2-(1-methyl-pyrrolidin-2-yl)-ethoxy]-1H-indol-2-yl}-methanone | 370.5 | 5-[2-(1-Methyl-pyrrolidin-2-yl)-ethoxy]-1H-indole-2-carboxylic acid (intermediate 2) and 4-methyl-piperazine (commercially available) | 371.3 |
| 125 | (3-Methoxy-piperidin-1-yl)-{5-[2-(1-methyl-pyrrolidin-2-yl)-ethoxy]-1H-indol-2-yl}-methanone | 385.5 | 5-[2-(1-Methyl-pyrrolidin-2-yl)-ethoxy]-1H-indole-2-carboxylic acid (intermediate 2) and 3-methoxy-piperidine (commercially available) | 386.4 |
| 126 | (4-Benzyl-piperidin-1-yl)-{5-[2-(1-methyl-pyrrolidin-2-yl)-ethoxy]-1H-indol-2-yl}-methanone | 445.6 | 5-[2-(1-Methyl-pyrrolidin-2-yl)-ethoxy]-1H-indole-2-carboxylic acid (intermediate 2) and 4-benzyl-piperidine (commercially available) | 446.3 |
| 127 | (4-Hydroxy-piperidin-1-yl)-{5-[2-(1-methyl-pyrrolidin-2-yl)-ethoxy]-1H-indol-2-yl}-methanone | 371.5 | 5-[2-(1-Methyl-pyrrolidin-2-yl)-ethoxy]-1H-indole-2-carboxylic acid (intermediate 2) and 4-hydroxy-piperidine (commercially available) | 372.3 |
| 128 | (4,4-Difluoro-piperidin-1-yl)-{5-[2-(1-methyl-pyrrolidin-2-yl)-ethoxy]-1H-indol-2-yl}-methanone | 391.5 | 5-[2-(1-Methyl-pyrrolidin-2-yl)-ethoxy]-1H-indole-2-carboxylic acid (intermediate 2) and 4,4-difluoro-piperidine (commercially available) | 392.2 |
| 129 | (3,6-Dihydro-2H-pyridin-1-yl)-{5-[2-(1-methyl-pyrrolidin-2-yl)-ethoxy]-1H-indol-2-yl}-methanone | 353.5 | 5-[2-(1-Methyl-pyrrolidin-2-yl)-ethoxy]-1H-indole-2-carboxylic acid (intermediate 2) and 3,6-dihydro-2H-pyridin-1-yl (commercially available) | 354.3 |

TABLE 1-continued

| Ex. No | Systematic name | MW | Starting materials | MW found (M + H)+ |
|---|---|---|---|---|
| 130 | (3-Methyl-piperidin-1-yl)-{5-[2-(1-methyl-pyrrolidin-2-yl)-ethoxy]-1H-indol-2-yl}-methanone | 369.5 | 5-[2-(1-Methyl-pyrrolidin-2-yl)-ethoxy]-1H-indole-2-carboxylic acid (intermediate 2) and 3-methyl-piperidine (commercially available) | 370.4 |
| 131 | (4-Hydroxymethyl-piperidin-1-yl)-{5-[2-(1-methyl-pyrrolidin-2-yl)-ethoxy]-1H-indol-2-yl}-methanone | 385.5 | 5-[2-(1-Methyl-pyrrolidin-2-yl)-ethoxy]-1H-indole-2-carboxylic acid (intermediate 2) and 4-hydroxymethyl-piperidine (commercially available) | 386.4 |
| 132 | (1,3-Dihydro-isoindol-2-yl)-{5-[2-(1-methyl-pyrrolidin-2-yl)-ethoxy]-1H-indol-2-yl}-methanone | 389.5 | 5-[2-(1-Methyl-pyrrolidin-2-yl)-ethoxy]-1H-indole-2-carboxylic acid (intermediate 2) and 1,3-dihydro-isoindole (commercially available) | 390.3 |
| 133 | [5-(1-Isopropyl-pyrrolidin-3-yloxy)-1H-indol-2-yl]-((S)-2-trifluoromethyl-pyrrolidin-1-yl)-methanone | 409.4 | 5-(1-Isopropyl-pyrrolidin-3-yloxy)-1H-indole-2-carboxylic acid (Example 5/step 2) and (S)-2-trifluoromethyl-pyrrolidine (commercially available) | 410.5 |
| 134 | {5-[2-(1-Methyl-pyrrolidin-2-yl)-ethoxy]-1H-indol-2-yl}-((S)-2-trifluoromethyl-pyrrolidin-1-yl)-methanone | 409.4 | 5-[2-(1-Methyl-pyrrolidin-2-yl)-ethoxy]-1H-indole-2-carboxylic acid (intermediate 2) and (S)-2-trifluoromethyl-pyrrolidine (commercially available) | 410.5 |

Example 135

[5-((S)-1-Isopropyl-pyrrolidin-3-yloxy)-1H-indol-2-yl]-morpholin-4-yl-methanone a) Step 1: 5-((S)-1-Benzyl-pyrrolidin-3-yloxy)-1H-indole-2-carboxylic acid ethyl ester A mixture of 20.5 g (0.1 mol) ethyl-5-hydroxyindole-2-carboxylate, 23 g (0.13 mol) (R)-1-benzyl-pyrrolidine, 58 ml (0.2 mol) tri-n-butyl-phosphine and 50 g (0.2 mol) 1,1'-azodicarbonyl dipiperidine in 600 ml THF was stirred for 17 h at room temperature. The suspension was filtered and the filtrate was evaporated to dryness. The residue was taken up in 100 ml heptane/DCM 1/1 and the precipitate was filtered off and washed with 100 ml heptane/DCM 1/1. The filtrate was evaporated to dryness and the residue was taken up in 100 ml DCM and purified by flash column chromatography on silica eluting with a gradient of ethyl acetate/heptane 1/3 to 2/1. The product containing fractions were pooled and evaporated to dryness and again purified on silica eluting with a gradient from DCM/2N $NH_3$ in MeOH 99/1 to 19/1. 6.2 g of pure product were obtained from pooling and evaporation of pure fractions. This was recrystallized from diethyl ether and heptane and washed with diethyl ether/heptane to yield 3.5 g of pure product MS (m/e): 365.1 (MH+, 100%). 26 g of impure product were obtained from pooling and evaporation of the respective fractions. This was recrystallized from diethyl ether and heptane and washed with diethyl ether/heptane to yield 9.0 g of pure product. All filtrates were pooled and evaporated to dryness to yield 14 g of slightly impure product which was used without further purification in the consecutive steps.

b) Step 2: [5-((S)-1-Benzyl-pyrrolidin-3-yloxy)-1H-indol-2-yl]-morpholin-4-yl-methanone A mixture of 14 g 5-((S)-1-Benzyl-pyrrolidin-3-yloxy)-1H-indole-2-carboxylic acid ethyl ester and 1.45 g (0.035 mol) lithium hydroxide monohydrate in 100 ml THF/MeOH 1/1 and 25 ml water was heated to reflux for 2 hours and afterwards all organic volatiles removed under reduced pressure. 100 ml water (0° C.) was added and the mixture was extracted with 2×100 ml diethyl ether. The aqueous phase was adjusted to pH=2 with 4 N HCl and water was decanted from the formed precipitate. The mixture was dried at 50° C. under vacuum to yield 8.5 g brownish foam. This was taken up in 100 ml DMF and treated at 0° C. with 9.6 g (0.03 mol) 2-(1H-Benzotriazol-1-yl)-1,1,3,3-tetramethyl uronium tetrafluoroborate, 2.6 g (0.03 mol) morpholine and 25.8 ml (0.15 mol) N-ethyldiisopropylamine and stirred for 1 h at room temperature. The mixture was evaporated to dryness and 200 ml ethyl acetate, 200 ml water and 200 ml aqueous 10% $Na_2CO_3$ was added. The aqueous phase was extracted with 200 ml ethyl acetate. The combined organic phases were washed with 200 ml NaCl sat. aq. Dried with Na2SO4 filtered and evaporated to dryness. The residue was suspended in 100 ml diethyl ether/methanol 9/1 filtered, washed with 30 ml diethyl ether/methanol 9/1 and dried at 30° C. under vacuum to yield 6 g (0.014 mmol) of the title compound as white solid. MS (m/e): 406.5 (MH+, 100%).

c) Step 3: Morpholin-4-yl-[5-((S)-pyrrolidin-3-yloxy)-1H-indol-2-yl]-methanone

A mixture of 4.6 (0.016 mol) [5-((S)-1-Benzyl-pyrrolidin-3-yloxy)-1H-indol-2-yl]-morpholin-4-yl-methanone and 480 mg of 10% palladium on charcoal in 250 ml ethyl actetate/acetic acid 9/1 was hydrogenated at room temperature during 4 h. After filtration the filtrate was evaporated to dryness and the residue was taken up in 250 ml DCM and 150 ml 10% $Na_2CO_3$. The aqueous phase was extracted with 2×100 ml DCM and the combined organic phases were dried with $Na_2SO_4$ and evaporated to dryness to yield 2.77 g (77% of the title compound as off white solid. MS (m/e): 316.1 (MH+, 100%).

d) Step 4: [5-((S)-1-Isopropyl-pyrrolidin-3-yloxy)-1H-indol-2-yl]-morpholin-4-yl-methanone A mixture of 315 mg (1 mmol) Morpholin-4-yl-[5-((S)-pyrrolidin-3-yloxy)-1H-indol-2-yl]-methanone 615 mg (5 mmol) 2-bromopropane and 173 mg (1.25 mmol) $K_2CO_3$ in 3 ml DMF was heated to 50° C. for 16 h. The mixture was evaporated to dryness and taken up in 50 ml ethyl acetate and 50 ml water. The aqueous phase was extracted with 50 ml ethyl acetate and the combined organic phases washed with 50 ml NaCl sat. aq. dried with $Na_2SO_4$, filtered and evaporated to dryness. The residue was purified with column chromatography on silica eluting with a gradient from DCM/2N $NH_3$ in methanol 19/1 to 85/15. The product containing fractions were pooled and evaporated to dryness, treated with diethyl ether. The precipitate was filtered off and washed with a small portion diethyl ether. The title compound was dried at 30° C. under vacuum to be yield 172 mg (48%) as white solid. MS (m/e): 358.3 ($MH^+$, 100%).

According to the method described above for the synthesis of [5-((S)-1-isopropyl-pyrrolidin-3-yloxy)-1H-indol-2-yl]-morpholin-4-yl-methanone the respective enantiomer [5-((R)-1-isopropyl-pyrrolidin-3-yloxy)-1H-indol-2-yl]-morpholin-4-yl-methanone was synthesized in an analogous manner starting from ethyl-5-hydroxyindole-2-carboxylate and (S)-1-benzyl-pyrrolidine. MS (m/e): 358.3 ($MH^+$, 100%).

Example 136

[5-((S)-1-Cyclopropylmethyl-pyrrolidin-3-yloxy)-1H-indol-2-yl]-morpholin-4-yl-methanone According to the procedure described for the synthesis of [5-((S)-1-Isopropyl-pyrrolidin-3-yloxy)-1H-indol-2-yl]-morpholin-4-yl-methanone the title compound was synthesized from Morpholin-4-yl-[5-((S)-pyrrolidin-3-yloxy)-1H-indol-2-yl]-methanone and bromomethyl-cyclopropane. The title compound was obtained as light yellow solid. MS (m/e): 370.3 ($MH^+$, 100%).

Example 137

Morpholin-4-yl-[5-((S)-1-propyl-pyrrolidin-3-yloxy)-1H-indol-2-yl]-methanone

According to the procedure described for the synthesis of [5-((S)-1-Isopropyl-pyrrolidin-3-yloxy)-1H-indol-2-yl]-morpholin-4-yl-methanone the title compound was synthesized from Morpholin-4-yl-[5-((S)-pyrrolidin-3-yloxy)-1H-indol-2-yl]-methanone and 1-iodopropane.

The title compound was obtained as white solid. MS (m/e): 358.4 ($MH^+$, 100%).

Example 138

[6-(1-Isopropyl-pyrrolidin-3-yloxy)-1H-indol-2-yl]-morpholin-4-yl-methanone a) Step 1: 6-(1-Isopropyl-pyrrolidin-3-yloxy)-1H-indole-2-carboxylic acid ethyl ester A mixture of 1 g (4.8 mmol) ethyl-6-hydroxyindole-2-carboxylate (Journal of the American Chemical Society (1967), 89(13), 3349-50), 0.81 g (6.3 mmol) 1-isopropyl-3-pyrrolidinol, 2.83 ml (11 mmol) tri-n-butyl-phosphine and 2.56 g (9.75 mmol) 1,1'azodicarbonyl-dipiperidine in 50 ml THF was stirred at room temperature for 16 h. The suspension was filtered and the filtrated evaporated to dryness. The residue was purified with column chromatography on silica eluting with a gradient from DCM/2N $NH_3$ in MeOH 99/1 to 19/1. The product containing fractions were combined and evaporated to dryness to yield a brown oil which was crystallized from diethyl ether and heptane to afford 0.5 g of brownish crystals (MS (m/e): 317.1 ($MH^+$, 100%)). and after evaporation of the filtrate 0.6 g of slightly impure product which was used without further purification in the consecutive step.

b) Step 2: [6-(1-Isopropyl-pyrrolidin-3-yloxy)-1H-indol-2-yl]-morpholin-4-yl-methanone A mixture of 0.6 g 6-(1-isopropyl-pyrrolidin-3-yloxy)-1H-indole-2-carboxylic acid ethyl ester and 0.088 g (2.1 mmol) lithium hydroxide monohydrate in 20 ml THF/MeOH 1/1 and 5 ml water was heated to reflux for 1 hour and afterwards all organic volatiles removed under reduced pressure. 10 ml water (0° C.) was added and adjusted to pH=2 with 4 N HCl. All volatiles were removed under reduced pressure to yield 680 mg brownish foam. This was taken up in 5 ml DMF and treated with 0.61 g (1.9 mmol) 2-(1H-Benzotriazol-1-yl)-1,1,3,3-tetramethyl uronium tetrafluoroborate, 165 mg (1.9 mmol) morpholine and 1.63 ml (9.5 mmol) N-ethyldiisopropylamine and stirred for 16 h at room temperature. The mixture was evaporated to dryness and 50 ml ethyl acetate, 50 ml water and 50 ml aqueous 10% $Na_2CO_3$ was added. The aqueous phase was extracted with 50 ml ethyl acetate. The combined organic phases were washed with 50 ml NaCl sat. aq. dried with $Na_2SO_4$ filtered and evaporated to dryness. The residue was purified with column chromatography on silica eluting with a gradient from DCM/2N $NH_3$ in MeOH 19/1 to 85/15. The product containing fractions were pooled and evaporated to dryness. The residue was taken up in 5 ml diethyl ether, filtered and again washed with 5 ml diethyl ether. The title compound (165 mg) was after drying at 50° C. under vacuum obtained as white solid. MS (m/e): 358.4 ($MH^+$, 100%).

Intermediate 3

6-(1-Isopropyl-piperidin-4-yloxy)-1H-indole-2-carboxylic acid ethyl ester

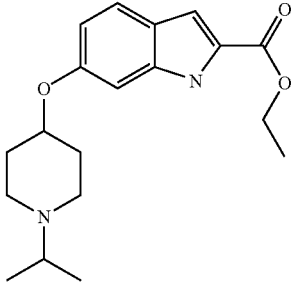

According to the procedure described for the synthesis of Example 138/step 1 6-(1-isopropyl-piperidin-4-yloxy)-1H-indole-2-carboxylic acid ethyl ester was synthesized from 6-hydroxy-1H-indole-2-carboxylic acid ethyl ester and 1-isopropyl-piperidin-4-ol (commercially available). The title compound was yielded in 15% as light brown solid. MS (m/e): 331.1 ($MH^+$, 100%).

Intermediate 4

6-[2-(1-Methyl-pyrrolidin-2-yl)-ethoxy]-1H-indole-2-carboxylic acid ethyl ester

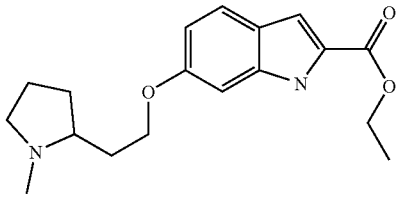

According to the procedure described for the synthesis of Example 138/step 1 6-[2-(1-methyl-pyrrolidin-2-yl)-ethoxy]-1H-indole-2-carboxylic acid ethyl ester was synthesized from 6-hydroxy-1H-indole-2-carboxylic acid ethyl ester and 2-(1-methyl-pyrrolidin-2-yl)-ethanol (commercially available). The title compound was yielded in 77% as light brown oil. MS (m/e): 317.3 (MH$^+$, 100%).

Intermediate 5

6-(3-Piperidin-1-yl-propoxy)-1H-indole-2-carboxylic acid ethyl ester

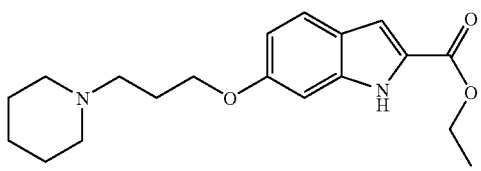

According to the procedure described for the synthesis of Example 138/step 1 6-(3-Piperidin-1-yl-propoxy)-1H-indole-2-carboxylic acid ethyl ester was synthesized from 6-hydroxy-1H-indole-2-carboxylic acid ethyl ester and 3-Piperidin-1-yl-propan-1-ol (commercially available). The title compound was yielded in 77% as light brown oil. MS (m/e): 317.3 (MH$^+$, 100%).

According to the procedure described for the synthesis of Example 138/step 2 further indole derivatives have been synthesized from 6-[2-(1-methyl-pyrrolidin-2-yl)-ethoxy]-1H-indole-2-carboxylic acid ethyl ester, 6-(1-isopropyl-piperidin-4-yloxy)-1H-indole-2-carboxylic acid ethyl ester, 6-(1-isopropyl-pyrrolidin-3-yloxy)-1H-indole-2-carboxylic acid ethyl ester or 6-(3-Piperidin-1-yl-propoxy)-1H-indole-2-carboxylic acid ethyl ester, respectively, with the respective amine mentioned in Table 2. The results are shown in Table 2 and comprise Example 139 to Example 162.

| Ex. No | Systematic name | MW | Starting materials | MW found (M + H)$^+$ |
|---|---|---|---|---|
| 139 | [6-(1-Isopropyl-piperidin-4-yloxy)-1H-indol-2-yl]-morpholin-4-yl-methanone | 371.5 | 6-(1-Isopropyl-piperidin-4-yloxy)-1H-indole-2-carboxylic acid ethyl ester (intermediate 3) and morpholine (commercially available) | 372.4 |
| 140 | [6-(1-Isopropyl-piperidin-4-yloxy)-1H-indol-2-yl]-thiomorpholin-4-yl-methanone | 387.5 | 6-(1-Isopropyl-piperidin-4-yloxy)-1H-indole-2-carboxylic acid ethyl ester (intermediate 3) and thiomorpholine (commercially available) | 388.5 |
| 141 | [6-(1-Isopropyl-piperidin-4-yloxy)-1H-indol-2-yl]-piperidin-1-yl-methanone | 369.5 | 6-(1-Isopropyl-piperidin-4-yloxy)-1H-indole-2-carboxylic acid ethyl ester (intermediate 3) and piperidine (commercially available) | 370.3 |
| 142 | [6-(1-Isopropyl-piperidin-4-yloxy)-1H-indol-2-yl]-(4-methyl-piperidin-1-yl)-methanone | 383.5 | 6-(1-Isopropyl-piperidin-4-yloxy)-1H-indole-2-carboxylic acid ethyl ester (intermediate 3) and 4-methyl-piperidine (commercially available) | 384.5 |
| 143 | [6-(1-Isopropyl-piperidin-4-yloxy)-1H-indol-2-yl]-(4-methoxy-piperidin-1-yl)-methanone | 399.5 | 6-(1-Isopropyl-piperidin-4-yloxy)-1H-indole-2-carboxylic acid ethyl ester (intermediate 3) and 4-methoxy-piperidine (commercially available) | 400.6 |
| 144 | [6-(1-Isopropyl-piperidin-4-yloxy)-1H-indol-2-yl]-pyrrolidin-1-yl-methanone | 355.5 | 6-(1-Isopropyl-piperidin-4-yloxy)-1H-indole-2-carboxylic acid ethyl ester (intermediate 3) and pyrrolidine (commercially available) | 356.5 |
| 145 | [6-(1-Isopropyl-piperidin-4-yloxy)-1H-indol-2-yl]-(2-methyl-pyrrolidin-1-yl)-methanone | 369.5 | 6-(1-Isopropyl-piperidin-4-yloxy)-1H-indole-2-carboxylic acid ethyl ester (intermediate 3) and 2-methyl-pyrrolidine (commercially available) | 370.1 |
| 146 | Azepan-1-yl-[6-(1-isopropyl-piperidin-4-yloxy)-1H-indol-2-yl]-methanone | 383.5 | 6-(1-Isopropyl-piperidin-4-yloxy)-1H-indole-2-carboxylic acid ethyl ester (intermediate 3) and azepane (commercially available) | 384.1 |
| 147 | (2,6-Dimethyl-morpholin-4-yl)-[6-(1-isopropyl-piperidin-4-yloxy)-1H- | 399.5 | 6-(1-Isopropyl-piperidin-4-yloxy)-1H-indole-2-carboxylic acid ethyl ester (intermediate | 400.0 |

| Ex. No | Systematic name | MW | Starting materials | MW found (M + H)+ |
|---|---|---|---|---|
| | indol-2-yl]-methanone | | 3) and 2,6-dimethyl-morpholine (commercially available) | |
| 148 | 6-(1-Isopropyl-piperidin-4-yloxy)-1H-indole-2-carboxylic acid cyclopropylmethyl-amide | 355.5 | 6-(1-Isopropyl-piperidin-4-yloxy)-1H-indole-2-carboxylic acid ethyl ester (intermediate 3) and cyclopropylmethyl-amine (commercially available) | 356.5 |
| 149 | 6-(1-Isopropyl-piperidin-4-yloxy)-1H-indole-2-carboxylic acid 4-fluoro-benzylamide | 409.5 | 6-(1-Isopropyl-piperidin-4-yloxy)-1H-indole-2-carboxylic acid ethyl ester (intermediate 3) and 4-fluoro-benzylamine (commercially available) | 410.3 |
| 150 | 6-(1-Isopropyl-piperidin-4-yloxy)-1H-indole-2-carboxlic acid (furan-2-ylmethyl)-amide | 381.5 | 6-(1-Isopropyl-piperidin-4-yloxy)-1H-indole-2-carboxylic acid ethyl ester (intermediate 3) and furan-2-ylmethyl-amine (commercially available) | 382.4 |
| 151 | Azepan-1-yl-{6-[2-(1-methyl-pyrrolidin-2-yl)-ethoxy]-1H-indol-2-yl}-methanone | 369.5 | 6-[2-(1-Methyl-pyrrolidin-2-yl)-ethoxy]-1H-indole-2-carboxylic acid ethyl ester (intermediate 4) and azepane (commercially available) | 370.3 |
| 152 | {6-[2-(1-Methyl-pyrrolidin-2-yl)-ethoxy]-1H-indol-2-yl}-pyrrolidin-1-yl-methanone | 341.5 | 6-[2-(1-Methyl-pyrrolidin-2-yl)-ethoxy]-1H-indole-2-carboxylic acid ethyl ester (intermediate 4) and pyrrolidine (commercially available) | 342.1 |
| 153 | [6-(1-Isopropyl-pyrrolidin-3-yloxy)-1H-indol-2-yl]-thiomorpholin-4-yl-methanone | 373.5 | 6-(1-Isopropyl-pyrrolidin-3-yloxy)-1H-indole-2-carboxylic acid ethyl ester (Example 138/step 1) and thiomorpholine (commercially available) | 374.5 |
| 154 | [6-(1-Isopropyl-pyrrolidin-3-yloxy)-1H-indol-2-yl]-piperidin-1-yl-methanone | 355.5 | 6-(1-Isopropyl-pyrrolidin-3-yloxy)-1H-indole-2-carboxylic acid ethyl ester (Example 138/step 1) and piperidine (commercially available) | 356.5 |
| 155 | [6-(1-Isopropyl-pyrrolidin-3-yloxy)-1H-indol-2-yl]-(4-methyl-piperidin-1-yl)-methanone | 369.5 | 6-(1-Isopropyl-pyrrolidin-3-yloxy)-1H-indole-2-carboxylic acid ethyl ester (Example 138/step 1) and 4-methyl-piperidine (commercially available) | 370.3 |
| 156 | [6-(1-Isopropyl-pyrrolidin-3-yloxy)-1H-indol-2-yl]-(4-methoxy-piperidin-1-yl)-methanone | 385.5 | 6-(1-Isopropyl-pyrrolidin-3-yloxy)-1H-indole-2-carboxylic acid ethyl ester (Example 138/step 1) and 4-methoxy-piperidine (commercially available) | 386.5 |
| 157 | [6-(1-Isopropyl-pyrrolidin-3-yloxy)-1H-indol-2-yl]-pyrrolidin-1-yl-methanone | 341.5 | 6-(1-Isopropyl-pyrrolidin-3-yloxy)-1H-indole-2-carboxylic acid ethyl ester (Example 138/step 1) and pyrrolidine (commercially available) | 342.1 |
| 158 | Azepan-1-yl-[6-(1-isopropyl-pyrrolidin-3-yloxy)-1H-indol-2-yl]-methanone | 369.5 | 6-(1-Isopropyl-pyrrolidin-3-yloxy)-1H-indole-2-carboxylic acid ethyl ester (Example 138/step 1) and azepane (commercially available) | 370.3 |
| 159 | (2,6-Dimethyl-morpholin-4-yl)-[6-(1-isopropyl-pyrrolidin-3-yloxy)-1H-indol-2-yl]-methanone | 385.5 | 6-(1-Isopropyl-pyrrolidin-3-yloxy)-1H-indole-2-carboxylic acid ethyl ester (Example 138/step 1) and 2,6-dimethyl-morpholin (commercially available) | 386.5 |

-continued

| Ex. No | Systematic name | MW | Starting materials | MW found $(M + H)^+$ |
|---|---|---|---|---|
| 160 | 6-(1-Isopropyl-pyrrolidin-3-yloxy)-1H-indole-2-carboxylic acid cyclopropylmethyl-amide | 341.5 | 6-(1-Isopropyl-pyrrolidin-3-yloxy)-1H-indole-2-carboxylic acid ethyl ester (Example 138/ step 1) and cyclopropylmethyl amine (commercially available) | 342.3 |
| 161 | (4,4-Difluoro-piperidin-1-yl)-[6-(3-piperidin-1-yl-propoxy)-1H-indol-2-yl]-methanone | 371.5 | 6-(3-Piperidin-1-yl-propoxy)-1H-indole-2-carboxylic acid ethyl ester (intermediate 5) and 4,4'-difluoropiperidine (commercially available) | 371.6 |
| 162 | 6-(1-Isopropyl-pyrrolidin-3-yloxy)-1H-indole-2-carboxylic acid cyclopropylmethyl-amide | 341.5 | 6-(3-Piperidin-1-yl-propoxy)-1H-indole-2-carboxylic acid ethyl ester (intermediate 5) and morpholine (commercially available) | 342.3 |

Example 163

[5-(1-Isoopropyl-pyrrolidin-3-yloxy)-1H-indol-2-yl]-morpholin-4-yl-methanethione A mixture of 0.1 g (0.28 mmol) [5-(1-isopropyl-pyrrolidin-3-yloxy)-1H-indol-2-yl]-morpholin-4-yl-methanone and 141 mg (0.47 mmol) Lawson's reagent in 10 ml THF was stirred for 68 h at room temperature. The mixture was evaporated to dryness and the residue purified by column chromatography on silica eluting with a gradient from DCM/2N $NH_3$ in methanol 97/3 to 19/1 to yield 56 mg (54%) of the title compound as yellow foam. MS (m/e): 374.4 ($MH^+$, 100%).

Example 164

[5-Fluoro-6-(1-isopropyl-piperidin-4-yloxy)-1H-indol-2-yl]-morpholin-4-yl-methanone a) Step 1: 4-Benzyloxy-3-fluoro-benzaldehyde A mixture of 18.6 g (0.133 mol) 3-fluoro-4-hydroxy-benzyldehyde, 24.9 g (0.146 mol) benzylbromide and 22 g (0.159 mol) $K_2CO_3$ in 150 ml DMF was heated to 55° C. for 2 h. After filtration and washing of the residue with 30 ml DMF all volatiles were removed under vacuum. The residue was partitioned between water and ethyl acetate and brine and extracted with ethyl acetate. The combined organic layers were washed with brine, dried with $Na_2SO_4$, filtered, evaporated and the residue was re-crystallized from ethyl acetate/heptane and used without further purification. MS (m/e): 231.1 ($MH^+$, 100%).

b) Step 2: 6-Benzyloxy-5-fluoro-1H-indole-2-carboxylic acid methyl ester

A mixture of methyl 2-azidoacetate, 4-benzyloxy-3-fluoro-benzaldehyde and sodium methanolate (in methanol) in toluene was reacted for 3 h at 0° C. The residue after filtration of the suspension was washed with methanol, partitioned between ethyl acetate and ammonium chloride solution and extracted with ethyl acetate. The combined organic layers were dried with $Na_2SO_4$, evaporated to dryness and the residue taken up in p-xylene and brought to reflux temperature for 2 h. After concentration the mixture was left to crystallize and the formed crystals were filtered off and washed with toluene. The title compound was after drying at 40° C. under vacuum obtained as yellow crystals. MS (m/e): 300.3 ($MH^+$, 100%).

c) Step 3: 5-Fluoro-6-hydroxy-1H-indole-2-carboxylic acid methyl ester

A solution of 20.2 g (0.067 mol) 6-benzyloxy-5-fluoro-1H-indole-2-carboxylic acid methyl ester in 800 ml ethyl acetate was treated with 2 g (10%) Pd/C and hydrogenated at 1 bar for 2 h. After filtration and evaporation the residue was re-crystallized from ethyl acetate. The crystals were filtered off washed with diethyl ether and dried at 40° C. under vacuum to yield 10.9 g (74%) of the title compound as white crystals. MS (m/e): 208.1 ($MH^-$, 100%).

d) Step 4: 5-Fluoro-6-(1-isopropyl-piperidin-4-yloxy)-1H-indole-2-carboxylic acid methyl ester According to the procedure described for the synthesis of Example 5 (step 2) the title compound was synthesized starting from 5-fluoro-6-hydroxy-1H-indole-2-carboxylic acid methyl ester and 1-isopropyl-piperidin-4-ol (commercially available) in 48% yield as white crystals. MS (m/e): 335.4 ($MH^+$, 100%).

e) Step 5: 5-Fluoro-6-(1-isopropyl-piperidin-4-yloxy)-1H-indole-2-carboxylic acid According to the procedure described for the synthesis of Example 5 (step 3) the title compound was synthesized starting from 5-fluoro-6-(1-isopropyl-piperidin-4-yloxy)-1H-indole-2-carboxylic acid methyl ester and lithium hydroxide and used without further purification in the consecutive step. MS (m/e): 321.4($MH^+$, 100%).

f) Step 6: [5-Fluoro-6-(1-isopropyl-piperidin-4-yloxy)-1H-indol-2-yl]-morpholin-4-yl-methanone According to the procedure described for the synthesis of Example 5 (step 3) the title compound was synthesized starting from 5-fluoro-6-(1-isopropyl-piperidin-4-yloxy)-1H-indole-2-carboxylic acid and morpholine (commercially available) in 68% yield. MS (m/e): 390.4($MH^+$, 100%).

Example 165

[5-Fluoro-6-(1-isopropyl-piperidin-4-yloxy)-1H-indol-2-yl]-thiomorpholin-4-yl-methanone According to the procedure described above for the synthesis of [5-fluoro-6-(1-isopropyl-piperidin-4-yloxy)-1H-indol-2-yl]-morpholin-4-yl-methanone (Example 164)

the title compound was synthesized from 5-fluoro-6-(1-isopropyl-piperidin-4-yloxy)-1H-indole-2-carboxylic acid and thiomorpholine (commercially available). MS (m/e): 406.3 (MH$^+$, 100%).

Example 166

[5-Fluoro-6-(1-isopropyl-piperidin-4-yloxy)-1H-indol-2-yl]-piperidin-1-yl-methanone According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and piperidine (commercially available). MS (m/e): 388.0 (MH$^+$, 100%).

Example 167

[5-Fluoro-6-(1-isopropyl-piperidin-4-yloxy)-1H-indol-2-yl]-(4-methyl-piperidin-1-yl)-methanone According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and 4-methyl-piperidine (commercially available). MS (m/e): 402.3 (MH$^+$, 100%).

Example 168

[5-Fluoro-6-(1-isopropyl-piperidin-4-yloxy)-1H-indol-2-yl]-(4-methoxy-piperidin-1-yl)-methanone According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and 4-methoxy-piperidine (commercially available). MS (m/e): 418.1 (MH$^+$, 100%).

Example 169

[5-Fluoro-6-(1-isopropyl-pip eridin-4-yloxy)-1H-indol-2-yl]-pyrrolidin-1-yl-methanone According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and pyrrolidine (commercially available). MS (m/e): 374.0 (MH$^+$, 100%).

Example 170

Azepan-1-yl-[5-fluoro-6-(1-isoopropyl-piperidin-4-yloxy)-1H-indol-2-yl]-methanone According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and azepane (commercially available). MS (m/e): 402.1 (MH$^+$, 100%).

Example 171

5-Fluoro-6-(1-isopropyl-piperidin-4-yloxy)-1H-indole-2-carboxylic acid cyclopropyl-methyl-amide According to the procedure described above for the synthesis of [5-fluoro-6-(1-isopropyl-piperidin-4-yloxy)-1H-indol-2-yl]-morpholin-4-yl-methanone (Example 164) the title compound was synthesized from 5-fluoro-6-(1-isopropyl-piperidin-4-yloxy)-1H-indole-2-carboxylic acid and cyclopropylmethylamine (commercially available). MS (m/e): 374.0 (MH$^+$, 100%).

Example 172

[1-Ethyl-5-(1-isoopropyl-pyrrolidin-3-yloxy)-1H-indol-2-yl]morpholin-4-yl-methanone A mixture of 0.179 g (0.5 mmol) [5-(1-isopropyl-pyrrolidin-3-yloxy)-1H-indol-2-yl]-morpholin-4-yl-methanone, 0.094 g (0.6 mmol) iodoethane and 0.022 g (0.5 mmol) NaH as 55% suspension in oil in 2 ml N,N-dimethylacetamide was heated to 60° C. for 1 h. After evaporation of all volatiles the residue was taken up in 50 ml ethyl acetate and 50 ml water and extracted with ethyl acetate. The combined organic layers were washed with brine, dried over Na$_2$SO$_4$ and evaporated to dryness. The residue was purified with flash column chromatography on silica eluting with a mixture of DCM/2N NH$_3$ in MeOH to yield after evaporation of the product fractions a yellow oil which was crystallized from diethyl ether. The title compound was obtained (0.051 g (26%)) as white solid. MS (m/e): 386.5 (MH$^+$, 100%).

Example 173

[1-Isopropyl-5-(1-isopropyl-pyrrolidin-3-yloxy)-1H-indol-2-yl]-morpholin-4-yl-methanone According to the procedure described above for the synthesis of [1-ethyl-5-(1-isopropyl-pyrrolidin-3-yloxy)-1H-indol-2-yl]-morpholin-4-yl-methanone (Example 172) the title compound was synthesized from [5-(1-isopropyl-pyrrolidin-3-yloxy)-1H-indol-2-yl]-morpholin-4-yl-methanone and 2-iodopropane (commercially available). MS (m/e): 400.5 (MH$^+$, 100%).

Example 174

(3,3-Difluoro-piperidin-1-yl)-[5-(1-isopropyl-piperidin-4-yloxy)-1H-indol-2-yl]-methanone According to the procedure described for the synthesis of Example 5/step 3 the title compound was synthesized from [5-(1-isopropyl-piperidin-4-yloxy)-1H-indole-2-carboxylic acid and 3,3'-difluoropiperidine (commercially available). MS (m/e): 406.6 (MH$^+$, 100%).

Example 175

(4,4-Difluoro-piperidin-1-yl)-[5-((S)-1-isopropyl-pyrrolidin-3-yloxy)-1H-indol-2-yl]-methanone a) Step 1: [5-((S)-1-Benzyl-pyrrolidin-3-yloxy)-1H-indol-2-yl]-(4,4-difluoro-piperidin-1-yl)-methanone According to the procedure described for Example 135 the title compound was synthesized from 5-((S)-1-benzyl-pyrrolidin-3-yloxy)-1H-indole-2-carboxylic acid ethyl ester and 4,4-difluoropiperidine. MS (m/e): 440.4 (MH$^+$, 100%).

b) Step 2: (4,4-Difluoro-piperidin-1-yl)-[5-((S)-pyrrolidin-3-yloxy)-1H-indol-2-yl]-methanone According to the procedure described for Example 135 the title compound was synthesized from [5-((S)-1-benzyl-pyrrolidin-3-yloxy)-1H-indol-2-yl]-(4,4-difluoro-piperidin-1-yl)-methanone through hydrogenation. MS (m/e): 350.5 (MH$^+$, 100%).

c) Step 3: (4,4-Difluoro-piperidin-1-yl)-[5-((S)-1-isopropyl-pyrrolidin-3-yloxy)-1H-indol-2-yl]-methanone According to the procedure described for example 135 the title compound was synthesized from (4,4-difluoro-piperidin-1-yl)-[5-((S)-pyrrolidin-3-yloxy)-1H-indol-2-yl]-methanone and 2-iodopropane. MS (m/e): 392.3 (MH$^+$, 100%).

Example 176

(4,4-Difluoro-piperidin-1-yl)-[5-((R)-1-isopropyl-parrolidin-3-yloxy)-1H-indol-2-yl]-methanone According to the method described above for the synthesis of (4,4-difluoro-piperidin-1-yl)-[5-((S)-1-isopropyl-pyrrolidin-3-yloxy)-1H-indol-2-yl]-methanone (Example 75) the respective enantiomer (4,4-difluoro-piperidin-1-yl)-[5-((R)-1-isopropyl-pyrrolidin-3-yloxy)-1H-indol-2-yl]-methanone was synthesized in an analogous manner starting from ethyl-5-hydroxyindole-2-carboxylate and (R)-1-benzyl-pyrrolidine. MS (m/e): 392.4 (MH$^+$, 100%).

Example 177

[5-((S)-1-Isopropyl-pyrrolidin-3-yloxy)-1H-indol-2-yl]-pyrrolidin-1-yl-methanone a) Step 1: 5-((S)-1-Isopropyl-pyrrolidin-3-yloxy)-1H-indole-2-carboxylic acid ethyl ester A mixture of 18 g (49 mmol) 5-((S)-1-benzyl-pyrrolidin-3-yloxy)-1H-indole-2-carboxylic acid ethyl ester, 28.3 ml acetic acid and 2 g Pd/C 10% was hydrogenated with H$_2$ at room temperature during 16 h. The mixture was filtered and the filtrate evaporated to dryness. The residue was taken up in 500 ml DMF and 34.1 g (247 mmol) K$_2$CO$_3$ and 42 g (247 mmol) 2-iodopropane was added and the mixture was stirred for 4 h at 50° C. After filtration and evaporation the residue was purified on silica eluting with a gradient formed from DCM/MeOH (2N NH$_3$) 98/2 to 92/8 to yield after evaporation of the product fractions 60% of the title compound as light brown solid. MS (m/e): 317.3 (MH$^+$, 100%).

b) Step 2: 5-((S)-1-Isopropyl-pyrrolidin-3-yloxy)-1H-indole-2-carboxylic acid 1:1 hydrochloride A mixture of 8.9 g (28 mmol) 5-((S)-1-isopropyl-pyrrolidin-3-yloxy)-1H-indole-2-carboxylic acid ethyl ester and 1.3 g (31 mmol) LiOH monohydrate in 100 ml THF, 50 ml water and 10 ml methanol was heated to reflux for 2 h and the organic solvents were removed under reduced pressure. After addition of 4 N HCl aq. the mixture was evaporated to dryness and used in the subsequent step without further purification. MS (m/e): 289.3 (MH$^+$, 100%).

c) Step 3: [5-((S)-1-Isopropyl-pyrrolidin-3-yloxy)-1H-indol-2-yl]-pyrrolidin-1-yl-methanone According to the procedure described for the synthesis of Example 1 the title compound was synthesized from 5-((S)-1-isopropyl-pyrrolidin-3-yloxy)-1H-indole-2-carboxylic acid 1:1 hydrochloride and pyrrolidine under coupling conditions employing TBTU and DIPEA in DMF. The crude product was purified over silica eluting with a gradient formed from DCM/MeOH(2 N NH$_3$) 98/2 to 94/6. The product fractions were evaporated to yield the title compound as off-white solid. (m/e): 342.3 (MH$^+$, 100%).

Example 178

(4,4-Difluoro-piperidin-1-yl)-[5-fluoro-6-(3-piperidin-1-yl-propoxy)-1H-indol-2-yl]-methanone a) Step 1: 5-Fluoro-6-(3-piperidin-1-yl-propoxy)-1H-indole-2-carboxylic acid methyl ester According to the procedure described above for the synthesis of 5-fluoro-6-(1-isopropyl-piperidin-4-yloxy)-1H-indole-2-carboxylic acid methyl ester (Example 164/Step 4) the title compound was synthesized from 5-fluoro-6-hydroxy-1H-indole-2-carboxylic acid methyl ester and 3-piperidin-1-yl-propan-1-ol (commercially available). MS (m/e): 335.4 (MH$^+$, 100%).

b) Step 2: 5-Fluoro-6-(3-piperidin-1-yl-propoxy)-1H-indole-2-carboxylic acid

According to the procedure described for the synthesis of Example 5 (step 3) the title compound was synthesized starting from 5-fluoro-6-(3-piperidin-1-yl-propoxy)-1H-indole-2-carboxylic acid methyl ester and lithium hydroxide and used without further purification in the consecutive step. MS (m/e): 321.4 (MH$^+$, 100%).

c) Step 3: (4,4-Difluoro-piperidin-1-yl)-[5-fluoro-6-(3-piperidin-1-yl-propoxy)-1H-indol-2-yl]-methanone According to the procedure described for the synthesis of Example 5 (step 3) the title compound was synthesized starting from 5-fluoro-6-(3-piperidin-1-yl-propoxy)-1H-indole-2-carboxylic acid and 4,4'-difluoropiperidine (commercially available). MS (m/e): 424.5 (MH$^+$, 100%).

Example 179

[5-Fluoro-6-(3-piperidin-1-yl-propoxy)-1H-indol-2-yl]-morpholin-4-yl-methanone

According to the procedure described for the synthesis of Example 5 (step 3) the title compound was synthesized starting from 5-fluoro-6-(3-piperidin-1-yl-propoxy)-1H-indole-2-carboxylic acid and morpholine (commercially available). MS (m/e): 390.5 (MH$^+$, 100%).

Example 180

(4,4-Difluoro-piperidin-1-yl)-[1-isopropyl-5-(1-isopropyl-piperidin-4-yloxy)-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and 2-bromopropane (commercially available). MS (m/e): 448.5 (MH$^+$, 100%).

Example 181

(4,4-Difluoro-piperidin-1-yl)-[5-(1-isopropyl-piperidin-4-yloxy)-1-(2-methoxy-ethyl)-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and 2-bromoethyl methyl ether (commercially available). MS (m/e): 464.6 (MH$^+$, 100%).

Example 182

(4,4-Difluoro-piperidin-1-yl)-[1-ethyl-5-(1-isopropyl-piperidin-4-yloxy)-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and bromoethane (commercially available). MS (m/e): 434.5 (MH$^+$, 100%).

Example 183

(4,4-Difluoro-piperidin-1-yl)-[5-(1-isopropyl-piperidin-4-yloxy)-1-(2,2,2-trifluoro-ethyl)-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and 2,2,2-trifluoroethyl trifluoromethanesulfonate (commercially available). MS (m/e): 434.5 (MH$^+$, 100%).

Example 184

[1-Cyclopropylmethyl-5-(1-isopropyl-piperidin-4-yloxy)-1H-indol-2-yl]-(4,4-difluoro-piperidin-1-yl)-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and bromomethyl cyclopropane (commercially available). MS (m/e): 434.5 (MH$^+$, 100%).

Example 185

[5-(1-Isopropyl-piperidin-4-yloxy)-1-(2,2,2-trifluoro-ethyl)-1H-indol-2-yl]-pyrrolidin-1-yl-methanone According to the procedure described for the synthesis of Example 172 the title compound was synthesized starting from [5-(1-isopropyl-piperidin-4-yloxy)-1H-indol-2-yl]-pyrrolidin-1-yl-methanone (Example 90) and 2,2,2-trifluoroethyl trifluoromethane-sulfonate (commercially available). MS (m/e): 437.5 (MH$^+$, 100%).

Example 186

[5-(1-Isopropyl-piperidin-4-yloxy)-1-(2,2,2-trifluoro-ethyl)-1H-indol-2-yl]-morpholin-4-yl-methanone According to the procedure described for the synthesis of Example 172 the title compound was synthesized starting from [5-(1-isopropyl-piperidin-4-yloxy)-1H-indol-2-yl]-morpholin-4-yl-methanone (Example 92) and 2,2,2-trifluoroethyl trifluoromethane-sulfonate (commercially available). MS (m/e): 454.5 (MH$^+$, 100%).

Example 187

(3,3-Difluoro-piperidin-1-yl)-[5-(1-isopropyl-piperidin-4-yloxy)-1-(2,2,2-trifluoro-ethyl)-1H-indol-2-yl]-methanone According to the procedure described for the synthesis of Example 172 the title compound was synthesized starting from (3,3-difluoro-piperidin-1-yl)-[5-(1-isopropyl-piperidin-4-yloxy)-1H-indol-2-yl]-methanone (Example 174) and 2,2,2-trifluoroethyl trifluoromethanesulfonate (commercially available). MS (m/e): 488.5 (MH$^+$, 100%).

Example 188

(4,4-Difluoro-piperidin-1-yl)-[1-(2-hydroxy-ethyl)-5-(1-isopropyl-piperidin-4-yloxy)-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and 1,3,2-dioxathiolane-2,2-dioxide (commercially available). MS (m/e): 488.5 (MH$^+$, 100%).

Example 189

(4,4-Difluoro-piperidin-1-yl)-[5-(1-isopropyl-piperidin-4-yloxy)-1-methanesulfonyl-1H-indol-2-yl]-methanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and methanesulfonyl chloride (commercially available). MS (m/e): 484.5 (MH$^+$, 100%).

Example 190

1-[2-(4,4-Difluoro-piperidine-1-carbonyl)-5-(1-isopropyl-piperidin-4-yloxy)-indol-1-yl]-ethanone According to the procedure described for the synthesis of Example 172 the title compound was synthesized starting from (4,4-difluoro-piperidin-1-yl)-[5-(1-isopropyl-piperidin-4-yloxy)-1H-indol-2-yl]-methanone (Example 102) and acetyl chloride (commercially available). MS (m/e): 448.5 (MH$^+$, 100%).

Example 191

(4,4-Difluoro-piperidin-1-yl)-[5-(1-isopropyl-piperidin-4-yloxy)-1-methyl-1H-indol-2-yl]-methanone a) Step 1: 4-[2-(4,4-Difluoro-piperidine-1-carbonyl)-1-methyl-1H-indol-5-yloxy]-1-isopropyl-1-methyl-piperidinium as monomethylsulfate salt A mixture of (4,4-difluoro-piperidin-1-yl)-[5-(1-isopropyl-piperidin-4-yloxy)-1H-indol-2-yl]-methanone (Example 102, 400 mg, 0.99 mmol, 1.0 eq.), cesium carbonate (1.26 g, 3.85 mmol, 3.9 eq.) and dimethylsulfate (0.744 g, 5.72 mmol, 5.8 eq.) in acetone (16 mL) was stirred 6 h at room temperature. The resulting suspension was filtered and the solid was washed with acetone. The filtrate was concentrated in vacuo to yield 926 mg (quant.) of the title compound as orange oil, which was used in the next step without further purification. MS (m/e): 434.3(M+, 100%).

b) Step 2: (4,4-Difluoro-piperidin-1-yl)-[5-(1-isopropyl-piperidin-4-yloxy)-1-methyl-1H-indol-2-yl]-methanone To mixture of 4-[2-(4,4-difluoro-piperidine-1-carbonyl)-1-methyl-1H-indol-5-yloxy]-1-isopropyl-1-methyl-piperidinium as monomethylsulfate salt (120 mg, 0.2 mmol, 1.0 eq.), lithium hydride (5 mg, 0.5 mmol, 2.5 eq.) in N,N-dimethylformamide (0.5 mL) was added ethanethiol (0.05 mL, 0.6 mmol, 2.7 eq.). The reaction mixture was stirred 1 h at 100° C., cooled down to room temperature and partitioned between water and ethyl acetate. The aqueous layer was extracted with ethyl acetate. The combined organic phases were dried over sodium sulfate then filtered and concentrated in vacuo. The crude mixture was purified by column chromatography on silica eluting with DCM/2N NH$_3$ in methanol 19/1 to yield 89 mg (96%) of the title compound as white foam. MS (m/e): 420.5 (MH+, 100%).

Example 192

[5-(1-Cyclopropylmethyl-piperidin-4-yloxy)-1H-indol-2-yl]-morpholin-4-yl-methanone a) Step 1: 1-Cyclopropylmethyl-piperidin-4-one To a suspension of (bromomethyl)cyclopropane (500 mg, 4 mmol, 1.0 eq.) and 4-piperidone hydrate hydrochloride (579 mg, 4 mmol, 1.0 eq.) in acetonitrile (30 mL) was added sodium carbonate (1.148 g, 11 mmol, 3. eq.). The reaction mixture was stirred 16 h at 85° C. The resulting suspension was filtered and the solid was washed with acetonitrile. The filtrate was concentrated in vacuo and purified by column chromatography on silica eluting with DCM/2N NH$_3$ in methanol 97:3 to yield 339 mg (62%) of the tide compound as yellow oil. MS (m/e): 154.2 (MH+, 100%).

b) Step 2: 1-Cyclopropylmethyl-piperidin-4-ol

To a cold (0° C.) solution of 1-cyclopropylmethyl-piperidin-4-one (314 mg, 2 mmol, 1.0 eq.) in ethanol (4 mL) was added sodium borohydride (61 mg, 2 mmol, 0.75 eq.). The reaction mixture was stirred 16 h at room temperature. Water, sodium hydroxide and dichloromethane were added and the reaction mixture was stirred 2 h at room temperature. The aqueous layer was extracted with dichloromethane and the combined organic phases were dried over sodium sulfate, filtered then concentrated to dryness in vacuo to yield 160 mg (50%) of the tide compound as colorless oil, witch was used in the next step without further purification. MS (m/e): 156.3 (MH+, 100%).

c) Step 3: [5-(1-Cyclopropylmethyl-piperidin-4-yloxy)-1H-indol-2-yl]-morpholin-4-yl-methanone According to the procedure described for the synthesis of Example 1/Step 2 the title compound was synthesized from (5-hydroxy-1H-indol-2-yl)-morpholin-4-yl-methanone (Example 1, Step 1) and 1-cyclopropylmethyl-piperidin-4-ol (Example 192, Step 2). (m/e): 384.4 (MH+, 100%).

Example 193

[5-(1-Benzyl-piperidin-4-yloxy)-1H-indol-2-yl]-morpholin-4-yl-methanone

According to the procedure described for the synthesis of Example 1/Step 2 the tide compound was synthesized from (5-hydroxy-1H-indol-2-yl)-morpholin-4-yl-methanone (Example 1, Step 1) and 1-benzyl-4-hydroxy-piperidine (commercially available). (m/e): 419.52 (MH+, 100%).

Example 194

(4,4-Difluoro-piperidin-1-yl)-{5-[3-(methyl-propyl-amino)-propoxy]-1H-indol-2-yl}methanone as formic acid salt a) Step 1: 5-(3-Chloro-propoxy)-1H-indole-2-carboxylic acid ethyl ester To a solution of ethyl-5-hydroxyindole-2-carboxylate (15 g, 73 mmol, 1.0 eq.) and 1-bromo-3-chloropropane (8.8 mL, 88 mmol, 1.2 eq.) in 2-butanone (200 mL) was added potassium carbonate (12.1 g, 88 mmol, 1.2 eq.). The reaction mixture was stirred 160 h at 80° C. The reaction mixture was cooled down and partitioned between ethyl acetate and water. The aqueous phase was extracted with ethyl acetate. The combined organic phases were washed with water and brine then dried over sodium sulfate, filtered and concentrated in vacuo. The crude mixture was purified by column chromatography on silica eluting with cyclohexane/ethyl acetate 9:1 to yield 15.3 mg (74%) of the title compound as a light yellow solid. MS (m/e): 282.7 (MH+, 100%).

b) Step 2: 5-(3-Chloro-propoxy)-1H-indole-2-carboxylic acid

According to the procedure described for the synthesis of Example 5/step 2 [5-(3-chloro-propoxy)-1H-indole-2-carboxylic acid was synthesized from 5-(3-chloro-propoxy)-1H-indole-2-carboxylic acid ethyl ester. The title compound was yielded in 98% as an off-white solid. MS (m/e): 253.1 (M, 100%).

c) Step 3: [5-(3-Chloro-propoxy)-1H-indol-2-yl]-(4,4-difluoro-piperidin-1-yl)-methanone According to the procedure described for the synthesis of Example 5/step 3 [5-(3-chloro-propoxy)-1H-indol-2-yl]-(4,4-difluoro-piperidin-1-yl)-methanone was synthesized from 5-(3-chloro-propoxy)-1H-indole-2-carboxylic acid and 4,4'-difluoropiperidine (commercially available). The title compound was yielded in 76% as an off-white solid. MS (m/e): 357.8 (MH+, 100%).

d) Step 4: (4,4-Difluoro-piperidin-1-yl)-{5-[3-(methyl-propyl-amino)-propoxy]-1H-indol-2-yl}methanone as formic acid salt To a mixture of [5-(3-chloro-propoxy)-1H-indol-2-yl]-(4,4-difluoro-piperidin-1-yl)-methanone (42 mg, 0.12 mmol, 1.0 eq.) and potassium carbonate (50 mg, 0.35 mmol, 3.0 eq.) in N,N-dimethylformamide (1 mL) was added N-methyl-N-propylamine (13 mg, 0.18 mmol, 1.5 eq.). The reaction mixture was stirred 40 h at 80° C. and cooled down, then the crude mixture was directly purified by HPLC on a YMC Combiprep™ column eluting with water/acetonitrile/formic acid 90:10:0.1 to yield 2.1 mg (4%) of the title compound as a light yellow solid. MS (m/e): 440.5 (MH+, 100%).

According to the procedure described for the synthesis of Example 194/Step 4 further indole derivatives have been synthesized from [5-(3-chloro-propoxy)-1H-indol-2-yl]-(4,4-difluoro-piperidin-1-yl)-methanone with the respective amine mentioned in Table 3. The results are shown in Table 3 and comprise Example 195 to Example 208.

TABLE 3

| Ex. No | Systematic name | MW | Starting materials | MW found (M + H)+ |
|---|---|---|---|---|
| 195 | (4,4-Difluoro-piperidin-1-yl)-{5-[3-(ethyl-propyl-amino)-propoxy]-1H-indol-2-yl}-methanone as formic acid salt | 407.5 | [5-(3-Chloro-propoxy)-1H-indol-2-yl]-(4,4-difluoro-piperidin-1-yl)-methanone and N-ethyl-N-propylamine (commercially available) | 408.5 |
| 196 | (4,4-Difluoro-piperidin-1-yl)-{5-[3-(isopropyl-methyl-amino)-propoxy]-1H-indol-2-yl}-methanone as formic acid salt | 393.5 | [5-(3-Chloro-propoxy)-1H indol-2-yl]-(4,4-difluoro-piperidin-1-yl)-methanone and N-methyl-N-isopropylamine (commercially available) | 394.5 |
| 197 | (4,4-Difluoro-piperidin-1-yl)-[5-(3-pyrrolidin-1-yl-propoxy)-1H-indol-2-yl]-methanone as formic acid salt | 391.5 | [5-(3-Chloro-propoxy)-1H-indol-2-yl]-(4,4-difluoro-piperidin-1-yl)-methanone and pyrrolidine (commercially available) | 392.5 |
| 198 | [5-(3-Azepan-1-yl-propoxy)-1Hindol-2-yl]-(4,4-difluoro-piperidin-1-yl)-methanone as formic acid salt | 419.5 | [5-(3-Chloro-propoxy)-1H-indol-2-yl]-(4,4-difluoro-piperidin-1-yl)-methanone and hexamethyleneimine (commercially available) | 420.6 |
| 199 | (4,4-Difluoro-piperidin-1-yl)-{5-[3-(3-methyl-piperidin-1-yl)-propoxy]-1H-indol-2-yl}-methanone as formic acid salt | 419.5 | [5-(3-Chloro-propoxy)-1H-indol-2-yl]-(4,4-difluoro-piperidin-1-yl)-methanone and (rac)-3-methylpiperidine (commercially available) | 420.5 |
| 200 | (4,4-Difluoro-piperidin-1-yl)-{5-[3-(2,6-cis-dimethyl-piperidin-1-yl)-propoxy]-1H-indol-2-yl}-methanone as formic acid salt | 433.5 | [5-(3-Chloro-propoxy)-1H-indol-2-yl]-(4,4-difluoro-piperidin-1-yl)-methanone and cis-2,6-dimethyl-piperidine (commercially available) | 434.5 |
| 201 | (4,4-Difluoro-piperidin-1-yl)-[5-(3-thiomorpholin-4-yl-propoxy)-1H-indol-2-yl]-methanone as formic acid salt | 423.5 | [5-(3-Chloro-propoxy)-1H-indol-2-yl]-(4,4-difluoro-piperidin-1-yl)-methanone and thiomorpholine (commercially available) | 424.5 |
| 202 | (4,4-Difluoro-piperidin-1-yl)-{5-[3-(2,5-dihydro-pyrrol-1-yl)-propoxy]-1H-indol-2-yl}-methanone as formic acid salt | 389.5 | [5-(3-Chloro-propoxy)-1H-indol-2-yl]-(4,4-difluoro-piperidin-1-yl)-methanone and 3-pyrroline (commercially available) | 390.4 |
| 203 | (4,4-Difluoro-piperidin-1-yl)-{5-[3-(2-methyl-pyrrolidin-1-yl)-propoxy]-1H-indol-2-yl}-methanone as formic acid salt | 405.5 | [5-(3-Chloro-propoxy)-1H-indol-2-yl]-(4,4-difluoro-piperidin-1-yl)-methanone and rac-2-methyl-pyrrolidine (commercially available) | 405.6 |
| 204 | (4,4-Difluoro-piperidin-1-yl)-{5-[3-(2,5-cis/trans-dimethyl-pyrrolidin-1-yl)-propoxy]-1H-indol-2-yl}-methanone as formic acid salt | 419.5 | [5-(3-Chloro-propoxy)-1H-indol-2-yl]-(4,4-difluoro-piperidin-1-yl)-methanone and cis/trans-2,5-dimethyl-pyrrolidine (commercially available) | 420.6 |
| 205 | (4,4-Difluoro-piperidin-1-yl)-{5-[3-(3S-hydroxy-pyrrolidin-1-yl)-propoxy]-1H-indol-2-yl}-methanone as formic acid salt | 407.5 | [5-(3-Chloro-propoxy)-1H-indol-2-yl]-(4,4-difluoro-piperidin-1-yl)-methanone and 3S-hydroxy-pyrrolidine (commercially available) | 408.6 |
| 206 | (4,4-Difluoro-piperidin-1-yl)-{5-[3-(3-dimethylamino-pyrrolidin-1-yl)-propoxy]-1H-indol-2-yl}-methanone as formic acid salt | 434.5 | [5-(3-Chloro-propoxy)-1H-indol-2-yl]-(4,4-difluoro-piperidin-1-yl)-methanone and rac-2-N,N-dimethylamino-pyrrolidine (commercially available) | 435.6 |

TABLE 3-continued

| Ex. No | Systematic name | MW | Starting materials | MW found (M + H)+ |
|---|---|---|---|---|
| 207 | (4,4-Difluoro-piperidin-1-yl)-[5-(3-piperidin-1-yl-propoxy)-1H-indol-2-yl]-methanone | 405.5 | [5-(3-Chloro-propoxy)-1H-indol-2-yl]-(4,4-difluoro-piperidin-1-yl)-methanone and piperidine (commercially available) | 406.5 |
| 208 | (4,4-Difluoro-piperidin-1-yl)-[5-(3-morpholin-4-yl-propoxy)-1H-indol-2-yl]-methanone | 407.5 | [5-(3-Chloro-propoxy)-1H-indol-2-yl]-(4,4-difluoro-piperidin-1-yl)-methanone and morpholine (commercially available) | 408.5 |

Example 209

{5-[3-(4,4-Difluoro-piperidin-1-yl)-propoxy]-1H-indol-2-yl}-morpholin-4-yl-methanone a) Step 1: [5-(3-Chloro-propoxy)-1H-indol-2-yl]-morpholin-4-yl-methanone According to the procedure described for the synthesis of Example 5/step 3 [5-(3-chloro-propoxy)-1H-indol-2-yl]-morpholin-4-yl-methanone was synthesized from 5-(3-chloro-propoxy)-1H-indole-2-carboxylic acid and morpholine (commercially available). The title compound was yielded in 92% as an off-white solid. MS (m/e): 323.9 (MH+, 100%).

b) Step 2: {5-[3-(4,4-Difluoro-piperidin-1-yl)-propoxy]-1H-indol-2-yl}-morpholin-4-yl -methanone According to the procedure described for the synthesis of Example 194/step 4, {5-[3-(4,4-difluoro-piperidin-1-yl)-propoxy]-1H-indol-2-yl}-morpholin-4-yl-methanone was synthesized from [5-(3-chloro-propoxy)-1H-indol-2-yl]-morpholin-4-yl-methanone and 4,4'-difluoropiperidine hydrochloride (commercially available). The title compound was yielded in 54% as a brown solid. MS (m/e): 408.5 (MH+, 100%).

Example 210

[5-(1-Cyclopropyl-piperidin-4-yloxy)-1H-indol-2-yl]-morpholin-4-yl-methanone a) Step 1: 3-[Cyclopropyl-(2-ethoxycarbonyl-ethyl)-amino]-propionic acid ethyl ester A mixture of ethyl acrylate (30.0 g, 300 mmol, 2.0 eq.) and cyclopropyl amine (8.5 mL, 149 mmol, 1.0 eq.) in absolute ethanol (45 mL) was stirred 24 h at room temperature. The crude mixture was purified by fractionated distillation in vacuo (20 mBar). One fraction was collected (boiling point: 135° C. at 20 mBar), yielding to 20.58 g (54%) of the desired product as a colorless oil. MS (m/e): 274.3 (MH+, 100%).

b) Step 2: 1-Cyclopropyl-piperidin-4-one

A solution of 3-[cyclopropyl-(2-ethoxycarbonyl-ethyl)-amino]-propionic acid ethyl ester (10.0 g, 39 mmol, 1.0 eq.) in anhydrous tetrahydrofuran (65 mL) was added dropwise to a solution of sodium hydride (60% oil dispersion, 2.33 g, 58 mmol, 1.5 eq.) in anhydrous tetrahydrofuran (65 mL). Absolute ethanol (1.79 g, 39 mmol, 1.0 eq.) was then added. The resulting mixture was heated under reflux for 24 h. The solution obtained was neutralized (pH: 7) with diluted acetic acid and partitioned between water and ethyl acetate. The aqueous layer was extracted with ethyl acetate. The combined extracts were dried over sodium sulfate and the solvent was removed in vacuo, yielding to 10.2 g of reddish oil.

This crude oil was then heated under reflux in 18% w/w hydrochloric acid (130 mL) for 5 h. After basification with sodium hydroxide (ca. 31 g, pH: ca. 12), the crude mixture was extracted with ethyl acetate. The combined extracts were dried over sodium sulfate and the solvent was removed in vacuo. The crude mixture was purified by fractionated distillation in vacuo (20 mbar). One fraction was collected (boiling point: 75° C. at 20 mbar), yielding to 3.6 g (67%) of the desired product as a colorless oil. MS (m/e): 140.0 (MH+, 100%).

c) Step 3: 1-Cyclopropyl-piperidin-4-ol

To a cold (0° C.) solution of 1-cyclopropyl-piperidin-4-one (1.5 g, 11 mmol, 1.0 eq.) in absolute ethanol was added sodium borohydride (306 mg, 8 mmol, 0.75 eq.). The reaction mixture was stirred at room temperature for 65 h. The mixture was concentrated in vacuo. Ice water (10 mL) was added, followed by an aqueous solution of sodium hydroxide (28% w/w, ca. 10 mL) and dichloromethane (20 mL). The mixture was stirred at room temperature for 2 h. After phase separation, the aqueous layer was extracted with dichloromethane. The combined organic layers were washed with brine, dried over sodium sulfate, filtered and evaporated in vacuo. The crude mixture was purified on silica eluting with DCM/2N $NH_3$ in methanol 93/7, yielding to 1.44 g (95%) of the desired product as a colorless oil. MS (m/e): 423.1 (MH+, 100%)

d) Step 4: [5-(1-Cyclopropyl-piperidin-4-yloxy)-1H-indol-2-yl]-morpholin-4-yl-methanone According to the procedure described for the synthesis of Example 1/step 2 [5-(1-cyclopropyl-piperidin-4-yloxy)-1H-indol-2-yl]-morpholin-4-yl-methanone was synthesized from (5-hydroxy-1H-indol-2-yl)-morpholin-4-yl-methanone (Example 1, Step 1) and 1-cyclopropyl-piperidin-4-ol (Example 201, Step 3). The title compound was yielded in 14% as a white solid. MS (m/e): 370.5 (MH+, 100%).

Example 211

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 212

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 213

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 214

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 215

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 216

The compounds of formula I and their pharmaceutically acceptable salts possess valuable pharmacological properties. Specifically, it has been found that the compounds of the present invention are good histamine 3 receptor (H3R) antagonists and/or inverse agonists. The following test was carried out in order to determine the activity of the compounds of formula (I).

Binding assay with $^3$H-(R)α-methylhistamine

Saturation binding experiments were performed using HR$^3$—CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3—CHO cell line. An appropriate amount of protein, e.g. approximately 500 cpm binding of RAMH at Kd, were incubated for 1 hour at room temperature in 250 μl final volume in 96-well plates in presence of $^3H(R)\alpha$-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. $K_i$'s were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 2 | 23 |
| Example 117 | 77 |
| Example 140 | 93 |

It is to be understood that the invention is not limited to the particular embodiments of the invention described above, as variations of the particular embodiments may be made and still fall within the scope of the appended claims.

What is claimed is:

1. A compound of the formula I:

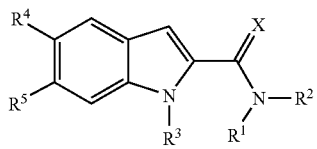

wherein
X is O or S;
$R^1$ is selected from the group consisting of hydrogen,
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocyclyl ring may be unsubstituted or substituted with one or two lower alkyl groups;
$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated heterocyclic ring
being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen;
$R^3$ is selected from the group consisting of hydrogen, lower alkyl, lower alkoxyalkyl, lower halogenalkyl, lower cycloalkylalkyl, lower alkylsulfonyl and lower alkanoyl;
$R^4$ is —O-Het and $R^5$ is hydrogen, or
$R^4$ is hydrogen or fluoro and $R^5$ is —O-Het;
Het is selected from

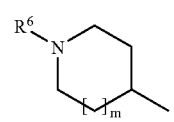

Het 1

-continued

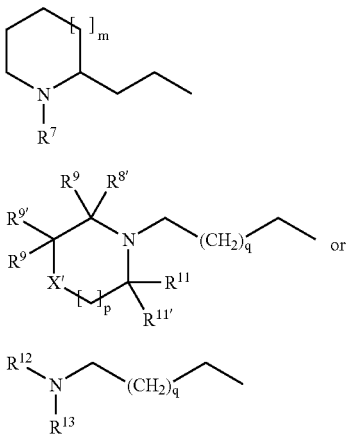

Het 2

Het 3

Het 4 wherein
m is 0, 1 or 2;
$R^6$ is selected from lower alkyl, cycloalkyl, lower cycloalkylalkyl and lower phenylalkyl;
n is 0, 1 or 2;
$R^7$ is lower alkyl;
p is 0, 1 or 2;
q is 0, 1 or 2;
X' is selected from $CR^{10}R^{10'}$, O and S;
$R^8$, $R^{8'}$, $R^9$, $R^{9'}$, $R^{10}$, $R^{10'}$, $R^{11}$ and $R^{11'}$ independently from each other are selected from the group consisting of hydrogen, lower alkyl, hydroxy, halogen and dialkylamino, or
$R^9$ and $R^{10}$ together form a double bond;
$R^{12}$ is lower alkyl;
$R^{13}$ is $C_3$-$C_6$-alkyl;
and pharmaceutically acceptable salts thereof.

2. The compound according to claim 1, wherein
X is O or S;
$R^1$ is selected from the group consisting of hydrogen, lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocyclyl ring may be unsubstituted or substituted with one or two lower alkyl groups;
$R^2$ is selected from the group consisting of hydrogen, lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated heterocyclic ring
being unsubstituted or substituted by one, two or three groups independently selected from lower alkyl, halogen, halogenalkyl, hydroxy, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen;
$R^3$ is hydrogen or lower alkyl;
$R^4$ is —O-Het and $R^5$ is hydrogen, or
$R^4$ is hydrogen or fluoro and $R^5$ is —O-Het;
Het is selected from Het 1

Het 2

Het 3' wherein
m is 0, 1 or 2;
$R^6$ is lower alkyl;
n is 0, 1 or 2;
$R^7$ is lower alkyl;
p is 0, 1 or 2;
q is 0, 1 or 2;
$R^8$ is hydrogen or lower alkyl;
and pharmaceutically acceptable salts thereof.

3. The compound according to claim 1, wherein $R^1$ is selected from the group consisting of
lower alkyl, lower alkenyl, lower alkinyl, cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycly ring may be unsubstituted or substituted with one or two lower alkyl groups, and
$R^2$ is hydrogen or lower alkyl.

4. The compound according to claim 1, wherein $R^1$ is selected from the group consisting of
lower alkyl, cycloalkyl, lower cycloalkylalkyl, lower alkoxyalkyl,
lower phenylalkyl,
lower heteroarylalkyl, and
lower heterocyclylalkyl wherein the heterocyclyl ring may be unsubstituted or substituted with one or two lower alkyl groups, and
$R^2$ is hydrogen or lower alkyl.

5. The compound according to claim 1, wherein $R^1$ and $R^2$ are lower alkyl.

6. The compound according to claim 1, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

7. The compound according to claim 6, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said saturated heterocyclic ring being unsubstituted or substituted by one, two or three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

8. The compound according to claim 7, wherein $R^1$ and $R^2$ together with the nitrogen atom to which they are attached form a heterocyclic ring selected from morpholinyl, 2,6-dimethylmorpholinyl, azepanyl, piperidinyl, 2-methylpiperidinyl, 4-methylpiperidinyl, pyrrolidinyl, 2-methylpyrrolidinyl and azetidinyl.

9. The compound according to claim 1, wherein $R^3$ is hydrogen or lower alkyl.

10. The compound according to claim 1, wherein $R^4$ is —O-Het and $R^5$ is hydrogen.

11. The compound according to claim 1, wherein $R^4$ is hydrogen or fluoro and $R^5$ is —O-Het.

12. The compound according to claim 1, wherein Het signifies

Het 1 wherein m is 0, 1 or 2, and $R^6$ is selected from lower alkyl, cycloalkyl, lower cycloalkylalkyl and lower phenylalkyl.

13. The compound according to claim 12, wherein $R^6$ is lower alkyl.

14. The compound according to claim 12, wherein m is 0.

15. The compound according to claim 12, wherein m is 1.

16. The compound according to claim 1, wherein Het signifies

Het 2 wherein n is 0, 1 or 2; and $R^7$ is lower alkyl.

17. The compound according to claim 16, wherein n is 0.

18. The compound according to claim 16, wherein n is 1.

19. The compound according to claim 1, wherein Het signifies

Het 3 wherein p is 0, 1 or 2; q is 0, 1 or 2; X' is selected from $CR^{10}R^{10'}$, O and S; and
$R^8$, $R^{8'}$, $R^9$, $R^{9'}$, $R^{10}$, $R^{10'}$, $R^{11}$ and $R^{11'}$ independently from each other are selected from the group consisting of hydrogen, lower alkyl, hydroxy, halogen and dialkylamino, or
$R^9$ and $R^{10}$ together form a double bond.

20. The compound according to claim 19, wherein p is 0, 1 or 2, q is 0, 1 or 2, X' is $CR^{10}R^{10'}$ and $R^8$, $R^{8'}$, $R^9$, $R^{9'}$, $R^{10}$, $R^{10'}$, $R^{11}$ and $R^{11'}$ are hydrogen or lower alkyl.

21. The compound according to claim 19, wherein p is 1.

22. The compound according to claim 1, wherein Het signifies

Het 4 wherein q is 0, 1 or 2, $R^{12}$ is lower alkyl and $R^{13}$ is $C_3$-$C_6$-alkyl.

23. The compound according to claim 1, wherein said compound is selected from the group consisting of:
morpholin-4-yl-[5-(3-piperidin-1-yl-propoxy)-1H-indol-2-yl]-methanone,
[5-(1-isopropyl-pyrrolidin-3-yloxy)-1H-indol-2-yl]-morpholin-4-yl-methanone,
5-(1-isopropyl-piperidin-4-yloxy)-1H-indole-2-carboxylic acid tert-butylamide,
(2,5-dihydro-pyrrol-1-yl)-[5-(1-isopropyl-piperidin-4-yloxy)-1H-indol-2-yl]-methanone,
(3-hydroxy-pyrrolidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid ethyl-(2-methoxy-ethyl)-amide,
5-(1-isopropyl-piperidin-4-yloxy)-1H-indole-2-carboxylic acid isopropyl-methyl-amide,
5-(1-isopropyl-piperidin-4-yloxy)-1H-indole-2-carboxylic acid (2-morpholin-4-yl-ethyl)-amide,
5-(1-isopropyl-piperidin-4-yloxy)-1H-indole-2-carboxylic acid (2-piperidin-1-yl-ethyl)-amide,
5-(1-isopropyl-piperidin-4-yloxy)-1H-indole-2-carboxylic acid (1-ethyl-piperidin-3-yl)-amide,
[5-(1-isopropyl-piperidin-4-yloxy)-1H-indol-2-yl]-pyrrolidin-1-yl-methanone,
[5-(1-isopropyl-piperidin-4-yloxy)-1H-indol-2-yl]-morpholin-4-yl-methanone,
[5-(1-isopropyl-piperidin-4-yloxy)-1H-indol-2-yl]-(4-methoxy-piperidin-1-yl)-methanone,
(4,4-difluoro-piperidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid [2-(2-methyl-piperidin-1-yl)-ethyl]-amide,
[5-((S)-1-isopropyl-pyrrolidin-3-yloxy)-1H-indol-2-yl]-morpholin-4-yl-methanone,
[6-(1-isopropyl-piperidin-4-yloxy)-1H-indol-2-yl]-morpholin-4-yl-methanone,
(3,3-difluoro-piperidin-1-yl)-[5-(1-isopropyl-piperidin-4-yloxy)-1H-indol-2-yl]-methanone,
(4,4-difluoro-piperidin-1-yl)-[1-isopropyl-5-(1-isopropyl-piperidin-4-yloxy)-1H-indol-2-yl]-methanone,
(4,4-difluoro-piperidin-1-yl)-[5-(1-isopropyl-piperidin-4-yloxy)-1-(2-methoxy-ethyl)-1H-indol-2-yl]-methanone,
(4,4-difluoro-piperidin-1-yl)-[5-(1-isopropyl-piperidin-4-yloxy)-1-(2,2,2-trifluoro-ethyl)-1H-indol-2-yl]-methanone,
[1-cyclopropylmethyl-5-(1-isopropyl-piperidin-4-yloxy)-1H-indol-2-yl]-(4,4-difluoro-piperidin-1-yl)-methanone,
[5-(1-isopropyl-piperidin-4-yloxy)-1-(2,2,2-trifluoro-ethyl)-1H-indol-2-yl]-morpholin-4-yl-methanone,
(4,4-difluoro-piperidin-1-yl)-[5-(1-isopropyl-piperidin-4-yloxy)-1-methanesulfonyl-1H-indol-2-yl]-methanone,
1-[2-(4,4-difluoro-piperidine-1-carbonyl)-5-(1-isopropyl-piperidin-4-yloxy)-indol-1-yl]-ethanone,
(4,4-difluoro-piperidin-1-yl)-[5-(1-isopropyl-piperidin-4-yloxy)-1-methyl-1H-indol-2-yl]-methanone,
[5-(1-cyclopropylmethyl-piperidin-4-yloxy)-1H-indol-2-yl]-morpholin-4-yl-methanone,
(4,4-difluoro-piperidin-1-yl)-[5-(3-pyrrolidin-1-yl-propoxy)-1H-indol-2-yl]-methanone as formic acid salt,
(4,4-difluoro-piperidin-1-yl)-{5-[3-(2-methyl-pyrrolidin-1-yl)-propoxy]-1H-indol-2-yl}-methanone as formic acid salt,
(4,4-difluoro-piperidin-1-yl)-[5-(3-piperidin-1-yl-propoxy)-1H-indol-2-yl]-methanone, and
[5-(1-cyclopropyl-piperidin-4-yloxy)-1H-indol-2-yl]-morpholin-4-yl-methanone,
and pharmaceutically acceptable salts thereof.

24. The compound according to claim 1, wherein said compound is selected from the group consisting of:
morpholin-4-yl-[5-(3-piperidin-1-yl-propoxy)-1H-indol-2-yl]-methanone,
[5-(1-isopropyl-pyrrolidin-3-yloxy)-1H-indol-2-yl]-morpholin-4-yl-methanone,
(2,5-dihydro-pyrrol-1-yl)-[5-(1-isopropyl-piperidin-4-yloxy)-1H-indol-2-yl]-methanone,
(3-hydroxy-pyrrolidin-1-yl)-[5-(1-isopropyl-piperidin-4-yloxy)-1H-indol-2-yl]-methanone,
5-(1-isopropyl-piperidin-4-yloxy)-1H-indole-2-carboxylic acid isopropyl-methyl-amide,
[5-(1-isopropyl-piperidin-4-yloxy)-1H-indol-2-yl]-pyrrolidin-1-yl-methanone,
[5-(1-isopropyl-piperidin-4-yloxy)-1H-indol-2-yl]-morpholin-4-yl-methanone,
[5-(1-isopropyl-piperidin-4-yloxy)-1H-indol-2-yl]-(4-methoxy-piperidin-1-yl)-methanone,
(4,4-difluoro-piperidin-1-yl)-[5-(1-isopropyl-piperidin-4-yloxy)-1H-indol-2-yl]-methanone,
[6-(1-isopropyl-piperidin-4-yloxy)-1H-indol-2-yl]-morpholin-4-yl-methanone,
(3,3-difluoro-piperidin-1-yl)-[5-(1-isopropyl-piperidin-4-yloxy)-1H-indol-2-yl]-methanone,
(4,4-difluoro-piperidin-1-yl)-[1-isopropyl-5-(1-isopropyl-piperidin-4-yloxy)-1H-indol-2-yl]-methanone,
(4,4-difluoro-piperidin-1-yl)-[5-(1-isopropyl-piperidin-4-yloxy)-1-(2,2,2-trifluoro-ethyl)-1H-indol-2-yl]-methanone,
(4,4-difluoro-piperidin-1-yl)-[5-(1-isopropyl-piperidin-4-yloxy)-1-methyl-1H-indol-2-yl]-methanone, and
[5-(1-cyclopropyl-piperidin-4-yloxy)-1H-indol-2-yl]-morpholin-4-yl-methanone,
and pharmaceutically acceptable salts thereof.

25. A process for the manufacture of compounds according to claim 1, comprising the steps of:
a) reacting a compound of the formula II

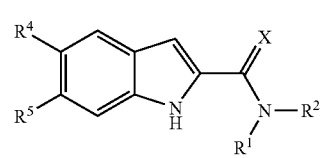

II wherein X, $R^1$ and $R^2$ are as defined in claim 1 and one of $R^4$ and $R^5$ is —OH and the other one is H, with an alcohol of the formula III HO-Het    III wherein Het is as defined in claim 1,
in the presence of a trialkylphosphine or triphenylphosphine and of a diazo compound to obtain a compound of the formula Ia

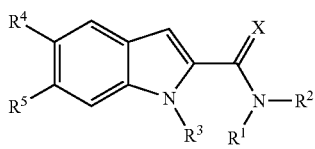

wherein R³ is hydrogen, and optionally alkylating this compound to obtain a compound of formula Ia'

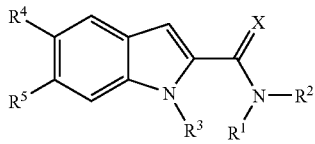

wherein R³ is lower alkyl,
and if desired,
converting the compound obtained into a pharmaceutically acceptable acid addition salt, or alternatively,
   b) coupling a compound of formula IV

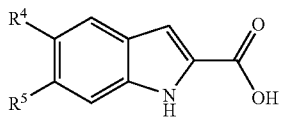

wherein one of R⁴ and R⁵ is —O-Het as defined in claim 1 and the other one is H, with an amine of the formula V

H—NR¹R²    V wherein R¹ and R² are as defined in claim 1,
under basic conditions to obtain a compound of the formula Ib

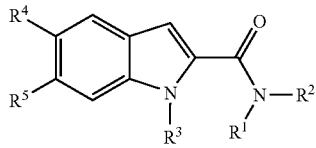

wherein R³ is hydrogen, and optionally alkylating this compound to obtain a compound of formula Ib'

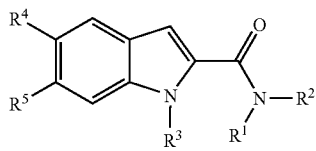

wherein R³ is lower alkyl,
and if desired,
converting the compound obtained into a pharmaceutically acceptable acid addition salt.

26. A pharmaceutical composition comprising a therapeutically effective amount of a compound according to claim 1 as well as a pharmaceutically acceptable carrier and/or adjuvant.

* * * * *

UNITED STATES PATENT AND TRADEMARK OFFICE
CERTIFICATE OF CORRECTION

PATENT NO. : 7,361,682 B2 Page 1 of 1
APPLICATION NO. : 11/157093
DATED : April 22, 2008
INVENTOR(S) : Silvia Gatti McArthur et al.

It is certified that error appears in the above-identified patent and that said Letters Patent is hereby corrected as shown below:

In Claim 1, Column (79) and

In Claim 19, Column (82) please delete

" 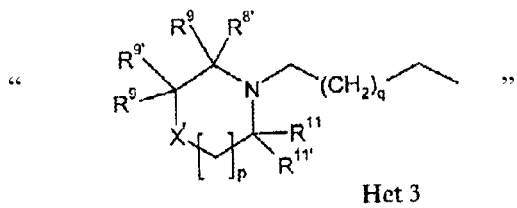 "

And insert

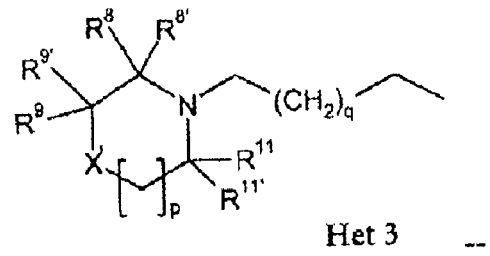

-- --

Signed and Sealed this

Twenty-second Day of July, 2008

JON W. DUDAS
*Director of the United States Patent and Trademark Office*